(12) United States Patent
Van Damme et al.

(10) Patent No.: US 9,932,600 B2
(45) Date of Patent: Apr. 3, 2018

(54) DISEASE RESISTANT TOMATO PLANTS

(71) Applicant: Enza Zaden Beheer B.V., Enkhuizen (NL)

(72) Inventors: Mireille Maria Augusta Van Damme, Norwich (GB); Augustinus Franciscus Johannes Maria Van Den Ackerveken, Houten (NL); Tieme Zeilmaker, Amersfoort (NL)

(73) Assignee: ENZA ZADEN BEHEER B.V., Enkhuizen (NL)

( * ) Notice: Subject to any disclaimer, the term of this patent is extended or adjusted under 35 U.S.C. 154(b) by 0 days.

(21) Appl. No.: 15/190,439

(22) Filed: Jun. 23, 2016

(65) Prior Publication Data
US 2016/0298131 A1 Oct. 13, 2016

Related U.S. Application Data

(60) Continuation of application No. 14/528,707, filed on Oct. 30, 2014, now Pat. No. 9,546,373, which is a division of application No. 14/250,875, filed on Apr. 11, 2014, now Pat. No. 9,121,029, which is a division of application No. 12/525,236, filed as application No. PCT/EP2008/000718 on Jan. 30, 2008, now Pat. No. 8,742,207.

(30) Foreign Application Priority Data

Feb. 1, 2007 (WO) ................ PCT/EP2007/050976

(51) Int. Cl.
| C12N 15/82 | (2006.01) |
| C12N 9/02 | (2006.01) |
| C12N 15/01 | (2006.01) |
| A01H 1/06 | (2006.01) |
| A01H 5/08 | (2018.01) |

(52) U.S. Cl.
CPC ........... *C12N 15/8218* (2013.01); *A01H 1/06* (2013.01); *A01H 5/08* (2013.01); *C12N 9/0071* (2013.01); *C12N 15/01* (2013.01); *C12N 15/8279* (2013.01); *C12N 15/8282* (2013.01); *C12Y 114/11* (2013.01)

(58) Field of Classification Search
None
See application file for complete search history.

(56) References Cited

U.S. PATENT DOCUMENTS

| 5,866,776 | A | 2/1999 | Marie De Wit |
| 6,100,451 | A | 8/2000 | Chappell et al. |
| 6,271,439 | B1 | 8/2001 | Johal et al. |
| 7,323,338 | B2 | 1/2008 | Amir |
| 7,777,097 | B2 | 8/2010 | Glazebrook et al. |
| 8,237,019 | B2 | 8/2012 | Van Den Ackerveken et al. |
| 8,354,570 | B2 | 1/2013 | Van Den Ackerveken et al. |
| 8,575,432 | B2 | 11/2013 | Van Den Ackerveken |
| 8,742,207 | B2 | 6/2014 | Van Damme et al. |
| 8,796,511 | B2 | 8/2014 | Van Den Ackerveken et al. |
| 9,121,029 | B2 | 9/2015 | Van Damme et al. |
| 9,546,373 | B2 | 1/2017 | Van Damme et al. |
| 2003/0172396 | A1 | 9/2003 | Cohen et al. |
| 2006/0143729 | A1 | 6/2006 | Alexandrov et al. |
| 2016/0160233 | A1 | 6/2016 | Van Schie et al. |
| 2016/0298130 | A1 | 10/2016 | Van Damme et al. |
| 2016/0326543 | A1 | 11/2016 | Van Damme et al. |
| 2016/0326544 | A1 | 11/2016 | Van Damme et al. |
| 2016/0333370 | A1 | 11/2016 | Van Schie et al. |

FOREIGN PATENT DOCUMENTS

| EP | 0474857 A1 | 3/1992 |
| EP | 1033405 A2 | 2/2000 |
| EP | 2455473 A1 | 5/2012 |
| WO | 9115585 A1 | 10/1991 |
| WO | 9636697 A1 | 11/1996 |
| WO | 1998/04586 A2 | 2/1998 |
| WO | 9832325 A1 | 7/1998 |
| WO | 9945125 A2 | 9/1999 |
| WO | 2000/70016 A2 | 11/2000 |
| WO | 0078981 A1 | 12/2000 |
| WO | 2001/55347 A1 | 8/2001 |
| WO | 0161021 A2 | 8/2001 |
| WO | 2002/061101 A2 | 8/2002 |
| WO | 2002/088301 A2 | 11/2002 |
| WO | 03000906 A2 | 1/2003 |

(Continued)

OTHER PUBLICATIONS

Aubert et al., "Transport, Compartmentation, and Metabolism of Homosernine in Higher Plant Cells", Plant Physiology, vol. 116, 1998, pp. 547-557.

Balass et al., "Identification of a Constitutive 45 kDa Soluble Protein Associated with Resistance to Downy Mildew in Muskmelon (*Cucumis Melo* L.), Line PI 124111 F", Physiological and Molecular Plant Pathology, vol. 41, 1992, pp. 387-396.

Bhattacharyya et al., "Identification of a Large Cluster of Coiled Coil-Nucleotide Binding Site-Leucine Rich Repeat-Type Genes from the Rps1 Region Containing Phytophthora Resistance Genes in Soybean", Theor Appl Genet, vol. 111, 2005, pp. 75-86.

(Continued)

*Primary Examiner* — Medina A Ibrahim
(74) *Attorney, Agent, or Firm* — Morrison & Foerster LLP

(57) ABSTRACT

The present invention relates to a plant, which is resistant to a pathogen of viral, bacterial, fungal or oomycete origin, wherein the plant has a reduced level, reduced activity or complete absence of DMR6 protein as compared to a plant that is not resistant to the said pathogen, in particular organisms of the Fungi or the phylum Oomycota. The invention further relates to a method for obtaining a plant, which is resistant to a pathogen of viral, bacterial, fungal or oomycete origin, comprising reducing the endogenous level or activity of DMR6 protein in the plant. In addition, the invention relates to the use of a DMR6 promotor for providing disease resistant plants.

11 Claims, 19 Drawing Sheets

(56) References Cited

FOREIGN PATENT DOCUMENTS

| WO | 2004/024079 A2 | 3/2004 |
|---|---|---|
| WO | 2006032707 A2 | 3/2006 |
| WO | 2006047358 A1 | 5/2006 |
| WO | 2007/051483 A1 | 5/2007 |
| WO | 2007/051626 A2 | 5/2007 |
| WO | 2008/092505 A1 | 8/2008 |
| WO | 2008/092659 A1 | 8/2008 |
| WO | 2015/011101 A1 | 1/2015 |
| WO | 2015/029031 A1 | 3/2015 |
| WO | 2015/106796 A1 | 7/2015 |
| WO | 2015/193418 A1 | 12/2015 |

OTHER PUBLICATIONS

Bouchez et al., "Functional Genomics in Plants", Plant Physiology, vol. 118, 1998, pp. 725-732.

Brouwer et al., "Fine Mapping of Three Quantitative Trait Loci for Late Blight Resistance in Tomato using near Isogenic Lines (NILs) and Sub-NILs", Theoretical and Applied Genetics, vol. 108, 2004, pp. 628-638.

Brouwer et al., "QTL Analysis of Quantitative Resistance to Phytophthora Infestans (Late Blight) in Tomato and Comparisons with Potato", Genome, vol. 27, 2004, pp. 475-492.

Budiman et al., "A Deep-Coverage Tomato BAC Library and Prospects toward Development of an STC Framework for Genome Sequencing", Genome Research, vol. 10, 2000, pp. 129-136.

Burnham et al., "Quantitative Trait Loci for Partial Resistance to Phytophthora Sojae in Soybean", Crop Science, vol. 43, Sep.-Dec. 2003, pp. 1610-1617.

Charlotte, Elliott, "Relative Susceptibility to Pythium Root Rot of Twelve Dent Corn Inbreds", Journal of Agricultural Research, vol. 64, No. 12, Jun. 15, 1992, pp. 711-723.

Clough et al., "Floral Dip: A Simplified Method for Agrobacterium-Mediated Transformation of Arabidopsis Thaliana", The Plant Journal, vol. 16, No. 6, 1998, pp. 735-743.

Conrath et al,, "Enhanced Resistance to Phytophthora Infestans and Alternaria Solani in Leaves and Tubers, Respectively, of Potato Plants with Decreased Activity of the Plastidic ATP/ADP Transporter", Planta, vol. 19, 2003, pp. 75-83.

Crowe et al., "CATMA: A Complete Arabidopsis GST Database", Nucleic Acids Research, vol. 31, No. 1, 2003, pp. 156-158.

De Wit, P. J. G. M., "Molecular Characterization of Gene-for-Gene Systems in Plant-Fungus Interactions and the Application of Avirulence Genes in Control of Plant Pathogens", Annu. Rev. Phytopathol., vol. 30, 1992, pp. 391-418.

EBI Accession No. AF082525, Available at <http://www.ebi.ac.uk/ena/data/view/AF082525&display=text>, Jun. 1, 1999, 2 pages.

EBI Database Accession No. DQ208192, Available at <http://www.ebi.ac.uk/ena/data/view/ABB20895&,display=text, Sep. 6, 2006, 2 pages.

"Federal Register", vol. 76, No. 27, Feb. 9, 2011, 14 pages.

Fischer et al., "Quantitative Trait Locus Analysis of Fungal Disease Resistance Factors on a Molecular Map of Grapevine", Theoretical and Applied Genetics, vol. 108, 2004, pp. 501-515.

Franchel et al., "Positional Cloning of a Candidate Gene for Resistance to the Sunflower Downy Mildew, Plasmopara Halstedii Race 300", Theoretical and Applied Genetics, vol. 126, 2013, pp. 359-367.

Friedrich et al., "NIM1 Overexpression in *Arabidopsis* Potentiates Plant Disease Resistance and Results in Enhanced Effectiveness of Fungicides", MPMI, vol. 14, No. 9, The American Phytopathological Society, 2001, pp. 1114-1124.

Gaspero et al., "Resistance Gene Analogs are Candidate Markers for Disease-Resistance Genes in Grape (*Vitis* spp.)", Theoretical and Applied Genetics, vol. 106, 2002, pp. 163-172.

"Geneseq Database Accession No. AAG45151", Oct. 18, 2000, 4 pages.

Giovanini et al.,"Gene-for-Gene Defense of Wheat against the Hessian Fly Lacks a Classical Oxidative Burst", Molecular Plant-Microbe Interactions, vol. 19, No. 9, 2006, pp. 1023-1033.

Gurr et al., "Engineering Plants with Increased Disease Resistance: How are we going to express it?", Trends Biotechnology, vol. 23, No. 6, Jun. 2005, pp. 283-290.

Gurr et al., "Engineering Plants with Increased Disease Resistance: What are we going to express?", Trends Biotechnology, vol. 23, No. 6, Jun. 2005, pp. 275-282.

Hellens et al., "pGreen: A Versatile and Flexible Binary Ti Vector for Agrobacterium-Mediated Plant Transformation", Plant Molecular Biology, vol. 42, 2000, pp. 819-832.

Henikoff et al., "TILLING. Traditional Mutagenesis Meets Functional Genomics", Plant Physiology, vol. 135, Jun. 2004, pp. 630-636.

Holub et al., "Phenotypic and Genotypic Characterization of Interactions between Isolates of Peronospora Parasitica and Accessions of *Arabidopsis thaliana*", vol. 7, No. 2, 1994, pp. 223-239.

Jong et al., "Membrane-Associated Transcripts in *Arabidopsis*; Their Isolation and Characterization by DNA Microarray Analysis and Bioinformatics", The Plant Journal, vol. 46, 2006, pp. 708-721.

Karimi et al., "GATEWAY Vectors for Agrobacterium-Mediated Plant Transformation", Trends in Plant Science, vol. 7, No. 5, May 2002, pp. 193-195.

Kim et al., "Characterization of Late Blight Resistance Derived from Solanum Pimpinellifoliurn L3708 against Multiple Isolates of the Pathogen Phytophthora Infestans", Journal of the American Society for Horticultural Science, vol. 131 No. 5, 2006, pp. 637-645.

Kofoet et al., "Inheritance of Resistance to Downy Mildew (Peronospora Destructor [Berk.] Casp.) from Allium Roylei Stearn in the Backcross Allium Cepa L. × (A. Roylei × A. Cepa)", Plant Breeding, vol. 105, 1990, pp. 144-149.

Kortekamp, A., "Expression Analysis of Defence-Related Genes in Grapevine Leaves after Inoculation with a Host and a Non-Host Pathogen", Plant Physiology and Biochemistry, vol. 44, 2006, pp. 58-67.

Lacomme et al., "Bax-Induced Cell Death in Tobacco is Similar to the Hypersensitive Response", Cell Biology, Proc. Natl. Acad. Sci. U.S.A., vol. 96, No. 14, Jul. 1999, pp. 7956-7961.

Lebeda, A.,"Screening of Wild *Cucumis* Species against Downy Mildew (*Pseudoperonospora cubensis*) Isolates from Cucumbers", Phytoparasitica, vol. 20, No. 3, 1992, pp. 203-210.

Lee et al., "Identification of the Gene Encoding Homoserine Kinase from *Arabidopsis thaliana* and Characterization of the Recombinant Enzyme Derived from the Gene", Archives Biochemistry Biophysics, vol. 372, No. 1, Dec. 1999, pp. 135-142.

Lee et al., "Methionine and Threonine Synthesis are Limited by Homoserine Availability and not the Activity of Omoserine Kinase in *Arabidopsis thaliana*", The Plant Journal, vol. 41, 2005, pp. 685-696.

Mae et al., "Transgenic Plants Producing the Bacterial Pheromone N-Acyl-Homoserine Lactone Exhibit Enhanced Resistance to the Bacterial Phytapathogen Erwinia Carotovora", Molecular Plant-Microbe Interactions, vol. 14, No. 9, 2001, pp. 1035-1042.

McCallum et al., "Targeted Screening for Induced Mutations", Nature Biotechnology, vol. 18, Apr. 2000, pp. 455-457.

Meer et al., "An Interspecific Cross between Allium Roylei Stearn and *Allium cepa* L., and its Backcross to A. Cepa", Euphytica, vol. 47, 1990, pp. 29-31.

Mercedes, Dana et al., "Transgenic Tobacco Plants Overexpressing Chitinases of Fungal Origin Show Enhanced Resistance to Biotic and Abiotic Stress Agents", Plant Physiology, vol. 142, Oct. 2006, pp. 722-730.

Parker et al., "Characterization of eds1, a Mutation in *Arabidopsis* Suppressing Resistance to Peronospora Parasitica Specified by Several Different RPP Genes", Plant Cell, vol. 8, Nov. 1996, pp. 2033-2046.

Perchepied et al., "Relationship Between Loci Conferring Downy Mildew and Powdery Mildew Resistance in Melon Assessed by Quantitative Trait Loci Mapping", Phytopathology, vol. 95, No. 5, 2005, pp. 556-565.

(56) References Cited

OTHER PUBLICATIONS

"Prosecution History of European Patent Application No. 08707413.4" 414 pages.
"Prosecution History of European Patent Application No. 12155885.2" 1335 pages.
"Prosecution History of European Patent Application No. 12155893.6" 1257 pages.
Radwan et al., "Molecular Characterization of Two Types of Resistance in Sunflower to Plasmopara Halstedii, the Causal Agent of Downy Mildew", Phytopathology, vol. 101, No. 8, 2011, pp. 971-979.
Rostas et al., "Copper and Herbivory Lead to Priming and Synergism in Phytohormones and Plant Volatiles in the Absence of Salicylate-Jasmonate Antagonism", Plant Signaling & Behavior, vol. 8, No. 6, Jun. 2013, pp. e24264-1-e24264-3.
Sabetta et al., "SunTILL: A Tilling Resource for Gene Function Analysis in Sunflower", Plant Methods, vol. 7, No. 20, 2011, pp. 1-13.
Sandhu et al., "Soybean Phytophthora Resistance Gene Rps8 Maps Closely to the Rps3 Region", Journal of Heredity, vol. 96, No. 5, Jun. 15, 2005, pp. 536-541.
Sinapidou et al., "Two TIR:NB:LBR Genes are Required to Specify Resistance to Peronospora Parasitica Isolate Cala2 in *Arabidopsis*", The Plant Journal, vol. 38, 2004, pp. 898-909.
Sun, et al., "Silencing of Six Susceptibility Genes Results in Potato Late Blight Resistance", Transgenic Research, vol. 25, 2016, pp. 731-742 (with 12 pages of Supplementary Copy).
Szwacka et al., "Variable Properties of Transgenic Cucumber Plants Containing the Thaumatin II Gene from Thaumatococcus Daniellii", Acta Physioiogiae Plantarum, vol. 24. No. 2, 2002, pp. 173-185.
Takatsuji, Hiroshi, "Development of Disease-Resistant Rice Using Regulatory Components of Induced Disease Resistance", Frontiers in Plant Science, vol. 5, Article 630, Nov. 13, 2014, 12 pages.
Thomas et al., "Linkage of Random Amplified Polymorphic DNA Markers to Downy Mildew Resistance in Cucumber (*Cucumis sativus* L.)", Euphytica, vol. 115, No. 2, 2000, pp. 105-113.
Thomazella et al., "CRISPR-Cas9 Mediated Mutagenesis of a DMR6 Ortholog in Tomato Confers Broad-Spectrum Disease Resistance", Department of Plant and Microbial Biology, University of California, Berkeley, Berkeley CA 94720, Jul. 2016, pp. 1-23.
Till et al., "Mismatch Cleavage by Single-Strand Specific Nucleases", Nucleic Acids Research, vol. 32, No. 8, 2004, pp. 2632-2641.
UNIPROT Database Accession No. K4C928, Available at <http://www.uniprot.org/uniprot/K4C928.txt> Nov. 28, 2012, pages.
UNIPROT Database Accession No. M0ZIQ1, Available at <http://www.uniprot.org/uniprot/M0ZIQ1.txt>, Apr. 3, 2013, 2 pages.
UNIPROT Database Accession No. M1CK41, Avaiiable at < Database Accession No. M1CK41> Apr. 3, 2013, 2 pages.
Vailleau et al., "A R2R3-MYB Gene, AtMYB30, Acts as a Positive Regulator of the Hypersensitive Cell Death Program in Plants in Response to Pathogen Attack", vol. 99, No. 15, Jul. 23, 2002, pp. 10179-10184.
Van Damme et al., "*Arabidopsis* DMR6 Encodes a Putative 2OG-Fe(II) Oxygenase that is Defense-Associated but Required for Susceptibility to Downy Mildew", The Plant Journal, vol. 54, 2008,pp. 785-793.
Van Damme et al., "Downy Mildew Resistance in *Arabidopsis* by Mutation of Homoserine Kinase", The Plant Cell, vol. 21, Jul. 2009, pp. 2179-2189.
Van Schie, Christianus Cornelis Nicolaas., U.S. Appl. No. 15/314,778, status dated Nov. 29, 2016, titled "Phytophthora Resistant Plants Belongings to the Solanaceae Family".
Vandenbussche et al., "Generation of a 3D Indexed Petunia Insertion Database for Reverse Genetics", The Plant Journal, vol. 54, 2008, pp. 1105-1114.
Xun et al., "Genome Sequence and Analysis of the Tuber Crop Potato", Nature, vol. 475, Jul. 14, 2011, p. 189-195.

Yang et al., "Characterization and Mapping of Rpi1, A Gene that Confers Dominant Resistance to Stalk Rot in Maize", Molecular Genetics and Genomics, vol. 274, 2005, pp. 229-234.
Zeilmaker et al., "Downy Mildew Resistant 6 and DMR6-Like Oxygenase 1 are Partially Redundant but Distinct Suppressors of immunity in *Arabidopsis*", The Pant Journal, vol. 81, 2015, pp. 210-222.
Zeilmaker, Tieme, "Functional and Applied Aspects of the Downy Mildew Resistant 1 and 6 Genes in *Arabidopsis*", Universiteit Utrecht, Available at <http://web.science.uu.nl/pmi/publications/PDF/2012/Proefschrift-Zeilmaker-2012.pdf>, Feb. 6, 2012, 147 pages.
Zhang et al., "Salicylic Acid 3-Hydroxylase Regulates *Arabidopsis* Leaf Longevity by Mediating Salicylic Acid Catabolism", Proceedings of the National Academy of Sciences of the United States of America, vol. 110, No. 36, Sep. 3, 2013, pp. 14807-14812.
Zimmermann et al., "Gene-Expression Analysis and Network Discovery using Genevestigator", Trends Plant Sci., vol. 10, No. 9, Sep. 2005, pp. 407-409.
Choi et al., "Predicting the Functional Effect of Amino Acid Substitutions and Indels", PLoS One, vol. 7, No. 10, 2012, pp. 1-13.
Constantinescu et al., "Peronospora-like Fungi (Chromista, Peronosporales) Parasitic on Brassicaceae and Related Hosts", Nova-Hedwigia, vol. 74, May 2002, pp. 291-338.
Flanagan et al., "Using Sift and Polyphen to Predict Loss-of-Function and Gain-of-Function Mutations", Genet Test Mol Biomarkers, vol. 14, No. 4, 2010, pp. 533-537.
Göker et al., "Phylogeny of Hyaloperonospora Based on Nuclear Ribosomal Internal Transcribed Spacer Sequences", Mycological Progres, vol. 3, No. 2, May 2004, pp. 83-94.
Göker et al., "Taxonomic aspects of Peronosporaceae inferred from Bayesian molecular phylogenetics", Canadian Journal of Botany, vol. 81, No. 7, 2003, pp. 672-683.
Guzzo Thesis, "Isolation of cv. Mundo Novo Coffee Plant Genes Associated with Systemic Acquired Resistance", Jun. 2004, 21 pages (10 pages of English Translation and 11 pages of Official Language copy).
Hong et al., "First confirmed report of downy mildew caused by Hyaloperonospora parasitica on broccoli in Korea", Plant Pathology, vol. 57, No. 4, Aug. 2008, p. 777.
Kitz, Leilani, "Evaluation of Downy Mildew (Peronospora farinosa f.sp. chenopodii) Resistance among Quinoa Genotypes and Investigation of P. farinosa Growth using Scanning Electron Microscopy", All Theses and Dissertations, Brigham Young University, 2008, 134 pages.
Ku et al., "Comparing Sequenced Segments of the Tomato and *Arabidopsis* Genomes: Large-Scale Duplication Followed by Selective Gene Loss Creates a Network of Synteny", PNAS, vol. 97, No. 16, Aug. 1, 2000, pp. 9121-9126.
Lamour et al., "Oomycete Genetics and Genomics: Diversity, Interactions and Research Tools", Wiley-Blackwell, 2009, 6 pages.
Prosecution History of European Patent Application No. 12155885. 2, 2017, 404 pages.
Prosecution History of European Patent Application No. 12155893. 6, 2017, 161 pages.
Russell, G. E., "Some Effects of Inoculation With Yellowing Viruses on the Susceptibility of Sugar Beet to Fungal Pathogens: I. Susceptibility to Peronospora Farinosa", Transactions of the British Mycological Society, vol. 49, No. 4, 1966, pp. 611-619.
Sim et al., "SIFT web server: predicting effects of amino acid substitutions on proteins", Nucleic Acids Res., vol. 40, Web Server issue, 2012, 6 pages.
Van Damme, Mirelle, "Genetic Analysis of Disease Susceptibility in the *Arabidopsis*-Hyaloperonospora Parasitica Interaction", Thesis, 2007, 134 pages.
Voglmayr, Hermann, "Phylogenetic Relationships of Peronospora and Related Genera Based on Nuclear Ribosomal Its Sequences", Mycol Res., vol. 107, No. 10, 2003, pp. 1132-1142.
Zhang, James Z., "Overexpression Analysis of Plant Transcription Factors", Curr Opin Plant Biol., vol. 6, No. 5, 2003, pp. 430-440.
Van Damme, "Identification of *Arabidopsis* Loci Required for Susceptibility to the Downy Mildew Pathogen Hyaloperonospora parasitica", MPMI, vol. 18, No. 6, 2005, pp. 583-592.

(56) References Cited

OTHER PUBLICATIONS

Database EMBL [Online], "*Arabidopsis thaliana* flavanone 3-hydroxylase-like protein (At5g24530) mRNA, complete cds", Apr. 15, 2002. Retrieved from EBI accession No. EMBL: AY081455.

Database EMBL [Online], "*Arabidopsis thaliana* flavanone 3-hydroxylase-like protein (K18P6.6) mRNA, complete cds", Jun. 16, 2001. Retrieved from EBI accession No. EMBL: AF386975.

Skadhauge et al., "The role of the barley testa layer and its flavonoid content in resistance to Fusarium infections", Hereditas vol. 126, (1997) pp. 147-160.

Cho et al., "Constitutive expression of the Flavanone 3-hydroxylase gene related to pathotype-specific ascochyta blight resistance in *Cicer arietinum* L.", Physiological and Molecular Plant Pathology, vol. 67 (2005) pp. 100-107.

Ardi et al., "Involvement of epicatechin biosynthesis in the activation of the mechanism of resistance of avocado fruits to Colletotrichum gloeosporioides", Physiological and Molecular Plant Pathology, vol. 53, (1998) pp. 269-285.

Weaver et al., "The *Arabidopsis thaliana* TIR-NB-LRR R-protein, RPP1A; protein localization and constitutive activation of defence by truncated alleles in tobacco and *Arabidopsis*", The Plant Journal, vol. 47, (2006), pp. 829-840.

Tor et al., *Arabidopsis* Downy Mildew Resistance Gene RPP27 Encodes a Receptor-Like Protein Similar to CLAVATA2 and Tomato Cf-9 1, Plant Physiology, vol. 135, (Jun. 2004), pp. 1100-1112.

Mosher et al., "A Comprehensive Structure-Function Analysis of *Arabidopsis* SNI1 Defines Essential Regions and Transcriptional Repressor Activity", The Plant Cell, vol. 18, (Jul. 2006) pp. 1750-1765.

Fig. 1A

```
Arabidopsis              ------MAAKLISTGFRHTTLPENYVRPISDRPRLSEVSQLED-FPLIDL 43
Aquilegia_sp             ------MESSNVLLTGTRHSNLPENYVRSVSDRPRLSEVKDCEN-VPVIDL 44
Citrus_sinensis          ------MDTKVLSSGIRYTNLPEGYVRPESERPNLSEVSECKN-VPVIDL 43
Coffea_canephora         ------METKVISSGIKYTSLPESYVRPESERPRLSEVSDCQN-VPVVDL 43
Cucumis_sativus          --MSSVMEIQLLCSGGRHEKLPEKYERPESDRPRLSEVCCWDK-VPIIDL 47
Gossypium_hirsutum       ------MDTKVLSSGIHYSSLPESYVRPESERPRLSEVSQCDN-VPVIDL 43
Lactuca_sativa           ------MAAKVISSGFRYTTLPESYVRPVNDRPNLSQVSDCND-VPVIDI 43
Medicago_truncatula      ------MDTKVLSSGIHYSKLPESYIRPESDRPCLSQVSEFEN-VPIIDL 43
Oryza_sativa_1           MAAEAEQQHQLLSTAVH-DTMPGKYVRPESQRPRLDLVVSDAR-IPVVDL 48
Oryza_sativa_2           ------MADQLISTADH-DTLPGNYVRPEAQRPRLADVLSDAS-IPVVDL 42
Oryza_sativa_3           -----MATTQLLSTVEHRETLPEGYARPESDRPRLAEVATDSN-IPLIDL 44
Populus_trichocarpa_1    ------MDTKVLSSGIQYTNLPASYVRPESERPRLWEVSTCEN-VPVIDL 43
Populus_trichocarpa_2    ------MDTKVLSSGVHYTNLPASYVRPESERPRLSEVSTCED-VPVIDL 43
Solanum_lycopersicum_1   ------METKVISSGINHSTLPQSYIRPESDRPRLSEVVDCEN-VPIIDL 43
Solanum_lycopersicum_2   -----MTTTSVLSSGFNHSTLPQSYVRPESQRPCMSFVVDSDDLVPVIDM 45
Sorghum_bicolor          ------MAEQLLSTAVH-DTLPGSYVRPESQRPRLAEVVTGAR-IPVVDL 42
Spinacia_oleracea        ------MANKILSTGIPYKTLPESYIRPENERPNLSQVSDCEN-VPVIDL 43
Vitis                    ------MESKVLSTGIRYLTLPQSYIRPEPERPRLSQVSECKH-VPIIDL 43
Zea_mays                 ------MAEHLLSTAVH-DTLPGSYVRPESQRPRLAEVVTGAR-IPVVDL 42
Zingiber_officinale      ------MADMLLSIGEH-DTMPRNYVRPENERPHLDNVIADAN-IPVVDF 42
                                  ::        .:*   * *. :**  :  *     .*::*:

Arabidopsis              S-STDRSFLIQQIHQACARFGFFQVINHGVNKQIIDEMVSVAREFFSMSM 92
Aquilegia_sp             S-VADESLLAQQIGNACKSHGFFQVINHGVNSELVEKMMEISHEFFHLPL 93
Citrus_sinensis          A-CDDRSLIVQQVADACKNYGFFQAINHEVPLETVERVLEVAKEFFNLPV 92
Coffea_canephora         C-FGDRNLMVRQIGDACRDYGFFQVINHGVSKDAVDKMLETATEFFSLPV 92
Cucumis_sativus          G-CEEREMIVKQVEEACKSYGFFQVINHGVRKELVEKVIEVGKQFFELPM 96
Gossypium_hirsutum       G-CEDRSHIVQQIALACINYGFFQVINHGVSKEAVERMLQVAHDFFGLPV 92
Lactuca_sativa           G-CGDRQLISQQTGDACRRYGFFQVINHGVPDEIVEKMQQVGREFFLLPV 92
Medicago_truncatula      G-SHNRTQIVQQIGEACSSYGFFQVVNHGVFLEELKKTAEVAYDFFKLPV 92
Oryza_sativa_1           A-SPDRAAVSAVGDACRTHGFFQVVNHGIDAALIASVMEVGREFFRLPA 97
Oryza_sativa_2           A-NPDRAKLVSQVGAACRSHGFFQVLNHGVFVELTLSVLAVAHDFFRLPA 91
Oryza_sativa_3           A-SPDKPRVIAEIAQACRTYGFFQVTNHGIAEELLEKVMAVALEFFRLPP 93
Populus_trichocarpa_1    G-CQERDQIVQQVGDACKNYGFFQVINHGVSLEAVEKMLGVAHDFFSLPV 92
Populus_trichocarpa_2    G-CQDRNQIVQQVGDACEHYGFFQVINHGVSLEAVEKMLGVAHDFFSLPV 92
Solanum_lycopersicum_1   S-CGDQAQIIRQIGEACQTYGFFQVINHGVPKEVVEKMLGVAGEFFNLPV 92
Solanum_lycopersicum_2   S-CTNRNVIVHQIGEACRLYGFFQVINHGVSKKVIDEMLGVSHEFFKLPV 94
Sorghum_bicolor          G-SPDRAAVVAAIGDACRSHGFFQVLNHGVHADLVAAVMAVGRAFFRLSP 91
Spinacia_oleracea        C-AKDRTQTIHQVFNACKNYGFFQVINHGVSKELAEKMQKVAREFFDMSV 92
Vitis                    CKDVNRAQLIQHIADACRLYGFFQVINHGVAAEMMEKMLEVADEFYRLPV 93
Zea_mays                 G-SPDRGAVVAAVGDACRSHGFFQVVNHGIHAALVAAVMAAGRGFFRLPP 91
Zingiber_officinale      G-APDKSQIISQIEKACRLYGFFQVVNHGIAAELIKKVLAIALEFFRLPQ 91
                           .   ::        :  **  .****. ** :             .  *:  :.
```

Fig. 1B

```
Arabidopsis              EEKMKLYSDDPTKTTRLSTSFNVKKEEVNNWRDYLRLHCYPIHKYVNEWP 142
Aquilegia_sp             DVKMQFYSDDPTKTMRLSTSFNLKKESVHNWRDYLRLHCHPIEKYVQFWP 143
Citrus_sinensis          EEKLKLYSDDPSKTMRLSTSFNVNKEKVHNWRDYLRLHCYPLDKYVPEWP 142
Coffea_canephora         EEKLKLYSDDPSKTTRLSTSFNVKKETVHNWRDYLRLHCYPLEKYVPEWP 142
Cucumis_sativus          EEKLKFYSDDPSKTVRLSTSFNVRKEQFRNWRDYLRLHCYPLSNYTPHWP 146
Gossypium_hirsutum       EEKMKLYSDDPSKTMRLSTSFNVKKEKVHNWRDYLRLHCYPLHKYVPEWP 142
Lactuca_sativa           EEKMKLYSEDPSKTMRLSTSFNVQKEQIHNWRDYLRLHCYPLDQYSPEWP 142
Medicago_truncatula      EEKMKLYSDDPTKTMRLSTSFNVNKEKVHNWRDYLRLHCYPLDNYVPFWP 142
Oryza_sativa_1           EEKAKLYSDDPAKKIRLSTSFNVRKETVHNWRDYLRLHCYPLHQFVPDWP 147
Oryza_sativa_2           EEKAKLYSDDPAKKIRLSTSFNVRKETVHNWRDYLRLHCYPLHRYLPDWP 141
Oryza_sativa_3           EEKEKLYSDEPSKKIRLSTSFNVRKETVHNWRDYLRLHCHPLEEFVPEWP 143
Populus_trichocarpa_1    EEKLKLYSDDPSKTMRLSTSFNVNKEKVHNWRDYLRLHCYPLDKYAPEWP 142
Populus_trichocarpa_2    EEKLKLYSDDPTKTMRLSTSFNVNKEKVHNWRDYLRLHCYPLDKYVPEWP 142
Solanum_lycopersicum_1   EEKLKLYSDDPSKTMRLSTSFNVKKETVHNWRDYLRLHCYPLEKYAPEWP 142
Solanum_lycopersicum_2   EEKMKLYSDDPSKTMRLSTSFNVKKETVHNWRDYLRLHCYPLDKYAPEWP 144
Sorghum_bicolor          EEKAKLYSDDPARKIRLSTSFNVRKETVHNWRDYLRLHCHPLDEFVPDWP 141
Spinacia_oleracea        EEKMKLYSDDPTKTLRLSTSFNVNKEEVHNWRDYLRLHCWPLEQYVPEWP 142
Vitis                    EEKMKLYSDDPTKTMRLSTSFNVNKEKVHNWRDYLRLHCYPLDQYTPEWP 143
Zea_mays                 EEKAKLYSDDPARKIRLSTSFNVRKETVHNWRDYLRLHCHPLDEFLPDWP 141
Zingiber_officinale      EEKAKLYSDDPAKKIRLSTSFNVRKETVHNWRDYLRLHCYPLEEFIPDWP 141
                          : * ::**::*::. *******:.**  ..********** *: .:  .**

Arabidopsis              SNPPSFKEIVSKYSREVREVGFKIEELISESLGLEKDYMKKVLGEQGQHM 192
Aquilegia_sp             SVPSTFKDVVATYCKEVRKLGLRLLGSISLSLGLEEDYIEKVLGDQGQHM 193
Citrus_sinensis          SNPSTFKEFVSTYCSEVRGLGYRVLELISESLGLEKDYIKKVLGEQGQHM 192
Coffea_canephora         SNPPSFKEMVSNYCVQIRELGLRLEEAIAESLGLDKECIKKVLGDQGQHM 192
Cucumis_sativus          SNPPSFREIVSSYCNFVRKVGYRIEFLISESLGLEKEYIRKKLGEQGQHM 196
Gossypium_hirsutum       SNPPSFKQIVSDYCVQVRELGYRLQFLISESLGLEKDYIKKVIGEQGQHM 192
Lactuca_sativa           SNPSYFKEYVGNYCTAVRNLGMRILESISESLGLQKEEIKTILGDQGQHM 192
Medicago_truncatula      SNPPSFKETVANYCKEVRELGLRIEEYISESLGLEKDYLRNALGEQGQHM 192
Oryza_sativa_1           SNPPSFKEIIGTYCTEVRELGFRLYEAISESLGLEGGYMRETLGEQEQHM 197
Oryza_sativa_2           SNPPSFREIISTYCREVRELGFRLYGAISESLGLEQDYIKKVLGEQEQHM 191
Oryza_sativa_3           SNPAQFKEIMSTYCREVRQLGLRLLGAISVSLGFEEDYIEKVLGEQEQHM 193
Populus_trichocarpa_1    SKPPPFKDIVSSYCIQVRELGFRIQELISESLGLEKDHVKNVLGEQGQHM 192
Populus_trichocarpa_2    SNPPPFKEIVRSYSIQVRELGFRIQELISESLGLEKDHIKNVLGEQGQHM 192
Solanum_lycopersicum_1   SNPSSFREIVSRYCREIRQLGFRLEEAIAESLGLDKECIKDVLGEQGQHM 192
Solanum_lycopersicum_2   SNPPSFREIVSKYCMEVRELGYRLEEAISESLGLEKDCIKNVLGEQGQHM 194
Sorghum_bicolor          SNPPDFKDTMSTYCKEVRELGFRLYAAISESLCLEASYMKETLGEQEQHM 191
Spinacia_oleracea        SNPPSFKEIVSKYIKEVRELGFRVQELISESLGLEKDYIKNVLCDQGQHM 192
Vitis                    SNPPSFKEIVSSYCKEVRELGFRLQEMISESLGLEKDHIKNVFGEQGQHM 193
Zea_mays                 SNPPDFKETMGTYCKEVRELGFRLYAAISESLGLEASYMKEALGEQEQHM 191
Zingiber_officinale      SNPSSFKDVFGSYCQQVRKLGFRILGIISLSLGLEEEYLVRVLGEQEQHM 191
                          * *. *::  . *    :* :* ::       *: ****:  :  :*:* ***

Arabidopsis              AVNYYPPCPEPELTYGLPAHTDPNALTILLQDTTVCGLQILI-DGQWFAV 241
Aquilegia_sp             AVNYYPPCPEPELTYGLPRHTDPNTITILLQGQEVAGLQVLH-NGKWVAV 242
Citrus_sinensis          AVNFYPPCPEPELTYGLPGHTDPNALTILLQDLEVAGLQVLR-DDKWVAV 241
Coffea_canephora         AVNYYPPCPQPDLTYGLPGHTDPNALTILLQDLNVAGLQVLR-DGRWLAV 241
Cucumis_sativus          AINYYPPCPQPELTYGLPGHTDPNALTILLQDLHVAGLQVLK-DGKWIAV 245
Gossypium_hirsutum       AVNYYPPCPEPELTYGLPGHTDPNALTILLQDLQVAGLQVLK-DSKWLAV 241
Lactuca_sativa           AINHYPVCPEPELTYGLPGHTDPNALTILLQDTLVSGLQVLK-DGKWLAV 241
Medicago_truncatula      AVNYYPPCPQPELTYGLPGHTDPNALTILLQDLHVAGLQVLK-DGKWLAI 241
Oryza_sativa_1           AVNYYPQCPEPELTYGLPAHTDPNALTILLMDDQVAGLQVLNDG-KWIAV 246
Oryza_sativa_2           AVNFYPKCPFPELTFGLPAHTDPNALTILLMDQQVAGLQVLKEG-RWIAV 240
Oryza_sativa_3           AVNYYPRCPEPDLTYGLPKHTDPNALTILLPDPHVAGLQVLRDGDQWIVV 243
Populus_trichocarpa_1    AVNFYPPCPEPELTFGLPGHTDPNALTILLQDQSVAGLQVLK-DGKWVAV 241
Populus_trichocarpa_2    AVNFYPCPEPELTYGLPAHTDPNALTILLQDLSVAGLQVLLKDGKWVAV 242
Solanum_lycopersicum_1   AINYYPCPQPELTYGLPAHTDPNSLTILLQDLQVAGLQVLK-DGKWLAV 241
```

Fig. 1C

```
Solanum_lycopersicum_2    AINFYPQCPQPELTYGLPAHTDPNAITILLQDLQVAGLQVLK-DGKWLSI 243
Sorghum bicolor           AVNFYPPCPEPELTYGLPAHTDPNALTILLMDQDVAGLQVLHGG-KWVAV 240
Spinacia_oleracea         ALNYYPECPEPEMTYGLPGHTDPNALTILLQDLQVSGLQIFK-DGKWLAV 241
Vitis                     AVNYYPPCPQPELTYGLPGHTDPNALTILLQDLRVAGLQVLK-DGTWLAI 242
Zea_mays                  AVNFYPPCPEPELTYGLPAHTDPNALTILLMDPDVAGLQVLHAG-QWVAV 240
Zingiber officinale       AVNYYPKCPEPELTYGLPAHTDPNALTILLQDPHVSGLQVHKDG-KWIAV 240
                          *:*.** **:*:;*:*** ****:;**** . *.***:  . *.  :

Arabidopsis               NPHPDAFVINIGDQLQALSNGVYKSVWHRAVTNTENPRLSVASFLCPADC 291
Aquilegia sp              NPYPNAFVVNIGDQIQALSNGNYASVWHRATVNTDRERISVASFLCPAND 292
Citrus_sinensis           NPLPNAFVINIGDQLQALSNGRYKSVWHRAIVNAEKARMSVASFLCPNND 291
Coffea canephora          KPHPDAFVVNIGDQLQALSNGIYKSVWHRAVVNADQFRLSVASFLCPCDH 291
Cucumis_sativus           NPHPNAFVINIGDQLQALSNGVYKSVWHRAVVNVDKPRLSVASFLCPCDD 295
Gossypium_hirsutum        NPQTNAFVINIGDQLQALSNGTYKSVWHRAIVNTDKPRMSVASFLCPYDH 291
Lactuca_sativa            KPHPNAFVINIGDQLEAVSNGEYKSVWHRAVVNSDNPRMSIASFLCPCND 291
Medicago truncatula       NPIPDAFVINIGDQLQALSNGLYKSVWHRAIVNAEKPRLSVASFLCPDNE 291
Oryza_sativa_1            NPQPGALVINIGDQLQALSNGKYRSVWHRAVVNSDRERMSVASFLCPCNS 296
Oryza_sativa_2            NPQPNALVINIGDQLQALSNGRYKSVWHRAVVNSDKARMSVASFLCPCND 290
Oryza_sativa_3            NPRPNALVVNLGDQIQALSNDAYKSVWHRAVVNPVQERMSVASFMCPCNS 293
Populus trichocarpa 1     DPHPDAFVINIGDQLQALSNGRYKSVWHRAITNTDKARMSVASFLCPYDN 291
Populus_trichocarpa_2     NPHPDAFVINIGDQLQALSNGRYKSVWHRAITNTDKARMSVASFLCPFDN 292
Solanum lycopersicum 1    KPQPDAFVINLGDQLQAVSNGKYRSVWHRAVVNSDQARMSVASFLCPCDS 291
Solanum_lycopersicum_2    KPQPNAFVINLGDQLEALSNGKYKSIWHRAIVNSDKARMSVASFLCPNDC 293
Sorghum_bicolor           NPQPGALIINIGDQLQALSNGQYRSVWHRAVVNSDRERMSVASFLCPCNH 290
Spinacia_oleracea         KPQPDAFVINIGDQLQALSNGIYKSVWHRAVVNTDKPRLSVASFLCPAND 291
Vitis                     KPHPGAFVVNIGDQLQAVSNGKYKSVWHRAVVNAESERLSVASFLCPCND 292
Zea_mays                  NPQPGALIINIGDQLQALSNGQYRSVWHRAVVNSDRERMSVASFLCPCNH 290
Zingiber officinale       DPKPNAFVINIGDQLQALSNGRYKSVWHRAVVNSNKERMSVASFLCPCNS 290
                          .*  ..*:::*:***::*:**. * *:****  .*   *:*:***:** :

Arabidopsis               AVMSPAKPLWEAEDDETKFVYKDFTYAEYYKKFWSRNLDQEHCLENFLNN 341
Aquilegia sp              AIICPA---VKDG---SPSMYKKFTYDEYYKKFWSGNLDQQHCLELFKE- 335
Citrus_sinensis           AMISPPKALTEDG---SGAVYRDFTYAEYYSKFWSRNLDQEHCLELFKN- 337
Coffea canephora          AVISAPKPLTADG---SPVVYRDFTYAQYYKKFWSRNLDQQHCLELFKN- 337
Cucumis_sativus           ALITPAPLLSQ-----PSPIYRPFTYAQYYNTFWSRNLDQQHCLELFKNH 340
Gossypium_hirsutum        ALISPAKPFLTQHG---CGAVYRDFTYAEYYSKFWGRNLDQEHCLELFKN- 337
Lactuca_sativa            TVIRAPKFIIKEG---SKPVFKEFTYAEYYAKFWTRNLDQEHCLEFFKN- 337
Medicago truncatula       ALICPAKPLTEDG---SGAVYRGFTYPEYYSKFWSRDLEKEHCLEFFKNN 338
Oryza_sativa_1            VELGPAKKLITDD---SPAVYRNYTYDEYYKKFWSRNLDQEHCLELFRT- 342
Oryza_sativa_2            VLIGPAQKLITDG---SPAVYRNYTYDEYYKKFWSRNLDQEHCLELFRTT 337
Oryza_sativa_3            AVISPARKLVADG---DAPVYRSFTYDEYYKKFWSRNLDQEHCLELFKGQ 340
Populus trichocarpa 1     ALITPPKALTDDG---TGAVYRDFTYAEYYKKFWSRDLDQEHCLELFKNK 338
Populus_trichocarpa_2     ALITPPKALTDDG---TGAIYRDFTYAEYYKKFWSRNLDQEHCLELFKN- 338
Solanum lycopersicum 1    AKISAPKLLTEDG---SPVIYQDFTYAEYYNKFWSRNLDQQHCLELFKN- 337
Solanum_lycopersicum_2    SIISAPKTLTEDG---SSAIYRHFTYAEYYEKFWSRNLDQEYCLELFKND 340
Sorghum bicolor           VVLGPAKKLVTED---TPAVYRSYTYDEYYKKFWSRNLDQEHCLELFRT- 336
Spinacia_oleracea         ALISAPTPLTANG---SPAVYRDYTYPEYYKTFWSRNLDQEHCLELFKNQ 338
Vitis                     AVIGPAKPLTEDG---SAPIYKNFTYAEYYKKFWGRDLDQEHCLELFKN- 338
Zea_mays                  VVLGPARKLVTED---TPAVYRNYTYDKYYAKFWSRNLDQEHCLELFRT- 336
Zingiber officinale       VLISPPEKLIADG---CPAVYRSYTYDEYYKKFWSRNLDQEHCLELFKKE 337
                          :  ..  :         :::  :** :** .**   :*:::***  *
```

Fig. 1D

```
Arabidopsis              ---------
Aquilegia_sp             ---------
Citrus_sinensis          ---------
Coffea_canephora         ---------
Cucumis_sativus          PP------- 342
Gossypium_hirsutum       ---------
Lactuca_sativa           ---------
Medicago_truncatula      ---------
Oryza_sativa_1           ---------
Oryza_sativa_2           PTDTS---- 342
Oryza_sativa_3           ---------
Populus_trichocarpa_1    ---------
Populus_trichocarpa_2    ---------
Solanum_lycopersicum_1   ---------
Solanum_lycopersicum_2   GT------- 342
Sorghum_bicolor          ---------
Spinacia_oleracea        T-------- 339
Vitis                    ---------
Zea_mays                 ---------
Zingiber_officinale      RETCPDAPT 346
```

Fig. 2

```
>Arabidopsis thaliana DMR6 CDS (gi 42568064, Genbank NM_122361)
ATGGCGGCAAAGCTGATATCCACCGGTTTCCGTCATACTACTTTGCCGGAAAACTATGTCCGGCCAATCT
CCGACCGTCCACGTCTCTCTGAAGTCTCTCAACTCGAAGATTTCCCTCTCATCGATCTCTCTTCCACTGA
TCGATCTTTTCTCATCCAACAAATCCACCAAGCTTGTGCCCGATTCGGATTTTTTCAGGTCATAAATCAC
GGAGTTAACAAACAAATAATAGATGAGATGGTGAGTGTTGCGCGTGAGTTCTTTAGCATGTCTATGGAAG
AAAAAATGAAGCTATATTCAGACGATCCAACGAAGACAACAAGATTATCGACGAGCTTCAATGTGAAGAA
AGAAGAAGTCAACAATTGGAGAGACTATCTAAGACTCCATTGTTATCCTATCCACAAGTATGTCAATGAG
TGGCCGTCAAACCCTCCTTCTTTCAAGGAAATAGTAAGTAAATACAGTAGAGAAGTAAGAGAAGTGGGAT
TTAAAATAGAGGAATTAATATCAGAGAGCTTAGGTTTAGAAAAAGATTACATGAAGAAAGTGCTTGGTGA
ACAAGGTCAACACATGGCAGTCAACTATTATCCTCCATGTCCTGAACCTGAGCTCACTTACGGTTTACCT
GCTCATACCGACCCAAACGCCCTAACCATTCTTCTTCAAGACACTACTGTTTGCGGTCTCCAGATCTTGA
TCGACGGTCAGTGGTTCGCCGTTAATCCACATCCTGATGCTTTTGTCATCAACATAGGTGACCAGTTACA
GGCATTAAGTAATGGAGTATACAAAAGTGTTTGGCATCGCGCTGTAACAAACACAGAAAATCCGAGACTA
TCGGTCGCATCGTTTCTGTGCCCAGCTGACTGTGCTGTCATGAGCCCGGCCAAGCCCTTGTGGGAAGCTG
AGGACGATGAAACGAAACCAGTCTACAAAGATTTCACTTATGCAGAGTATTACAAGAAGTTTTGGAGTAG
GAATCTGGACCAAGAACATTGCCTCGAGAATTTTCTAAACAACTAA > Arabidopsis thaliana DMR6 protein (gi 15238567, Genbank NP_197841)
MAAKLISTGFRHTTLPENYVRPISDRPRLSEVSQLEDFPLIDLSSTDRSFLIQQIHQACARFGFFQVINH
GVNKQIIDEMVSVAREFFSMSMEEKMKLYSDDPTKTTRLSTSFNVKKEEVNNWRDYLRLHCYPIHKYVNE
WPSNPPSFKEIVSKYSREVREVGFKIEELISESLGLEKDYMKKVLGEQGQHMAVNYYPPCPEPELTYGLP
AHTDPNALTILLQDTTVCGLQILIDGQWFAVNPHPDAFVINIGDQLQALSNGVYKSVWHRAVTNTENPRL
SVASFLCPADCAVMSPAKPLWEAEDDETKPVYKDFTYAEYYKKFWSRNLDQEHCLENFLNN*
```

Fig. 3

```
>Lactuca sativa DMR6 ortholog CDS
ATGGCCGCAAAAGTCATCTCCAGTGGATTCCGGTATACTACTCTACCGGAGAGCTACGTCCGTCCGGTTAA
CGACAGACCTAACCTATCTCAAGTTTCCGATTGCAACGACGTTCCTGTTATTGACATCGGTTGTGGTGATA
GACAACTCATAAGCCAACAAATTGGCGATGCTTGTAGAAGATACGGTTTTTTCCAGGTGATTAATCATGGT
GTGCCTGATGAAATAGTGGAGAAAATGCAACAAGTAGGTAGGGAGTTTTTCCTGTTGCCTGTGGAAGAGAA
GATGAAGCTTTACTCAGAGGATCCATCGAAGACGATGAGGCTATCCACCAGCTTTAACGTCCAAAAGAAC
AAATTCATAACTGGCCAGATTATCTCCGCCTTCACTGTTATCCTCTGGATCAATACAGTCCTGAATGGCCT
TCAAATCCTTCTTATTTCAAGGAATATGTTGGTAATTATTGTACAGCAGTGCGAAATTTAGGAATGAGAAT
ATTAGAATCAATATCAGAAAGTTTAGGGTTACAAAAAGAAGAAATAAAAACTATATTAGGCGATCAAGGTC
AACACATGGCCATCAACCATTACCCAGTGTGCCCTGAGCCCGAGCTAACCTACGGGCTACCCGGGCACACA
GACCCCAATGCTCTCACCATCCTTCTACAGGACACACTGGTCTCTGGTCTTCAGGTTCTCAAAGATGGCAA
ATGGTTAGCCGTTAAACCACACCCTAATGCGTTTGTAATTAACATTGGTGATCAGTTAGAGGCGGTGAGTA
ATGGTGAATATAAAAGTGTATGGCATCGAGCTGTGGTTAACTCAGACAACCCGCGAATGTCTATAGCTTCG
TTTTTGTGTCCTTGTAATGACACCGTTATTAGGGCTCCTAAAGAAATAATAAAGGAAGGATCGAAACCTGT
TTTCAAAGAATTTACTTATGCAGAATACTACGCGAAGTTTTGGACAAGAAACCTTGATCAAGAACATTGCT
TAGAATTCTTCAAGAACTAC >Lactuca sativa DMR6 ortholog protein
MAAKVISSGFRYTTLPESYVRPVNDRPNLSQVSDCNDVPVIDIGCGDRQLISQQIGDACRRYGFFQVINHG
VPDEIVEKMQQVGREFFLLPVEEKMKLYSEDPSKTMRLSTSFNVQKEQIHNWRDYLRLHCYPLDQYSPEWP
SNPSYFKEYVGNYCTAVRNLGMRILESISESLGLQKEEIKTILGDQGQHMAINHYPVCPEPELTYGLPGHT
DPNALTILLQDTLVSGLQVLKDGKWLAVKPHPNAFVINIGDQLEAVSNGEYKSVWHRAVVNSDNPRMSIAS
FLCPCNDTVIRAPKEIIKEGSKPVFKEFTYAEYYAKFWTRNLDQEHCLEFFKN*
```

Fig. 4

```
>Spinacia oleracea DMR6 ortholog CDS
ATGGCAAACAAGATATTATCCACCGGAATTCCTTACAAAACCCTCCCCGAAAGCTACATCCGACCCGAAAA
TGAGAGGCCCAACTTATCTCAAGTCTCCGATTGCCAGAATGTCCCTGTTATTGACTTGGGTGCCAAAGACC
GTACTCAAACAATCCACCAAGTCTTCAATGCTTGTAAAAATTACGGGTTTTTCCAGGTGATTAATCATGGG
GTGTCAAAGGAATTAGCGGAGAAGATGCAAAAGGTAGCTCGAGAGTTCTTCGATATGTCGGTTGAGGAAAA
AATGAAATTATATAGTGACGATCCAACTAAAACACTAAGATTGTCTACAAGTTTTAACGTTAACAAAGAGG
AAGTTCATAATTGGAGAGATTATCTTAGGCTCCATTGTTGGCCTCTTGAGCAATATGTCCCCCAATGGCCT
TCTAACCCCCCTTCCTTCAAGGAAATAGTGAGCAAGTACATAAAAGAAGTTAGGGAACTTGGTTTCAGAGT
CCAAGAACTAATATCAGAGAGTTTAGGGTTGGAGAAAGATTACATAAAGAATGTCCTAGGAGATCAAGGAC
AACACATGGCTCTTAATTATTACCCTGAGTGCCCGGAGCCAGAGATGACATACGGGTTGCCGGGTCATACT
GACCCTAATGCCCTTACCATCCTTCTCCAAGACTTGCAAGTATCTGGCCTTCAAATTTTTAAGGATGGTAA
ATGGCTTGCTGTCAAACCTCAACCTGATGCTTTTGTCATTAACATTGGTGATCAATTGCAGGCATTAAGTA
ACGGTATATACAAGAGTGTATGGCACAGAGCAGTTGTGAACACAGATAAGCCAAGATTATCAGTAGCTTCA
TTCCTCTGCCCCGCCAATGATGCGTTGATAAGCGCGCCAACACCTCTGACCGCCAACGGATCACCGGCTGT
ATATAGACACTATACGTATCCTGAGTACTACAAGACTTTCTGGAGTAGCAACTTGGACCAAGAGCACTGCT
TGGAGCTTTTTAAAAACCAAACCTAG >Spinacia oleracea DMR6 ortholog protein
MANKILSTGIPYKTLPESYIRPENERPNLSQVSDCENVPVIDLGAKDRTQTIHQVFNACKNYGFFQVINHG
VSKELAEKMQKVAREFFDMSVEEKMKLYSDDPTKTLRLSTSFNVNKEEVHNWRDYLRLHCWPLEQYVPEWP
SNPPSFKEIVSKYIKEVRELGFRVQELISESLGLEKDYIKNVLGDQGQHMALNYYPECPEPEMTYGLPGHT
DPNALTILLQDLQVSGLQIFKDGKWLAVKPQPDAFVINIGDQLQALSNGIYKSVWHRAVVNTDKPRLSVAS
       FLCPANDALISAPTPLTANGSPAVYRDYTYPEYYKTFWSRNLDQEHCLELFKNQT*
```

Fig. 5

```
>Cucumis sativus DMR6 ortholog CDS
ATGAGCAGTGTGATGGAGATCCAACTTTTGTGTTCAGGGGGACGTCACGAGAAGTTGCCAGAGAAGTATGA
ACGGCCTGAATCGGATAGGCCGCGGCTGTCGGAGGTGTGTTGTTGGGACAAGGTTCCAATAATCGACTTGG
GATGCGAGGAGAGAGAGATGATTGTGAAGCAAGTGGAGGAGGCCTGCAAGTCTTACGGCTTTTTCCAGGTT
ATAAATCATGGTGTGAGGAAGGAATTGGTGGAGAAAGTGATAGAAGTTGGCAAGCAGTTCTTTGAGCTGCC
GATGGAGGAGAAGTTGAAATTTTATTCAGACGACCCTTCCAAGACCGTCAGACTCTCCACAAGTTTCAATG
TCCGGAAAGAGCAATTTCGCAACTGGAGGGATTATCTCAGACTCCATTGCTATCCTCTCTCCAACTACACC
CCCCATTGGCCCTCTAACCCACCATCCTTCAGGGAAATAGTGAGTAGTTATTGCAATGAAGTACGAAAAGT
TGGGTACAGAATAGAGGAGCTAATATCGGAGAGCTTGGGGCTGGAGAAGGAATACATAAGGAAGAAGTTGG
GTGAACAAGGTCAGCACATGGCTATAAATTATTATCCGCCATGTCCCCAACCAGAACTCACCTACGGGCTC
CCTGGCCATACGGATCCCAACGCACTCACCATTCTCCTTCAGGATCTCCATGTCGCCGGCCTCCAAGTCCT
CAAAGATGGAAAGTGGCTAGCGGTCAACCCCCACCCCAATGCCTTGTAATCAATATAGGCGACCAATTGC
AGGCATTGAGCAATGGGGTGTACAAGAGCGTTTGGCACCGAGCGGTGGTCAATGTTGATAAGCCCAGGCTG
TCGGTCGCTTCTTTTCTCTCCCCTTGTGATGACGCCCTCATTACTCCTGCACCGCTCCTCTCCCAGCCTTC
CCCCATTTACAGACCTTTCACCTACGCCCAGTACTACAATACTTTTTGGAGCAGAAACTTGGATCAACAAC
ATTGCTTGGAACTATTTAAAAACCACCCTCCTTAA >Cucumis sativus DMR6 ortholog protein
MSSVMEIQLLCSGGRHEKLPEKYERPESDRPRLSEVCCWDKVPIIDLGCEEREMIVKQVEEACKSYGFFQV
INHGVRKELVEKVIEVGKQFFELPMEEKLKFYSDDPSKTVRLSTSFNVRKEQFRNWRDYLRLHCYPLSNYT
PHWPSNPPSFREIVSSYCNEVRKVGYRIEELISESLGLEKEYIRKKLGEQGQHMAINYYPPCPQPELTYGL
PGHTDPNALTILLQDLHVAGLQVLKDGKWLAVNPHPNAFVINIGDQLQALSNGVYKSVWHRAVVNVDKPRL
SVASFLCPCDDALITPAPLLSQPSPIYRPFTYAQYYNTFWSRNLDQQHCLELFKNHPP*
```

Fig. 11

```
cattttctataaatccaactaacatctactt
cttaaatctataaccctaacacttttaaactcaaaccgatatataatttgttttaatttaaatctaagtgacttattataaaaccaaa
cctaaaaataatttcgttttatatgtaaattaaactctaatttataattctaaactgacttatatatttgttaattgtaaaatctaattta
aatataattaatcttgttaattaaaagtatacagatttgttatattagtttattatatataactagtataatactagttaaattaaaagtaagagttt
attcttagaggtaaatgcaagtattgtccgtcaattcaagtagtgcacaagagtccatgagtgtccttatcaagattgacctgtgatt
taaaaaggaaaaaatcaacaagatattaattagaacactccacataagaagtgtgagacatcgatcgtgcaccaatgtccacaatggcacccactcaggatttttgatagaatacgagacgtggtttcttgacacgtgcct
gtctgaagtccaaccatgatggcaccactccacataagaagtgtgagacatcgatcgtgcccgtatttggagagaatacgagacgtggtttcttgacacgtgcct
gctttatcctcctgcgcccaaaaatccacaatgtcttatctcaacacgtgttctgcttatccaacctcacacttttcttttgtaccaaataacat
ttgcatgaagattttcttaattatacaactcacattcatgatttaaattcgatttttagttcaagaaaaatcattcttttgatggtacttgtctta
tttaacaggtttgtatatttgtattcatgtttctgccaaatgaaataaaaatgatgttcatgttttaaataaaagtactaaagataacaatcacga
caaattctgcctgtctagtcattaaatatttaacatcaacgatttcaaaactctaaaagatttcagttttcaacataaaacaagtttcgttctcaaatagttctaaatctcaaataggtaaaatatgaatataaa
atgtgtttaagacgcatctagatattttttaataaaaacgagatacattttaataacttataatctatctcctaattataacttatatataactacctaaatgttacataa
tctaccaatttaactctatgtaaaataaaactgatttagtaaacattaagcagtacagaatgctagcgtagcgtatctaaatctaatccacttc
tgaatatttgtttttaactaataaaatcaacaaaataatagtatatgttacaatgaaataatcaatataacgatccaaactaa
aaaaaaaccaaattatataatacaagatattagttattatgttacaatgaaataatcaaatataagatttcttattttaaacgacaacaattaaaaat
atcaagaaccgaatggcttcccaaaccgagatttgaattttatggtcgggattcgtatgtgcgatttcactgagaatagctatcaacaacaatttaaaata
cattgctagatcgtgcggttgttgcggttgttgcgttcactagaacatcaagaaaaaaacaagtccaggtcaggaacaggaagaaggtcaagatagtaatcaagcccttgttcgtc
tattgtacgttagtgtcacttatgataatgttcattcgtataatgttcatcgtaatgtttcatcgtaatcaatgcagttattaataattcatgaatgcagttattaataatcttttctctccgaagtcgacgaacaataaaaaaaacca
aaaaataattatttattactgtcatcgtatgatgctgagctgacacagtcgtaagcctggacaatcatcatgacgtcactgctgtgacgctagaat
atctcattcgaagtacttattactgtcatcgtatgatgctgagctgacacagtcgtaaaaaataatgaaaatgagagcttcagtatttcgatttttcgtttattgtaaacta
catgacattatatcatgtttttgtctgaatttttgtctgaatttcgtaatttaattcgtaatttctgacattttctaaaataataatctattctgactttctaaaaatcgaaaaatcgaaatatctttgtagatgcttaag
gctgaatctgaatcttgagcagttaataagatggttagagtatcttaaagttagtatcttaaagttaggattcttaaaacctatttgttttcagatgttttaagaaaatgaaaattacttttgtggttaattgtttctgtttga
gtaattcttttttaataaataagatggttagagtatcttaaagttagattaaaaactattgttttcagatgttttcagatgttatttcagatgttttcagatgttccattctta
agtatgtgttagatttcttatgaaatttagattaaaaactattgttttcagatgttatttcagatgttatttcagatgttttaattgaatttgttgttattgtccaaaaatatttatttgtttttgttatgaatt
catacctaataagaaaaattagaaatagaaatattaactaagttgtggattcaccgaagctaattcacctaatgcaagctaaacaatttaaactaagtattattagcttaattgataaaagatatttaagataacatatag
ttggttaaagagattacaaacattaaccaaattaaccaaatgagaaatagataaaacactaaagaaagctcctagtatttaaaaaaacactttaaaaaaacacttaattttttatcat
aaatcttaaaacccacagtcgtccttcgaaaatccactatattcggttgataagaatcaaaatccattcgaaatacctatataaacaa
aacaattcacttgaaatcaatcaatccagctcgctctctctatacccttctctatcctcttatctctatcctctataacccttttgattcttctcaaccgcatgcaatgcatcgatgcacatcgcatacataatactcca
agtcgagccttcctcctcctttatctctatcctcttatctctatcctctataacccttttgattcttctcaaccgcatgcaatgcatcgatgcacatcgcatacataatactcca
```

Fig. 12

```
>Solanum lycopersicum DMR6 ortholog CDS
ATGGAAACCAAAGTTATTTCTAGCGGAATCAACCACTCTACTCTTCCTCAAAGTTACATCCG
ACCCGAATCCGATAGACCACGTCTATCGGAAGTGGTCGATTGTGAAAATGTTCCAATAATTG
ACTTAAGTTGCGGAGATCAAGCTCAAATAATTCGTCAAATTGGAGAAGCTTGTCAAACTTAT
GGTTTCTTTCAGGTAATTAATCATGGTGTACCAAAGGAAGTTGTAGAGAAAATGCTAGGGGT
AGCTGGGGAATTTTTCAATTTACCAGTAGAAGAGAAACTAAAATTATATTCAGATGATCCTT
CAAAGACCATGAGATTATCAACAAGTTTTAATGTTAAAAAGGAGACAGTTCATAATTGGAGA
GATTATCTCAGACTTCATTGTTATCCTCTAGAGAAGTATGCTCCTGAATGGCCTTCTAATCC
ATCATCTTTCAGGGAAATCGTGAGCAGATATTGCAGGGAAATTCGTCAACTCGGATTTAGAT
TAGAAGAAGCCATAGCAGAAAGCCTGGGGTTAGATAAAGAGTGTATAAAAGATGTATTGGGT
GAACAAGGACAACATATGGCTATCAATTATTATCCTCCTTGTCCACAACCAGAACTTACTTA
TGGGCTTCCGGCCCATACTGATCCAAATTCACTTACAATTCTTCTTCAAGACTTGCAAGTTG
CGGGTCTTCAAGTTCTTAAAGATGGCAAATGGTTAGCTGTAAAACCTCAACCTGACGCCTTT
GTCATTAATCTTGGGGATCAATTGCAGGCAGTAAGTAACGGTAAGTACAGAAGTGTATGGCA
TCGAGCTATTGTGAATTCAGATCAAGCTAGGATGTCAGTGGCTTCGTTTCTATGTCCGTGTG
ATAGCGCGAAAATCAGTGCACCAAAGCTGCTGACAGAAGATGGATCTCCAGTGATTTATCAA
GACTTTACGTATGCTGAGTATTACAACAAG
TTCTGGAGCAGGAATTTGGACCAGCAACATTGTTTGGAACTTTTCAAGAATAA >Solanum lycopersicum DMR6 ortholog protein
METKVISSGINHSTLPQSYIRPESDRPRLSEVVDCENVPIIDLSCGDQAQIIRQIGEACQTY
GFFQVINHGVPKEVVEKMLGVAGEFFNLPVEEKLKLYSDDPSKTMRLSTSFNVKKETVHNWR
DYLRLHCYPLEKYAPEWPSNPSSFREIVSRYCREIRQLGFRLEEAIAESLGLDKECIKDVLG
EQGQHMAINYYPPCPQPELTYGLPAHTDPNSLTILLQDLQVAGLQVLKDGKWLAVKPQPDAF
VINLGDQLQAVSNGKYRSVWHRAIVNSDQARMSVASFLCPCDSAKISAPKLLTEDGSPVIYQ
DFTYAEYYNKFWSRNLDQQHCLELFKN.
```

Fig. 13

>Nicotiana benthamiana DMR6 ortholog CDS
ATGGAAGCAAAAGTTCTTTCCAGCGGAATCCGCCACTCTACTATCCCTCAAAGTTACATCCG
CCCTCAATCCGATAGGCCGCGCCTTTCTGAAGTTGCTGATTGTGAAAACGTTCCAGTAGTTG
ATATAGGTTGCGGTGATAGAAACCTTATTGTTCATCAAATTGGTGAAGCCTGTCGTCTTTAT
GGTTTTTTCCAGGTAATTAATCATGGTGTACCAAAGAATTTAATAGACGAAATGCTAGAGAT
AGCTGGGGAATTTTTTAGGCTTCCAGTTGAAGAGAAGTTGAAATTGTACTCAGATGACCCAT
CGAAGACGATGAGATTGTCGACTAGTTTTAATGTGAAAAAGGAGAAGGTTCACAATTGGAGA
GATTATCTCAGACTTCATTGTTATCCTCTTGAAAATTACGCTCCTGAATGGCCTTCCAATCC
TTCCTCTTTCAGGGAAATCGTGAGCAGATATTGCATGGAAGTTCGACAACTCGGGTTCAGAT
TGCAGGAAGCCATAGCAGAGAGCCTAGGCTTAGAGAAAGAGTGTATAAAGGATGTATTGGGC
GAACAAGGTCAACACATGGCTATCAATTTCTATCCTCCTTGTCCACAACCAGAACTCACTTA
TGGGCTGCCAGCACATACTGATCCAAATGCCCTTACAATTCTTCTTCAAGACTTAGAAGTAG
CTGGTCTTCAAGTTCTTAAAGATGGCGAATGGTTGGCCGTCAAGCCTCAACCAGATGCCTTT
GTCATTAATCTTGGTGATCAACTGCAGGCAGTGAGTAATGGGAGATACAAAGCGTATGGCA
TCGAGCTATTGTAAATTCAGACAAAGCCAGGTTGTCAGTGGCTTCGTTCCTTTGTCCGTGCG
ATAGCGCGAAAATCAGTGCTCCAAAGCTCCTCACTGAAGATGGATCTCCTGTCATTTATCAG
GACTTTACCTATGCTGAGTATTACAAAAAGTTCTGGAGCAGGAATTTGGACCAGGAACATTG
TTTGGAACTTTTCAAGAACTAA >Nicotiana benthamiana DMR6 ortholog protein
MEAKVLSSGIRHSTIPQSYIRPQSDRPRLSEVADCENVPVVDIGCGDRNLIVHQIGEACRLY
GFFQVINHGVPKNLIDEMLEIAGEFFRLPVEEKLKLYSDDPSKTMRLSTSFNVKKEKVHNWR
DYLRLHCYPLENYAPEWPSNPSSFREIVSRYCMEVRQLGFRLQEAIAESLGLEKECIKDVLG
EQGQHMAINFYPPCPQPELTYGLPAHTDPNALTILLQDLEVAGLQVLKDGEWLAVKPQPDAF
VINLGDQLQAVSNGRYKSVWHRAIVNSDKARLSVASFLCPCDSAKISAPKLLTEDGSPVIYQ
DFTYAEYYKKFWSRNLDQEHCLELFKN.

SEQUENCE LISTING

<160> NUMBER OF SEQ ID NOS: 111

<210> SEQ ID NO 1
<211> LENGTH: 33
<212> TYPE: DNA
<213> ORGANISM: Artificial
<220> FEATURE:
<223> OTHER INFORMATION: forward primer

<400> SEQUENCE: 1
ttctgggatc caatggcggc aaagcttgat atc         33

<210> SEQ ID NO 2
<211> LENGTH: 39

```
<212> TYPE: DNA
<213> ORGANISM: Artificial
<220> FEATURE:
<223> OTHER INFORMATION: reverse primer

<400> SEQUENCE: 2
gatatatgaa ttcttagttg tttagaaaat tctcgaggc                              39

<210> SEQ ID NO 3
<211> LENGTH: 33
<212> TYPE: DNA
<213> ORGANISM: Artificial
<220> FEATURE:
<223> OTHER INFORMATION: RNAiDMR6F

<400> SEQUENCE: 3
aaaaagcagg ctgaccgtcc acgtctctct gaa                                    33

<210> SEQ ID NO 4
<211> LENGTH: 33
<212> TYPE: DNA
<213> ORGANISM: Artificial
<220> FEATURE:
<223> OTHER INFORMATION: RANiDMR6R

<400> SEQUENCE: 4
agaaagctgg gtgaaacgat gcgaccgata gtc                                    33

<210> SEQ ID NO 5
<211> LENGTH: 29
<212> TYPE: DNA
<213> ORGANISM: Artificial
<220> FEATURE:
<223> OTHER INFORMATION: attB1

<400> SEQUENCE: 5
ggggacaagt ttgtacaaaa aagcaggct                                         29

<210> SEQ ID NO 6
<211> LENGTH: 29
<212> TYPE: DNA
<213> ORGANISM: Artificial
<220> FEATURE:
<223> OTHER INFORMATION: attB2

<400> SEQUENCE: 6
ggggaccact ttgtacaaga aagctgggt                                         29

<210> SEQ ID NO 7
<211> LENGTH: 26
<212> TYPE: DNA
<213> ORGANISM: Artificial
<220> FEATURE:
<223> OTHER INFORMATION: internal primer for At5G24530

<400> SEQUENCE: 7
gagaagtggg atttaaaata gaggaa                                            26

<210> SEQ ID NO 8
<211> LENGTH: 22
<212> TYPE: DNA
<213> ORGANISM: Artificial
<220> FEATURE:
<223> OTHER INFORMATION: QDMR6F

<400> SEQUENCE: 8
```

```
tgtcatcaac ataggtgacc ag                                              22

<210> SEQ ID NO 9
<211> LENGTH: 22
<212> TYPE: DNA
<213> ORGANISM: Artificial
<220> FEATURE:
<223> OTHER INFORMATION: QDMR6R

<400> SEQUENCE: 9
cgatagtcac ggattttctg tg                                              22

<210> SEQ ID NO 10
<211> LENGTH: 20
<212> TYPE: DNA
<213> ORGANISM: Artificial
<220> FEATURE:
<223> OTHER INFORMATION: QAt1g114880F

<400> SEQUENCE: 10
ctcaaggaga atggtccaca                                                 20

<210> SEQ ID NO 11
<211> LENGTH: 20
<212> TYPE: DNA
<213> ORGANISM: Artificial
<220> FEATURE:
<223> OTHER INFORMATION: QAt1g14880R

<400> SEQUENCE: 11
cgacttggcc aaatgtgata                                                 20

<210> SEQ ID NO 12
<211> LENGTH: 21
<212> TYPE: DNA
<213> ORGANISM: Artificial
<220> FEATURE:
<223> OTHER INFORMATION: QAt4g14365F

<400> SEQUENCE: 12
tggttttctg aggcatgtaa a                                               21

<210> SEQ ID NO 13
<211> LENGTH: 20
<212> TYPE: DNA
<213> ORGANISM: Artificial
<220> FEATURE:
<223> OTHER INFORMATION: QAtfg14365R

<400> SEQUENCE: 13
agtgcaggaa cattggttgt                                                 20

<210> SEQ ID NO 14
<211> LENGTH: 20
<212> TYPE: DNA
<213> ORGANISM: Artificial
<220> FEATURE:
<223> OTHER INFORMATION: QACD6F

<400> SEQUENCE: 14
tggacagttc tggagcagat                                                 20

<210> SEQ ID NO 15
<211> LENGTH: 18
<212> TYPE: DNA
<213> ORGANISM: Artificial
```

```
<220> FEATURE:
<223> OTHER INFORMATION: QACD6R

<400> SEQUENCE: 15
caactcctcc gctgtgag                                                     18

<210> SEQ ID NO 16
<211> LENGTH: 23
<212> TYPE: DNA
<213> ORGANISM: Artificial
<220> FEATURE:
<223> OTHER INFORMATION: QPR-5F

<400> SEQUENCE: 16
ggcaaatatc tccagtattc aca                                               23

<210> SEQ ID NO 17
<211> LENGTH: 22
<212> TYPE: DNA
<213> ORGANISM: Artificial
<220> FEATURE:
<223> OTHER INFORMATION: QPR-5R

<400> SEQUENCE: 17
ggtagggcaa ttgttcctta ga                                                22

<210> SEQ ID NO 18
<211> LENGTH: 20
<212> TYPE: DNA
<213> ORGANISM: Artificial
<220> FEATURE:
<223> OTHER INFORMATION: QPR-2F

<400> SEQUENCE: 18
aaggagctta gcctcaccac                                                   20

<210> SEQ ID NO 19
<211> LENGTH: 20
<212> TYPE: DNA
<213> ORGANISM: Artificial
<220> FEATURE:
<223> OTHER INFORMATION: QPR-2R

<400> SEQUENCE: 19
gagggaagca agaatggaac                                                   20

<210> SEQ ID NO 20
<211> LENGTH: 20
<212> TYPE: DNA
<213> ORGANISM: Artificial
<220> FEATURE:
<223> OTHER INFORMATION: QPR-1F

<400> SEQUENCE: 20
gaacacgtgc aatggagttt                                                   20

<210> SEQ ID NO 21
<211> LENGTH: 21
<212> TYPE: DNA
<213> ORGANISM: Artificial
<220> FEATURE:
<223> OTHER INFORMATION: QPR-1R

<400> SEQUENCE: 21
ggttccacca ttgttacacc t                                                 21
```

<210> SEQ ID NO 22
<211> LENGTH: 19
<212> TYPE: DNA
<213> ORGANISM: Artificial
<220> FEATURE:
<223> OTHER INFORMATION: QACT2F

<400> SEQUENCE: 22
aatcacagca cttgcacca                                                    19

<210> SEQ ID NO 23
<211> LENGTH: 20
<212> TYPE: DNA
<213> ORGANISM: Artificial
<220> FEATURE:
<223> OTHER INFORMATION: QACT2R

<400> SEQUENCE: 23
gagggaagca agaatggaac                                                   20

<210> SEQ ID NO 24
<211> LENGTH: 20
<212> TYPE: DNA
<213> ORGANISM: Artificial
<220> FEATURE:
<223> OTHER INFORMATION: Lsat_dmr6_fw1

<400> SEQUENCE: 24
cgatcaaggt caacacatgg                                                   20

<210> SEQ ID NO 25
<211> LENGTH: 20
<212> TYPE: DNA
<213> ORGANISM: Artificial
<220> FEATURE:
<223> OTHER INFORMATION: Lsat_dmr6_fw2

<400> SEQUENCE: 25
tcaaccatta cccagtgtgc                                                   20

<210> SEQ ID NO 26
<211> LENGTH: 20
<212> TYPE: DNA
<213> ORGANISM: Artificial
<220> FEATURE:
<223> OTHER INFORMATION: dmr6_deg_fw1B

<400> SEQUENCE: 26
ttccaggtda ttaaycaygg                                                   20

<210> SEQ ID NO 27
<211> LENGTH: 20
<212> TYPE: DNA
<213> ORGANISM: Artificial
<220> FEATURE:
<223> OTHER INFORMATION: dmr6_deg_fw2B

<400> SEQUENCE: 27
cataaytgga grgaytayct                                                   20

<210> SEQ ID NO 28
<211> LENGTH: 20
<212> TYPE: DNA
<213> ORGANISM: Artificial
<220> FEATURE:
<223> OTHER INFORMATION: dmr6_deg_fw3b

```
<400> SEQUENCE: 28
garcaaggrc arcayatggc                                              20

<210> SEQ ID NO 29
<211> LENGTH: 20
<212> TYPE: DNA
<213> ORGANISM: Artificial
<220> FEATURE:
<223> OTHER INFORMATION: dmr6_deg_fw4

<400> SEQUENCE: 29
aatcctcctt chttcaagga                                              20

<210> SEQ ID NO 30
<211> LENGTH: 20
<212> TYPE: DNA
<213> ORGANISM: Artificial
<220> FEATURE:
<223> OTHER INFORMATION: dmr6_deg_rv3B

<400> SEQUENCE: 30
agtgcattkg ggtchgtrtg                                              20

<210> SEQ ID NO 31
<211> LENGTH: 20
<212> TYPE: DNA
<213> ORGANISM: Artificial
<220> FEATURE:
<223> OTHER INFORMATION: dmr6_deg_rv4

<400> SEQUENCE: 31
aatgttratg acaaargcat                                              20

<210> SEQ ID NO 32
<211> LENGTH: 20
<212> TYPE: DNA
<213> ORGANISM: Artificial
<220> FEATURE:
<223> OTHER INFORMATION: dmr6_deg_rv5

<400> SEQUENCE: 32
gccatrtgyt gyccttgytc                                              20

<210> SEQ ID NO 33
<211> LENGTH: 20
<212> TYPE: DNA
<213> ORGANISM: Artificial
<220> FEATURE:
<223> OTHER INFORMATION: Cuc_dmr6_rv1

<400> SEQUENCE: 33
tccggacatt gaaacttgtg                                              20

<210> SEQ ID NO 34
<211> LENGTH: 20
<212> TYPE: DNA
<213> ORGANISM: Artificial
<220> FEATURE:
<223> OTHER INFORMATION: Cuc_dmr6_rv2

<400> SEQUENCE: 34
tcaaagaact gcttgccaac                                              20

<210> SEQ ID NO 35
```

-continued

```
<211> LENGTH: 20
<212> TYPE: DNA
<213> ORGANISM: Artificial
<220> FEATURE:
<223> OTHER INFORMATION: Cuc_dmr6_fw1

<400> SEQUENCE: 35
cgcactcacc attctccttc                                                      20

<210> SEQ ID NO 36
<211> LENGTH: 19
<212> TYPE: DNA
<213> ORGANISM: Artificial
<220> FEATURE:
<223> OTHER INFORMATION: Cuc_dmr6_fw2

<400> SEQUENCE: 36
ggcctccaag tcctcaaag                                                       19

<210> SEQ ID NO 37
<211> LENGTH: 25
<212> TYPE: DNA
<213> ORGANISM: Artificial
<220> FEATURE:
<223> OTHER INFORMATION: IND_MOP9 Fw

<400> SEQUENCE: 37
tttgggaaca gaaaaagttg gaggt                                                25

<210> SEQ ID NO 38
<211> LENGTH: 25
<212> TYPE: DNA
<213> ORGANISM: Artificial
<220> FEATURE:
<223> OTHER INFORMATION: IND_MOP9 Rv

<400> SEQUENCE: 38
catattcaaa agggaaaatc ccaga                                                25

<210> SEQ ID NO 39
<211> LENGTH: 25
<212> TYPE: DNA
<213> ORGANISM: Artificial
<220> FEATURE:
<223> OTHER INFORMATION: IND_K16H17 Fw

<400> SEQUENCE: 39
tggggttgtg gtttattctg ttgac                                                25

<210> SEQ ID NO 40
<211> LENGTH: 26
<212> TYPE: DNA
<213> ORGANISM: Artificial
<220> FEATURE:
<223> OTHER INFORMATION: IND_K16H17 Rv

<400> SEQUENCE: 40
tggccaatag tagttgatac gcaaga                                               26

<210> SEQ ID NO 41
<211> LENGTH: 25
<212> TYPE: DNA
<213> ORGANISM: Artificial
<220> FEATURE:
<223> OTHER INFORMATION: IND_T4C12 Fw

<400> SEQUENCE: 41
```

-continued tctcgggtaa gacacaagtc gagat                                    25

<210> SEQ ID NO 42
<211> LENGTH: 25
<212> TYPE: DNA
<213> ORGANISM: Artificial
<220> FEATURE:
<223> OTHER INFORMATION: IND_T4C12 Rv

<400> SEQUENCE: 42
tattccaact tgcgacgtag agcat                                    25

<210> SEQ ID NO 43
<211> LENGTH: 24
<212> TYPE: DNA
<213> ORGANISM: Artificial
<220> FEATURE:
<223> OTHER INFORMATION: IND_T11H3 Fw

<400> SEQUENCE: 43
ccaattgggt tatttacttc gatt                                     24

<210> SEQ ID NO 44
<211> LENGTH: 24
<212> TYPE: DNA
<213> ORGANISM: Artificial
<220> FEATURE:
<223> OTHER INFORMATION: IND_T11H3 Rv

<400> SEQUENCE: 44
cggcttttaa caacatattt tcca                                     24

<210> SEQ ID NO 45
<211> LENGTH: 25
<212> TYPE: DNA
<213> ORGANISM: Artificial
<220> FEATURE:
<223> OTHER INFORMATION: IND_F21J6 fw primer

<400> SEQUENCE: 45
aacacatcac caagatgaat ccaga                                    25

<210> SEQ ID NO 46
<211> LENGTH: 25
<212> TYPE: DNA
<213> ORGANISM: Artificial
<220> FEATURE:
<223> OTHER INFORMATION: IND_F21J6 rv primer

<400> SEQUENCE: 46
cctctgcccc aagaaatatt gagat                                    25

<210> SEQ ID NO 47
<211> LENGTH: 24
<212> TYPE: DNA
<213> ORGANISM: Artificial
<220> FEATURE:
<223> OTHER INFORMATION: M450 fw

<400> SEQUENCE: 47
agctttgtat ggtagtgcca atga                                     24

<210> SEQ ID NO 48
<211> LENGTH: 24
<212> TYPE: DNA

```
<213> ORGANISM: Artificial
<220> FEATURE:
<223> OTHER INFORMATION: M450 Rv

<400> SEQUENCE: 48
gcggtatacg ggggttaaaa tcta                                         24

<210> SEQ ID NO 49
<211> LENGTH: 22
<212> TYPE: DNA
<213> ORGANISM: Artificial
<220> FEATURE:
<223> OTHER INFORMATION: M490 Fw

<400> SEQUENCE: 49
atggccaacc actctttgtt ac                                           22

<210> SEQ ID NO 50
<211> LENGTH: 22
<212> TYPE: DNA
<213> ORGANISM: Artificial
<220> FEATURE:
<223> OTHER INFORMATION: M490 Rv

<400> SEQUENCE: 50
acaagcaaga agaacagcga ag                                           22

<210> SEQ ID NO 51
<211> LENGTH: 24
<212> TYPE: DNA
<213> ORGANISM: Artificial
<220> FEATURE:
<223> OTHER INFORMATION: M525 Fw

<400> SEQUENCE: 51
gaaatttggt tgttggcatt tatc                                         24

<210> SEQ ID NO 52
<211> LENGTH: 25
<212> TYPE: DNA
<213> ORGANISM: Artificial
<220> FEATURE:
<223> OTHER INFORMATION: M525 Rv

<400> SEQUENCE: 52
tcaagatctt catattctca ttcca                                        25

<210> SEQ ID NO 53
<211> LENGTH: 25
<212> TYPE: DNA
<213> ORGANISM: Artificial
<220> FEATURE:
<223> OTHER INFORMATION: M545 Fw

<400> SEQUENCE: 53
cagctgaagt atgtttcatc cctttt                                       25

<210> SEQ ID NO 54
<211> LENGTH: 24
<212> TYPE: DNA
<213> ORGANISM: Artificial
<220> FEATURE:
<223> OTHER INFORMATION: M545 Rv

<400> SEQUENCE: 54
cttgcaattg ttgggactag gtaa                                         24
```

<210> SEQ ID NO 55
<211> LENGTH: 24
<212> TYPE: DNA
<213> ORGANISM: Artificial
<220> FEATURE:
<223> OTHER INFORMATION: M555 Fw

<400> SEQUENCE: 55
tcactaacca gtgaaaaagg ttgc                                              24

<210> SEQ ID NO 56
<211> LENGTH: 24
<212> TYPE: DNA
<213> ORGANISM: Artificial
<220> FEATURE:
<223> OTHER INFORMATION: M555 Rv

<400> SEQUENCE: 56
tatacagcga atagcaaagc caag                                              24

<210> SEQ ID NO 57
<211> LENGTH: 24
<212> TYPE: DNA
<213> ORGANISM: Artificial
<220> FEATURE:
<223> OTHER INFORMATION: M470 Fw

<400> SEQUENCE: 57
ccgcgagtgt aatatatctc tcct                                              24

<210> SEQ ID NO 58
<211> LENGTH: 24
<212> TYPE: DNA
<213> ORGANISM: Artificial
<220> FEATURE:
<223> OTHER INFORMATION: M470 Rv

<400> SEQUENCE: 58
cagtttaacg catgaagtgc tagt                                              24

<210> SEQ ID NO 59
<211> LENGTH: 24
<212> TYPE: DNA
<213> ORGANISM: Artificial
<220> FEATURE:
<223> OTHER INFORMATION: M590 Fw

<400> SEQUENCE: 59
gcatcatttg taccgtactg agtc                                              24

<210> SEQ ID NO 60
<211> LENGTH: 24
<212> TYPE: DNA
<213> ORGANISM: Artificial
<220> FEATURE:
<223> OTHER INFORMATION: M590 Rv

<400> SEQUENCE: 60
tagtggatac tctgtccctg aggt                                              24

<210> SEQ ID NO 61
<211> LENGTH: 1026
<212> TYPE: DNA
<213> ORGANISM: Arabidopsis thaliana

<400> SEQUENCE: 61

```
atggcggcaa agctgatatc caccggtttc cgtcatacta ctttgccgga aaactatgtc      60
cggccaatct ccgaccgtcc acgtctctct gaagtctctc aactcgaaga tttccctctc     120
atcgatctct cttccactga tcgatctttt ctcatccaac aaatccacca agcttgtgcc     180
cgattcggat tttttcaggt cataaatcac ggagttaaca aacaaataat agatgagatg     240
gtgagtgttg cgcgtgagtt ctttagcatg tctatggaag aaaaaatgaa gctatattca     300
gacgatccaa cgaagacaac aagattatcg acgagcttca atgtgaagaa agaagaagtc     360
aacaattgga gagactatct aagactccat tgttatccta tccacaagta tgtcaatgag     420
tggccgtcaa accctccttc tttcaaggaa atagtaagta aatacagtag agaagtaaga     480
gaagtgggat ttaaaataga ggaattaata tcagagagct taggtttaga aaaagattac     540
atgaagaaag tgcttggtga acaaggtcaa cacatggcag tcaactatta tcctccatgt     600
cctgaacctg agctcactta cggtttacct gctcataccg acccaaacgc cctaaccatt     660
cttcttcaag acactactgt ttgcggtctc cagatcttga tcgacggtca gtggttcgcc     720
gttaatccac atcctgatgc ttttgtcatc aacataggtg accagttaca ggcattaagt     780
aatggagtat acaaaagtgt tggcatcgc gctgtaacaa acacagaaaa tccgagacta     840
tcggtcgcat cgtttctgtg cccagctgac tgtgctgtca tgagcccggc aagcccttg      900
tgggaagctg aggacgatga aacgaaacca gtctacaaag atttcactta tgcagagtat     960
tacaagaagt tttggagtag gaatctggac caagaacatt gcctcgagaa ttttctaaac    1020
aactaa                                                                1026
```

<210> SEQ ID NO 62
<211> LENGTH: 341
<212> TYPE: PRT
<213> ORGANISM: Arabidopsis thaliana

<400> SEQUENCE: 62

```
Met Ala Ala Lys Leu Ile Ser Thr Gly Phe Arg His Thr Thr Leu Pro
1               5                   10                  15

Glu Asn Tyr Val Arg Pro Ile Ser Asp Arg Pro Arg Leu Ser Glu Val
            20                  25                  30

Ser Gln Leu Glu Asp Phe Pro Leu Ile Asp Leu Ser Ser Thr Asp Arg
        35                  40                  45

Ser Phe Leu Ile Gln Gln Ile His Gln Ala Cys Ala Arg Phe Gly Phe
    50                  55                  60

Phe Gln Val Ile Asn His Gly Val Asn Lys Gln Ile Ile Asp Glu Met
65                  70                  75                  80

Val Ser Val Ala Arg Glu Phe Phe Ser Met Ser Met Glu Glu Lys Met
                85                  90                  95

Lys Leu Tyr Ser Asp Asp Pro Thr Lys Thr Thr Arg Leu Ser Thr Ser
            100                 105                 110

Phe Asn Val Lys Lys Glu Glu Val Asn Asn Trp Arg Asp Tyr Leu Arg
        115                 120                 125

Leu His Cys Tyr Pro Ile His Lys Tyr Val Asn Glu Trp Pro Ser Asn
    130                 135                 140

Pro Pro Ser Phe Lys Glu Ile Val Ser Lys Tyr Ser Arg Glu Val Arg
145                 150                 155                 160

Glu Val Gly Phe Lys Ile Glu Glu Leu Ile Ser Glu Ser Leu Gly Leu
                165                 170                 175
```

```
Glu Lys Asp Tyr Met Lys Val Leu Gly Glu Gln Gly Gln His Met
            180                 185                 190

Ala Val Asn Tyr Tyr Pro Pro Cys Pro Glu Pro Glu Leu Thr Tyr Gly
        195                 200                 205

Leu Pro Ala His Thr Asp Pro Asn Ala Leu Thr Ile Leu Leu Gln Asp
210                 215                 220

Thr Thr Val Cys Gly Leu Gln Ile Leu Ile Asp Gly Gln Trp Phe Ala
225                 230                 235                 240

Val Asn Pro His Pro Asp Ala Phe Val Ile Asn Ile Gly Asp Gln Leu
                245                 250                 255

Gln Ala Leu Ser Asn Gly Val Tyr Lys Ser Val Trp His Arg Ala Val
        260                 265                 270

Thr Asn Thr Glu Asn Pro Arg Leu Ser Val Ala Ser Phe Leu Cys Pro
        275                 280                 285

Ala Asp Cys Ala Val Met Ser Pro Ala Lys Pro Leu Trp Glu Ala Glu
        290                 295                 300

Asp Asp Glu Thr Lys Pro Val Tyr Lys Asp Phe Thr Tyr Ala Glu Tyr
305                 310                 315                 320

Tyr Lys Lys Phe Trp Ser Arg Asn Leu Asp Gln Glu His Cys Leu Glu
                325                 330                 335

Asn Phe Leu Asn Asn
            340

<210> SEQ ID NO 63
<211> LENGTH: 335
<212> TYPE: PRT
<213> ORGANISM: Aquilegia sp.

<400> SEQUENCE: 63

Met Glu Ser Ser Asn Val Leu Leu Thr Gly Thr Arg His Ser Asn Leu
1               5                   10                  15

Pro Glu Asn Tyr Val Arg Ser Val Ser Asp Arg Pro Arg Leu Ser Glu
            20                  25                  30

Val Lys Asp Cys Glu Asn Val Pro Val Ile Asp Leu Ser Val Ala Asp
        35                  40                  45

Glu Ser Leu Leu Ala Gln Gln Ile Gly Asn Ala Cys Lys Ser His Gly
    50                  55                  60

Phe Phe Gln Val Ile Asn His Gly Val Asn Ser Glu Leu Val Glu Lys
65                  70                  75                  80

Met Met Glu Ile Ser His Glu Phe Phe His Leu Pro Leu Asp Val Lys
                85                  90                  95

Met Gln Phe Tyr Ser Asp Asp Pro Thr Lys Thr Met Arg Leu Ser Thr
            100                 105                 110

Ser Phe Asn Leu Lys Lys Glu Ser Val His Asn Trp Arg Asp Tyr Leu
        115                 120                 125

Arg Leu His Cys His Pro Ile Glu Lys Tyr Val Gln Glu Trp Pro Ser
    130                 135                 140

Val Pro Ser Thr Phe Lys Asp Val Val Ala Thr Tyr Cys Lys Glu Val
145                 150                 155                 160

Arg Lys Leu Gly Leu Arg Leu Leu Gly Ser Ile Ser Leu Ser Leu Gly
                165                 170                 175

Leu Glu Glu Asp Tyr Ile Glu Lys Val Leu Gly Asp Gln Gly Gln His
            180                 185                 190

Met Ala Val Asn Tyr Tyr Pro Pro Cys Pro Glu Pro Glu Leu Thr Tyr
        195                 200                 205
```

```
Gly Leu Pro Arg His Thr Asp Pro Asn Thr Ile Thr Ile Leu Leu Gln
            210                 215                 220

Gly Gln Glu Val Ala Gly Leu Gln Val Leu His Asn Gly Lys Trp Val
225                 230                 235                 240

Ala Val Asn Pro Tyr Pro Asn Ala Phe Val Val Asn Ile Gly Asp Gln
                245                 250                 255

Ile Gln Ala Leu Ser Asn Gly Asn Tyr Ala Ser Val Trp His Arg Ala
            260                 265                 270

Thr Val Asn Thr Asp Arg Glu Arg Ile Ser Val Ala Ser Phe Leu Cys
        275                 280                 285

Pro Ala Asn Asp Ala Ile Ile Cys Pro Ala Val Lys Asp Gly Ser Pro
290                 295                 300

Ser Met Tyr Lys Lys Phe Thr Tyr Asp Glu Tyr Tyr Lys Lys Phe Trp
305                 310                 315                 320

Ser Gly Asn Leu Asp Gln Gln His Cys Leu Glu Leu Phe Lys Glu
            325                 330                 335

<210> SEQ ID NO 64
<211> LENGTH: 337
<212> TYPE: PRT
<213> ORGANISM: Citrus sinensis

<400> SEQUENCE: 64

Met Asp Thr Lys Val Leu Ser Ser Gly Ile Arg Tyr Thr Asn Leu Pro
1               5                   10                  15

Glu Gly Tyr Val Arg Pro Glu Ser Glu Arg Pro Asn Leu Ser Glu Val
            20                  25                  30

Ser Glu Cys Lys Asn Val Pro Val Ile Asp Leu Ala Cys Asp Asp Arg
        35                  40                  45

Ser Leu Ile Val Gln Gln Val Ala Asp Ala Cys Lys Asn Tyr Gly Phe
    50                  55                  60

Phe Gln Ala Ile Asn His Glu Val Pro Leu Glu Thr Val Glu Arg Val
65                  70                  75                  80

Leu Glu Val Ala Lys Glu Phe Phe Asn Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Asn Lys Glu Lys Val His Asn Trp Arg Asp Tyr Leu Arg
        115                 120                 125

Leu His Cys Tyr Pro Leu Asp Lys Tyr Val Pro Glu Trp Pro Ser Asn
    130                 135                 140

Pro Ser Thr Phe Lys Glu Phe Val Ser Thr Tyr Cys Ser Glu Val Arg
145                 150                 155                 160

Gly Leu Gly Tyr Arg Val Leu Glu Leu Ile Ser Glu Ser Leu Gly Leu
                165                 170                 175

Glu Lys Asp Tyr Ile Lys Lys Val Leu Gly Glu Gln Gly Gln His Met
            180                 185                 190

Ala Val Asn Phe Tyr Pro Pro Cys Pro Glu Pro Glu Leu Thr Tyr Gly
        195                 200                 205

Leu Pro Gly His Thr Asp Pro Asn Ala Leu Thr Ile Leu Leu Gln Asp
    210                 215                 220

Leu Glu Val Ala Gly Leu Gln Val Leu Lys Asp Asp Lys Trp Val Ala
225                 230                 235                 240

Val Asn Pro Leu Pro Asn Ala Phe Val Ile Asn Ile Gly Asp Gln Leu
```

```
                    245                 250                 255
Gln Ala Leu Ser Asn Gly Arg Tyr Lys Ser Val Trp His Arg Ala Ile
                260                 265                 270

Val Asn Ala Glu Lys Ala Arg Met Ser Val Ala Ser Phe Leu Cys Pro
            275                 280                 285

Asn Asn Asp Ala Met Ile Ser Pro Pro Lys Ala Leu Thr Glu Asp Gly
        290                 295                 300

Ser Gly Ala Val Tyr Arg Asp Phe Thr Tyr Ala Glu Tyr Tyr Ser Lys
305                 310                 315                 320

Phe Trp Ser Arg Asn Leu Asp Gln Glu His Cys Leu Glu Leu Phe Lys
                325                 330                 335

Asn

<210> SEQ ID NO 65
<211> LENGTH: 337
<212> TYPE: PRT
<213> ORGANISM: Coffea canephora

<400> SEQUENCE: 65

Met Glu Thr Lys Val Ile Ser Ser Gly Ile Lys Tyr Thr Ser Leu Pro
1               5                   10                  15

Glu Ser Tyr Val Arg Pro Glu Ser Glu Arg Pro Arg Leu Ser Glu Val
            20                  25                  30

Ser Asp Cys Gln Asn Val Pro Val Asp Leu Gly Phe Gly Asp Arg
        35                  40                  45

Asn Leu Met Val Arg Gln Ile Gly Asp Ala Cys Arg Asp Tyr Gly Phe
    50                  55                  60

Phe Gln Val Ile Asn His Gly Val Ser Lys Asp Ala Val Asp Lys Met
65                  70                  75                  80

Leu Glu Thr Ala Thr Glu Phe Phe Ser Leu Pro Val Glu Glu Lys Leu
                85                  90                  95

Lys Leu Tyr Ser Asp Asp Pro Ser Lys Thr Thr Arg Leu Ser Thr Ser
            100                 105                 110

Phe Asn Val Lys Lys Glu Thr Val His Asn Trp Arg Asp Tyr Leu Arg
        115                 120                 125

Leu His Cys Tyr Pro Leu Glu Lys Tyr Val Pro Glu Trp Pro Ser Asn
    130                 135                 140

Pro Pro Ser Phe Lys Glu Met Val Ser Asn Tyr Cys Val Gln Ile Arg
145                 150                 155                 160

Glu Leu Gly Leu Arg Leu Glu Glu Ala Ile Ala Glu Ser Leu Gly Leu
                165                 170                 175

Asp Lys Glu Cys Ile Lys Lys Val Leu Gly Asp Gln Gly Gln His Met
            180                 185                 190

Ala Val Asn Tyr Tyr Pro Pro Cys Pro Gln Pro Asp Leu Thr Tyr Gly
        195                 200                 205

Leu Pro Gly His Thr Asp Pro Asn Ala Leu Thr Ile Leu Leu Gln Asp
    210                 215                 220

Leu Asn Val Ala Gly Leu Gln Val Leu Arg Asp Gly Arg Trp Leu Ala
225                 230                 235                 240

Val Lys Pro His Pro Asp Ala Phe Val Val Asn Ile Gly Asp Gln Leu
                245                 250                 255

Gln Ala Leu Ser Asn Gly Ile Tyr Lys Ser Val Trp His Arg Ala Val
            260                 265                 270

Val Asn Ala Asp Gln Pro Arg Leu Ser Val Ala Ser Phe Leu Cys Pro
```

```
            275                 280                 285
Cys Asp His Ala Val Ile Ser Ala Pro Lys Pro Leu Thr Ala Asp Gly
    290                 295                 300

Ser Pro Val Val Tyr Arg Asp Phe Thr Tyr Ala Gln Tyr Tyr Lys Lys
305                 310                 315                 320

Phe Trp Ser Arg Asn Leu Asp Gln Glu His Cys Leu Glu Leu Phe Lys
                325                 330                 335

Asn

<210> SEQ ID NO 66
<211> LENGTH: 1029
<212> TYPE: DNA
<213> ORGANISM: Cucumis sativus

<400> SEQUENCE: 66
atgagcagtg tgatggagat ccaactttg tgttcagggg acgtcacga gaagttgcca      60 gagaagtatg aacggcctga atcggatagg ccgcggctgt cggaggtgtg ttgttgggac    120
aaggttccaa taatcgactt gggatgcgag gagagagaga tgattgtgaa gcaagtggag    180
gaggcctgca agtcttacgg cttttttccag gttataaatc atggtgtgag gaaggaattg    240
gtggagaaag tgatagaagt tggcaagcag ttctttgagc tgccgatgga ggagaagttg    300 aaatttatt cagacgaccc ttccaagacc gtcagactct ccacaagttt caatgtccgg    360
aaagagcaat ttcgcaactg gagggattat ctcagactcc attgctatcc tctctccaac    420
tacacccccc attggccctc taacccacca tccttcaggg aaatagtgag tagttattgc    480
aatgaagtac gaaaagttgg gtacagaata gaggagctaa tatcggagag cttgggctg     540 gagaaggaat acataaggaa gaagttgggt gaacaaggtc agcacatggc tataaattat    600
tatccgccat gtccccaacc agaactcacc tacgggctcc ctggccatac ggatcccaac    660
gcactcacca ttctccttca ggatctccat gtcgccggcc tccaagtcct caaagatgga    720
aagtggctag cggtcaaccc ccacccccaat gcctttgtaa tcaatatagg cgaccaattg    780
caggcattga gcaatggggt gtacaagagc gtttggcacc gagcggtggt caatgttgat    840
aagcccaggc tgtcggtcgc ttcttttctc tgcccttgtg atgacgccct cattactcct    900
gcaccgctcc tctcccagcc ttcccccatt tacagacctt tcacctacgc ccagtactac    960 aatactttt ggagcagaaa cttggatcaa caacattgct ggaactatt taaaaccac    1020 cctccttaa                                                          1029

<210> SEQ ID NO 67
<211> LENGTH: 342
<212> TYPE: PRT
<213> ORGANISM: Cucumis sativus

<400> SEQUENCE: 67

Met Ser Ser Val Met Glu Ile Gln Leu Leu Cys Ser Gly Gly Arg His
1               5                   10                  15

Glu Lys Leu Pro Glu Lys Tyr Glu Arg Pro Glu Ser Asp Arg Pro Arg
            20                  25                  30

Leu Ser Glu Val Cys Cys Trp Asp Lys Val Pro Ile Ile Asp Leu Gly
        35                  40                  45

Cys Glu Glu Arg Glu Met Ile Val Lys Gln Val Glu Glu Ala Cys Lys
    50                  55                  60

Ser Tyr Gly Phe Phe Gln Val Ile Asn His Gly Val Arg Lys Glu Leu
65                  70                  75                  80
```

Val Glu Lys Val Ile Glu Val Gly Lys Gln Phe Phe Glu Leu Pro Met
                85                  90                  95

Glu Glu Lys Leu Lys Phe Tyr Ser Asp Asp Pro Ser Lys Thr Val Arg
            100                 105                 110

Leu Ser Thr Ser Phe Asn Val Arg Lys Glu Gln Phe Arg Asn Trp Arg
            115                 120                 125

Asp Tyr Leu Arg Leu His Cys Tyr Pro Leu Ser Asn Tyr Thr Pro His
    130                 135                 140

Trp Pro Ser Asn Pro Pro Ser Phe Arg Glu Ile Val Ser Ser Tyr Cys
145                 150                 155                 160

Asn Glu Val Arg Lys Val Gly Tyr Arg Ile Glu Glu Leu Ile Ser Glu
                165                 170                 175

Ser Leu Gly Leu Glu Lys Glu Tyr Ile Arg Lys Lys Leu Gly Glu Gln
            180                 185                 190

Gly Gln His Met Ala Ile Asn Tyr Tyr Pro Pro Cys Pro Gln Pro Glu
        195                 200                 205

Leu Thr Tyr Gly Leu Pro Gly His Thr Asp Pro Asn Ala Leu Thr Ile
    210                 215                 220

Leu Leu Gln Asp Leu His Val Ala Gly Leu Gln Val Leu Lys Asp Gly
225                 230                 235                 240

Lys Trp Leu Ala Val Asn Pro His Pro Asn Ala Phe Val Ile Asn Ile
                245                 250                 255

Gly Asp Gln Leu Gln Ala Leu Ser Asn Gly Val Tyr Lys Ser Val Trp
            260                 265                 270

His Arg Ala Val Asn Val Asp Lys Pro Arg Leu Ser Val Ala Ser
        275                 280                 285

Phe Leu Cys Pro Cys Asp Asp Ala Leu Ile Thr Pro Ala Pro Leu Leu
    290                 295                 300

Ser Gln Pro Ser Pro Ile Tyr Arg Pro Phe Thr Tyr Ala Gln Tyr Tyr
305                 310                 315                 320

Asn Thr Phe Trp Ser Arg Asn Leu Asp Gln Gln His Cys Leu Glu Leu
                325                 330                 335

Phe Lys Asn His Pro Pro
            340

<210> SEQ ID NO 68
<211> LENGTH: 337
<212> TYPE: PRT
<213> ORGANISM: Gossypium hirsutum

<400> SEQUENCE: 68

Met Asp Thr Lys Val Leu Ser Ser Gly Ile His Tyr Ser Ser Leu Pro
1               5                   10                  15

Glu Ser Tyr Val Arg Pro Glu Ser Glu Arg Pro Arg Leu Ser Glu Val
            20                  25                  30

Ser Gln Cys Asp Asn Val Pro Val Ile Asp Leu Gly Cys Glu Asp Arg
        35                  40                  45

Ser His Ile Val Gln Gln Ile Ala Leu Ala Cys Ile Asn Tyr Gly Phe
    50                  55                  60

Phe Gln Val Ile Asn His Gly Val Ser Lys Glu Ala Val Glu Arg Met
65                  70                  75                  80

Leu Gln Val Ala His Asp Phe Phe Gly Leu Pro Val Glu Glu Lys Met
                85                  90                  95

Lys Leu Tyr Ser Asp Asp Pro Ser Lys Thr Met Arg Leu Ser Thr Ser

```
                100                 105                 110
Phe Asn Val Lys Lys Glu Lys Val His Asn Trp Arg Asp Tyr Leu Arg
            115                 120                 125

Leu His Cys Tyr Pro Leu His Lys Tyr Val Pro Glu Trp Pro Ser Asn
        130                 135                 140

Pro Pro Ser Phe Lys Gln Ile Val Ser Asp Tyr Cys Val Gln Val Arg
145                 150                 155                 160

Glu Leu Gly Tyr Arg Leu Gln Glu Leu Ile Ser Glu Ser Leu Gly Leu
                165                 170                 175

Glu Lys Asp Tyr Ile Lys Lys Val Leu Gly Glu Gln Gly Gln His Met
            180                 185                 190

Ala Val Asn Tyr Tyr Pro Pro Cys Pro Glu Pro Glu Leu Thr Tyr Gly
        195                 200                 205

Leu Pro Gly His Thr Asp Pro Asn Ala Leu Thr Ile Leu Leu Gln Asp
    210                 215                 220

Leu Gln Val Ala Gly Leu Gln Val Leu Lys Asp Gly Lys Trp Leu Ala
225                 230                 235                 240

Val Asn Pro Gln Thr Asn Ala Phe Val Ile Asn Ile Gly Asp Gln Leu
                245                 250                 255

Gln Ala Leu Ser Asn Gly Thr Tyr Lys Ser Val Trp His Arg Ala Ile
            260                 265                 270

Val Asn Thr Asp Lys Pro Arg Met Ser Val Ala Ser Phe Leu Cys Pro
        275                 280                 285

Tyr Asp His Ala Leu Ile Ser Pro Ala Lys Pro Leu Thr Gln His Gly
    290                 295                 300

Cys Gly Ala Val Tyr Arg Asp Phe Thr Tyr Ala Glu Tyr Tyr Ser Lys
305                 310                 315                 320

Phe Trp Gly Arg Asn Leu Asp Gln Glu His Cys Leu Glu Leu Phe Lys
                325                 330                 335

Asn

<210> SEQ ID NO 69
<211> LENGTH: 1014
<212> TYPE: DNA
<213> ORGANISM: Lactuca sativa

<400> SEQUENCE: 69
atggccgcaa aagtcatctc cagtggattc cggtatacta ctctaccgga gagctacgtc      60
cgtccggtta acgacagacc taacctatct caagtttccg attgcaacga cgttcctgtt     120
attgacatcg gttgtggtga tagacaactc ataagccaac aaattggcga tgcttgtaga     180
agatacggtt ttttccaggt gattaatcat ggtgtgcctg atgaaatagt ggagaaaatg     240
caacaagtag gtagggagtt tttcctgttg cctgtggaag agaagatgaa gctttactca     300
gaggatccat cgaagacgat gaggctatcc accagcttta acgtccaaaa agaacaaatt     360
cataactggc gagattatct ccgccttcac tgttatcctc tggatcaata cagtcctgaa     420
tggccttcaa atccttctta tttcaaggaa tatgttggta attattgtac agcagtgcga     480
aatttaggaa tgagaatatt agaatcaata tcagaaagtt tagggttaca aaagaagaa      540 ataaaaacta tattaggcga tcaaggtcaa cacatggcca tcaaccatta cccagtgtgc     600
cctgagcccg agctaaccta cgggctaccc gggcacacag accccaatgc tctcaccatc     660
cttctacagg acacactggt ctctggtctt caggttctca agatggcaa atggttagcc      720 gttaaaccac accctaatgc gtttgtaatt aacattggtg atcagttaga ggcggtgagt     780
```

```
aatggtgaat ataaaagtgt atggcatcga gctgtggtta actcagacaa cccgcgaatg    840
tctatagctt cgttttttgtg tccttgtaat gacaccgtta ttagggctcc taaagaaata    900
ataaaggaag gatcgaaacc tgttttcaaa gaatttactt atgcagaata ctacgcgaag    960
ttttggacaa gaaaccttga tcaagaacat tgcttagaat tcttcaagaa ctag          1014
```

<210> SEQ ID NO 70
<211> LENGTH: 337
<212> TYPE: PRT
<213> ORGANISM: Lactuca sativa

<400> SEQUENCE: 70

```
Met Ala Ala Lys Val Ile Ser Ser Gly Phe Arg Tyr Thr Thr Leu Pro
1               5                   10                  15

Glu Ser Tyr Val Arg Pro Val Asn Asp Arg Pro Asn Leu Ser Gln Val
            20                  25                  30

Ser Asp Cys Asn Asp Val Pro Val Ile Asp Ile Gly Cys Gly Asp Arg
        35                  40                  45

Gln Leu Ile Ser Gln Gln Ile Gly Asp Ala Cys Arg Arg Tyr Gly Phe
    50                  55                  60

Phe Gln Val Ile Asn His Gly Val Pro Asp Glu Ile Val Glu Lys Met
65                  70                  75                  80

Gln Gln Val Gly Arg Glu Phe Phe Leu Leu Pro Val Glu Glu Lys Met
                85                  90                  95

Lys Leu Tyr Ser Glu Asp Pro Ser Lys Thr Met Arg Leu Ser Thr Ser
            100                 105                 110

Phe Asn Val Gln Lys Glu Gln Ile His Asn Trp Arg Asp Tyr Leu Arg
        115                 120                 125

Leu His Cys Tyr Pro Leu Asp Gln Tyr Ser Pro Glu Trp Pro Ser Asn
    130                 135                 140

Pro Ser Tyr Phe Lys Glu Tyr Val Gly Asn Tyr Cys Thr Ala Val Arg
145                 150                 155                 160

Asn Leu Gly Met Arg Ile Leu Glu Ser Ile Ser Glu Ser Leu Gly Leu
                165                 170                 175

Gln Lys Glu Glu Ile Lys Thr Ile Leu Gly Asp Gln Gly Gln His Met
            180                 185                 190

Ala Ile Asn His Tyr Pro Val Cys Pro Glu Pro Glu Leu Thr Tyr Gly
        195                 200                 205

Leu Pro Gly His Thr Asp Pro Asn Ala Leu Thr Ile Leu Leu Gln Asp
    210                 215                 220

Thr Leu Val Ser Gly Leu Gln Val Leu Lys Asp Gly Lys Trp Leu Ala
225                 230                 235                 240

Val Lys Pro His Pro Asn Ala Phe Val Ile Asn Ile Gly Asp Gln Leu
                245                 250                 255

Glu Ala Val Ser Asn Gly Glu Tyr Lys Ser Val Trp His Arg Ala Val
            260                 265                 270

Val Asn Ser Asp Asn Pro Arg Met Ser Ile Ala Ser Phe Leu Cys Pro
        275                 280                 285

Cys Asn Asp Thr Val Ile Arg Ala Pro Lys Glu Ile Ile Lys Glu Gly
    290                 295                 300

Ser Lys Pro Val Phe Lys Glu Phe Thr Tyr Ala Glu Tyr Tyr Ala Lys
305                 310                 315                 320

Phe Trp Thr Arg Asn Leu Asp Gln Glu His Cys Leu Glu Phe Phe Lys
                325                 330                 335
```

Asn

<210> SEQ ID NO 71
<211> LENGTH: 338
<212> TYPE: PRT
<213> ORGANISM: Medicago truncatula

<400> SEQUENCE: 71

```
Met Asp Thr Lys Val Leu Ser Ser Gly Ile His Tyr Ser Lys Leu Pro
1               5                   10                  15

Glu Ser Tyr Ile Arg Pro Glu Ser Asp Arg Pro Cys Leu Ser Gln Val
            20                  25                  30

Ser Glu Phe Glu Asn Val Pro Ile Ile Asp Leu Gly Ser His Asn Arg
        35                  40                  45

Thr Gln Ile Val Gln Gln Ile Gly Glu Ala Cys Ser Ser Tyr Gly Phe
    50                  55                  60

Phe Gln Val Val Asn His Gly Val Pro Leu Glu Glu Leu Lys Lys Thr
65                  70                  75                  80

Ala Glu Val Ala Tyr Asp Phe Phe Lys Leu Pro Val Glu Glu Lys Met
                85                  90                  95

Lys Leu Tyr Ser Asp Asp Pro Thr Lys Thr Met Arg Leu Ser Thr Ser
            100                 105                 110

Phe Asn Val Asn Lys Glu Glu Val His Asn Trp Arg Asp Tyr Leu Arg
        115                 120                 125

Leu His Cys Tyr Pro Leu Asp Asn Tyr Val Pro Glu Trp Pro Ser Asn
    130                 135                 140

Pro Pro Ser Phe Lys Glu Thr Val Ala Asn Tyr Cys Lys Glu Val Arg
145                 150                 155                 160

Glu Leu Gly Leu Arg Ile Glu Glu Tyr Ile Ser Glu Ser Leu Gly Leu
                165                 170                 175

Glu Lys Asp Tyr Leu Arg Asn Ala Leu Gly Glu Gln Gly Gln His Met
            180                 185                 190

Ala Val Asn Tyr Tyr Pro Pro Cys Pro Gln Pro Glu Leu Thr Tyr Gly
        195                 200                 205

Leu Pro Gly His Thr Asp Pro Asn Ala Leu Thr Ile Leu Leu Gln Asp
    210                 215                 220

Leu His Val Ala Gly Leu Gln Val Leu Lys Asp Gly Lys Trp Leu Ala
225                 230                 235                 240

Ile Asn Pro Ile Pro Asp Ala Phe Val Ile Asn Ile Gly Asp Gln Leu
                245                 250                 255

Gln Ala Leu Ser Asn Gly Leu Tyr Lys Ser Val Trp His Arg Ala Ile
            260                 265                 270

Val Asn Ala Glu Lys Pro Arg Leu Ser Val Ala Ser Phe Leu Cys Pro
        275                 280                 285

Asp Asn Glu Ala Leu Ile Cys Pro Ala Lys Pro Leu Thr Glu Asp Gly
    290                 295                 300

Ser Gly Ala Val Tyr Arg Gly Phe Thr Tyr Pro Glu Tyr Tyr Ser Lys
305                 310                 315                 320

Phe Trp Ser Arg Asp Leu Glu Lys Glu His Cys Leu Glu Phe Phe Lys
                325                 330                 335

Asn Asn
```

<210> SEQ ID NO 72
<211> LENGTH: 342

<212> TYPE: PRT
<213> ORGANISM: Oryza sativa

<400> SEQUENCE: 72

```
Met Ala Ala Glu Ala Glu Gln Gln His Gln Leu Leu Ser Thr Ala Val
1               5                   10                  15

His Asp Thr Met Pro Gly Lys Tyr Val Arg Pro Glu Ser Gln Arg Pro
            20                  25                  30

Arg Leu Asp Leu Val Val Ser Asp Ala Arg Ile Pro Val Val Asp Leu
        35                  40                  45

Ala Ser Pro Asp Arg Ala Ala Val Ser Ala Val Gly Asp Ala Cys
    50                  55                  60

Arg Thr His Gly Phe Phe Gln Val Val Asn His Gly Ile Asp Ala Ala
65              70                  75                  80

Leu Ile Ala Ser Val Met Glu Val Gly Arg Glu Phe Phe Arg Leu Pro
                85                  90                  95

Ala Glu Glu Lys Ala Lys Leu Tyr Ser Asp Asp Pro Ala Lys Lys Ile
            100                 105                 110

Arg Leu Ser Thr Ser Phe Asn Val Arg Lys Glu Thr Val His Asn Trp
        115                 120                 125

Arg Asp Tyr Leu Arg Leu His Cys Tyr Pro Leu His Gln Phe Val Pro
    130                 135                 140

Asp Trp Pro Ser Asn Pro Pro Ser Phe Lys Glu Ile Ile Gly Thr Tyr
145                 150                 155                 160

Cys Thr Glu Val Arg Glu Leu Gly Phe Arg Leu Tyr Glu Ala Ile Ser
                165                 170                 175

Glu Ser Leu Gly Leu Glu Gly Gly Tyr Met Arg Glu Thr Leu Gly Glu
            180                 185                 190

Gln Glu Gln His Met Ala Val Asn Tyr Tyr Pro Gln Cys Pro Glu Pro
        195                 200                 205

Glu Leu Thr Tyr Gly Leu Pro Ala His Thr Asp Pro Asn Ala Leu Thr
    210                 215                 220

Ile Leu Leu Met Asp Asp Gln Val Ala Gly Leu Gln Val Leu Asn Asp
225                 230                 235                 240

Gly Lys Trp Ile Ala Val Asn Pro Gln Pro Gly Ala Leu Val Ile Asn
                245                 250                 255

Ile Gly Asp Gln Leu Gln Ala Leu Ser Asn Gly Lys Tyr Arg Ser Val
            260                 265                 270

Trp His Arg Ala Val Val Asn Ser Asp Arg Glu Arg Met Ser Val Ala
        275                 280                 285

Ser Phe Leu Cys Pro Cys Asn Ser Val Glu Leu Gly Pro Ala Lys Lys
    290                 295                 300

Leu Ile Thr Asp Asp Ser Pro Ala Val Tyr Arg Asn Tyr Thr Tyr Asp
305                 310                 315                 320

Glu Tyr Tyr Lys Lys Phe Trp Ser Arg Asn Leu Asp Gln Glu His Cys
                325                 330                 335

Leu Glu Leu Phe Arg Thr
            340
```

<210> SEQ ID NO 73
<211> LENGTH: 342
<212> TYPE: PRT
<213> ORGANISM: Oryza sativa

<400> SEQUENCE: 73

```
Met Ala Asp Gln Leu Ile Ser Thr Ala Asp His Asp Thr Leu Pro Gly
1               5                   10                  15

Asn Tyr Val Arg Pro Glu Ala Gln Arg Pro Arg Leu Ala Asp Val Leu
            20                  25                  30

Ser Asp Ala Ser Ile Pro Val Val Asp Leu Ala Asn Pro Asp Arg Ala
            35                  40                  45

Lys Leu Val Ser Gln Val Gly Ala Ala Cys Arg Ser His Gly Phe Phe
50                  55                  60

Gln Val Leu Asn His Gly Val Pro Val Glu Leu Thr Leu Ser Val Leu
65                  70                  75                  80

Ala Val Ala His Asp Phe Phe Arg Leu Pro Ala Glu Glu Lys Ala Lys
                85                  90                  95

Leu Tyr Ser Asp Asp Pro Ala Lys Lys Ile Arg Leu Ser Thr Ser Phe
            100                 105                 110

Asn Val Arg Lys Glu Thr Val His Asn Trp Arg Asp Tyr Leu Arg Leu
            115                 120                 125

His Cys Tyr Pro Leu His Arg Tyr Leu Pro Asp Trp Pro Ser Asn Pro
    130                 135                 140

Pro Ser Phe Arg Glu Ile Ile Ser Thr Tyr Cys Lys Glu Val Arg Glu
145                 150                 155                 160

Leu Gly Phe Arg Leu Tyr Gly Ala Ile Ser Glu Ser Leu Gly Leu Glu
                165                 170                 175

Gln Asp Tyr Ile Lys Lys Val Leu Gly Glu Gln Gln His Met Ala
            180                 185                 190

Val Asn Phe Tyr Pro Lys Cys Pro Glu Pro Leu Thr Phe Gly Leu
            195                 200                 205

Pro Ala His Thr Asp Pro Asn Ala Leu Thr Ile Leu Leu Met Asp Gln
    210                 215                 220

Gln Val Ala Gly Leu Gln Val Leu Lys Glu Gly Arg Trp Ile Ala Val
225                 230                 235                 240

Asn Pro Gln Pro Asn Ala Leu Val Ile Asn Ile Gly Asp Gln Leu Gln
            245                 250                 255

Ala Leu Ser Asn Gly Arg Tyr Lys Ser Val Trp His Arg Ala Val Val
            260                 265                 270

Asn Ser Asp Lys Ala Arg Met Ser Val Ala Ser Phe Leu Cys Pro Cys
275                 280                 285

Asn Asp Val Leu Ile Gly Pro Ala Gln Lys Leu Ile Thr Asp Gly Ser
    290                 295                 300

Pro Ala Val Tyr Arg Asn Tyr Thr Tyr Asp Glu Tyr Tyr Lys Lys Phe
305                 310                 315                 320

Trp Ser Arg Asn Leu Asp Gln Glu His Cys Leu Glu Leu Phe Arg Thr
                325                 330                 335

Thr Pro Thr Asp Thr Ser
            340

<210> SEQ ID NO 74
<211> LENGTH: 340
<212> TYPE: PRT
<213> ORGANISM: Oryza sativa

<400> SEQUENCE: 74

Met Ala Thr Thr Gln Leu Leu Ser Thr Val Glu His Arg Glu Thr Leu
1               5                   10                  15

Pro Glu Gly Tyr Ala Arg Pro Glu Ser Asp Arg Pro Arg Leu Ala Glu
            20                  25                  30
```

```
Val Ala Thr Asp Ser Asn Ile Pro Leu Ile Asp Leu Ala Ser Pro Asp
            35                  40                  45

Lys Pro Arg Val Ile Ala Glu Ile Ala Gln Ala Cys Arg Thr Tyr Gly
 50                  55                  60

Phe Phe Gln Val Thr Asn His Gly Ile Ala Glu Glu Leu Leu Glu Lys
 65                  70                  75                  80

Val Met Ala Val Ala Leu Glu Phe Phe Arg Leu Pro Pro Glu Glu Lys
            85                  90                  95

Glu Lys Leu Tyr Ser Asp Glu Pro Ser Lys Lys Ile Arg Leu Ser Thr
            100                 105                 110

Ser Phe Asn Val Arg Lys Glu Thr Val His Asn Trp Arg Asp Tyr Leu
            115                 120                 125

Arg Leu His Cys His Pro Leu Glu Glu Phe Val Pro Glu Trp Pro Ser
            130                 135                 140

Asn Pro Ala Gln Phe Lys Glu Ile Met Ser Thr Tyr Cys Arg Glu Val
145                 150                 155                 160

Arg Gln Leu Gly Leu Arg Leu Leu Gly Ala Ile Ser Val Ser Leu Gly
            165                 170                 175

Leu Glu Glu Asp Tyr Ile Glu Lys Val Leu Gly Glu Gln Glu Gln His
            180                 185                 190

Met Ala Val Asn Tyr Tyr Pro Arg Cys Pro Glu Pro Asp Leu Thr Tyr
            195                 200                 205

Gly Leu Pro Lys His Thr Asp Pro Asn Ala Leu Thr Ile Leu Leu Pro
            210                 215                 220

Asp Pro His Val Ala Gly Leu Gln Val Leu Arg Asp Gly Asp Gln Trp
225                 230                 235                 240

Ile Val Val Asn Pro Arg Pro Asn Ala Leu Val Val Asn Leu Gly Asp
            245                 250                 255

Gln Ile Gln Ala Leu Ser Asn Asp Ala Tyr Lys Ser Val Trp His Arg
            260                 265                 270

Ala Val Val Asn Pro Val Gln Glu Arg Met Ser Val Ala Ser Phe Met
            275                 280                 285

Cys Pro Cys Asn Ser Ala Val Ile Ser Pro Ala Arg Lys Leu Val Ala
            290                 295                 300

Asp Gly Asp Ala Pro Val Tyr Arg Ser Phe Thr Tyr Asp Glu Tyr Tyr
305                 310                 315                 320

Lys Lys Phe Trp Ser Arg Asn Leu Asp Gln Glu His Cys Leu Glu Leu
            325                 330                 335

Phe Lys Gly Gln
            340

<210> SEQ ID NO 75
<211> LENGTH: 338
<212> TYPE: PRT
<213> ORGANISM: Populus trichocarpa

<400> SEQUENCE: 75

Met Asp Thr Lys Val Leu Ser Ser Gly Ile Gln Tyr Thr Asn Leu Pro
1               5                   10                  15

Ala Ser Tyr Val Arg Pro Glu Ser Glu Arg Pro Arg Leu Trp Glu Val
            20                  25                  30

Ser Thr Cys Glu Asn Val Pro Val Ile Asp Leu Gly Cys Gln Glu Arg
            35                  40                  45

Asp Gln Ile Val Gln Gln Val Gly Asp Ala Cys Lys Asn Tyr Gly Phe
```

```
            50                  55                  60
Phe Gln Val Ile Asn His Gly Val Ser Leu Glu Ala Val Glu Lys Met
 65                  70                  75                  80

Leu Gly Val Ala His Asp Phe Phe Ser Leu Pro Val Glu Glu Lys Leu
                 85                  90                  95

Lys Leu Tyr Ser Asp Asp Pro Ser Lys Thr Met Arg Leu Ser Thr Ser
            100                 105                 110

Phe Asn Val Asn Lys Glu Lys Val His Asn Trp Arg Asp Tyr Leu Arg
            115                 120                 125

Leu His Cys Tyr Pro Leu Asp Lys Tyr Ala Pro Glu Trp Pro Ser Lys
            130                 135                 140

Pro Pro Phe Lys Asp Ile Val Ser Ser Tyr Cys Ile Gln Val Arg
145                 150                 155                 160

Glu Leu Gly Phe Arg Ile Gln Glu Leu Ile Ser Glu Ser Leu Gly Leu
                165                 170                 175

Glu Lys Asp His Val Lys Asn Val Leu Gly Glu Gln Gly Gln His Met
            180                 185                 190

Ala Val Asn Phe Tyr Pro Pro Cys Pro Glu Pro Glu Leu Thr Phe Gly
            195                 200                 205

Leu Pro Gly His Thr Asp Pro Asn Ala Leu Thr Ile Leu Leu Gln Asp
210                 215                 220

Gln Ser Val Ala Gly Leu Gln Val Leu Lys Asp Gly Lys Trp Val Ala
225                 230                 235                 240

Val Asp Pro His Pro Asp Ala Phe Val Ile Asn Ile Gly Asp Gln Leu
                245                 250                 255

Gln Ala Leu Ser Asn Gly Arg Tyr Lys Ser Val Trp His Arg Ala Ile
            260                 265                 270

Thr Asn Thr Asp Lys Ala Arg Met Ser Val Ala Ser Phe Leu Cys Pro
            275                 280                 285

Tyr Asp Asn Ala Leu Ile Thr Pro Pro Lys Ala Leu Thr Asp Asp Gly
            290                 295                 300

Thr Gly Ala Val Tyr Arg Asp Phe Thr Tyr Ala Glu Tyr Tyr Lys Lys
305                 310                 315                 320

Phe Trp Ser Arg Asp Leu Asp Gln Glu His Cys Leu Glu Leu Phe Lys
                325                 330                 335

Asn Lys

<210> SEQ ID NO 76
<211> LENGTH: 338
<212> TYPE: PRT
<213> ORGANISM: Populus trichocarpa

<400> SEQUENCE: 76

Met Asp Thr Lys Val Ile Ser Ser Gly Val His Tyr Thr Asn Leu Pro
  1               5                  10                  15

Ala Ser Tyr Val Arg Pro Glu Ser Glu Arg Pro Arg Leu Ser Glu Val
                 20                  25                  30

Ser Thr Cys Glu Asp Val Pro Val Ile Asp Leu Gly Cys Gln Asp Arg
             35                  40                  45

Asn Gln Ile Val Gln Val Gly Asp Ala Cys Glu His Tyr Gly Phe
            50                  55                  60

Phe Gln Val Ile Asn His Gly Val Ser Leu Glu Ala Val Glu Lys Met
 65                  70                  75                  80

Leu Gly Val Ala His Asp Phe Phe Ser Leu Pro Val Glu Glu Lys Leu
```

```
                     85                  90                  95
Lys Leu Tyr Ser Asp Asp Pro Ser Lys Thr Met Arg Leu Ser Thr Ser
                100                 105                 110

Phe Asn Val Asn Lys Glu Lys Val His Asn Trp Arg Asp Tyr Leu Arg
            115                 120                 125

Leu His Cys Tyr Pro Leu Asp Lys Tyr Val Pro Glu Trp Pro Ser Asn
        130                 135                 140

Pro Pro Pro Phe Lys Glu Ile Val Arg Ser Tyr Ser Ile Gln Val Arg
145                 150                 155                 160

Glu Leu Gly Phe Arg Ile Gln Glu Leu Ile Ser Glu Ser Leu Gly Leu
                165                 170                 175

Glu Lys Asp His Ile Lys Asn Val Leu Gly Glu Gly Gln His Met
            180                 185                 190

Ala Val Asn Phe Tyr Pro Pro Cys Pro Glu Pro Glu Leu Thr Tyr Gly
        195                 200                 205

Leu Pro Ala His Thr Asp Pro Asn Ala Leu Thr Ile Leu Leu Gln Asp
    210                 215                 220

Leu Ser Val Ala Gly Leu Gln Val Leu Leu Lys Asp Gly Lys Trp Val
225                 230                 235                 240

Ala Val Asn Pro His Pro Asp Ala Phe Val Ile Asn Ile Gly Asp Gln
                245                 250                 255

Leu Gln Ala Leu Ser Asn Gly Arg Tyr Lys Ser Val Trp His Arg Ala
            260                 265                 270

Ile Thr Asn Thr Asp Lys Ala Arg Met Ser Val Ala Ser Phe Leu Cys
        275                 280                 285

Pro Phe Asp Asn Ala Leu Ile Thr Pro Pro Lys Ala Leu Thr Asp Asp
    290                 295                 300

Gly Thr Gly Ala Ile Tyr Arg Asp Phe Thr Tyr Ala Glu Tyr Tyr Lys
305                 310                 315                 320

Lys Phe Trp Ser Arg Asn Leu Asp Gln Glu His Cys Leu Glu Leu Phe
                325                 330                 335

Lys Asn

<210> SEQ ID NO 77
<211> LENGTH: 337
<212> TYPE: PRT
<213> ORGANISM: Solanum lycopersicum

<400> SEQUENCE: 77

Met Glu Thr Lys Val Ile Ser Ser Gly Ile Asn His Ser Thr Leu Pro
1               5                   10                  15

Gln Ser Tyr Ile Arg Pro Glu Ser Asp Arg Pro Arg Leu Ser Glu Val
            20                  25                  30

Val Asp Cys Glu Asn Val Pro Ile Ile Asp Leu Ser Cys Gly Asp Gln
        35                  40                  45

Ala Gln Ile Ile Arg Gln Ile Gly Glu Ala Cys Gln Thr Tyr Gly Phe
    50                  55                  60

Phe Gln Val Ile Asn His Gly Val Pro Lys Glu Val Val Glu Lys Met
65                  70                  75                  80

Leu Gly Val Ala Gly Glu Phe Phe Asn Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Lys Lys Glu Thr Val His Asn Trp Arg Asp Tyr Leu Arg
        115                 120                 125
```

115                 120                 125
Leu His Cys Tyr Pro Leu Glu Lys Tyr Ala Pro Glu Trp Pro Ser Asn
130                 135                 140

Pro Ser Ser Phe Arg Glu Ile Val Ser Arg Tyr Cys Arg Glu Ile Arg
145                 150                 155                 160

Gln Leu Gly Phe Arg Leu Glu Glu Ala Ile Ala Glu Ser Leu Gly Leu
                165                 170                 175

Asp Lys Glu Cys Ile Lys Asp Val Leu Gly Glu Gln Gly Gln His Met
                180                 185                 190

Ala Ile Asn Tyr Tyr Pro Pro Cys Pro Gln Pro Glu Leu Thr Tyr Gly
            195                 200                 205

Leu Pro Ala His Thr Asp Pro Asn Ser Leu Thr Ile Leu Leu Gln Asp
210                 215                 220

Leu Gln Val Ala Gly Leu Gln Val Leu Lys Asp Gly Lys Trp Leu Ala
225                 230                 235                 240

Val Lys Pro Gln Pro Asp Ala Phe Val Ile Asn Leu Gly Asp Gln Leu
                245                 250                 255

Gln Ala Val Ser Asn Gly Lys Tyr Arg Ser Val Trp His Arg Ala Ile
            260                 265                 270

Val Asn Ser Asp Gln Ala Arg Met Ser Val Ala Ser Phe Leu Cys Pro
        275                 280                 285

Cys Asp Ser Ala Lys Ile Ser Ala Pro Lys Leu Leu Thr Glu Asp Gly
290                 295                 300

Ser Pro Val Ile Tyr Gln Asp Phe Thr Tyr Ala Glu Tyr Tyr Asn Lys
305                 310                 315                 320

Phe Trp Ser Arg Asn Leu Asp Gln Gln His Cys Leu Glu Leu Phe Lys
                325                 330                 335

Asn

<210> SEQ ID NO 78
<211> LENGTH: 342
<212> TYPE: PRT
<213> ORGANISM: Solanum lycopersicum

<400> SEQUENCE: 78

Met Thr Thr Thr Ser Val Leu Ser Ser Gly Phe Asn His Ser Thr Leu
1               5                   10                  15

Pro Gln Ser Tyr Val Arg Pro Glu Ser Gln Arg Pro Cys Met Ser Glu
                20                  25                  30

Val Val Asp Ser Asp Leu Val Pro Val Ile Asp Met Ser Cys Thr
            35                  40                  45

Asn Arg Asn Val Ile Val His Gln Ile Gly Glu Ala Cys Arg Leu Tyr
50                  55                  60

Gly Phe Phe Gln Val Ile Asn His Gly Val Ser Lys Lys Val Ile Asp
65                  70                  75                  80

Glu Met Leu Gly Val Ser His Glu Phe Phe Lys Leu Pro Val Glu Glu
                85                  90                  95

Lys Met Lys Leu Tyr Ser Asp Asp Pro Ser Lys Thr Met Arg Leu Ser
                100                 105                 110

Thr Ser Phe Asn Val Lys Lys Glu Thr Val His Asn Trp Arg Asp Tyr
            115                 120                 125

Leu Arg Leu His Cys Tyr Pro Leu Asp Lys Tyr Ala Pro Glu Trp Pro
130                 135                 140

Ser Asn Pro Pro Ser Phe Arg Glu Ile Val Ser Lys Tyr Cys Met Glu

```
                145                 150                 155                 160
        Val Arg Glu Leu Gly Tyr Arg Leu Glu Glu Ala Ile Ser Glu Ser Leu
                        165                 170                 175

Gly Leu Glu Lys Asp Cys Ile Lys Asn Val Leu Gly Glu Gln Gly Gln
                        180                 185                 190

His Met Ala Ile Asn Phe Tyr Pro Gln Cys Pro Gln Pro Glu Leu Thr
                        195                 200                 205

Tyr Gly Leu Pro Ala His Thr Asp Pro Asn Ala Ile Thr Ile Leu Leu
                        210                 215                 220

Gln Asp Leu Gln Val Ala Gly Leu Gln Val Leu Lys Asp Gly Lys Trp
        225                 230                 235                 240

Leu Ser Ile Lys Pro Gln Pro Asn Ala Phe Val Ile Asn Leu Gly Asp
                        245                 250                 255

Gln Leu Glu Ala Leu Ser Asn Gly Lys Tyr Lys Ser Ile Trp His Arg
                        260                 265                 270

Ala Ile Val Asn Ser Asp Lys Ala Arg Met Ser Val Ala Ser Phe Leu
                        275                 280                 285

Cys Pro Asn Asp Cys Ser Ile Ile Ser Ala Pro Lys Thr Leu Thr Glu
                        290                 295                 300

Asp Gly Ser Ser Ala Ile Tyr Arg His Phe Thr Tyr Ala Glu Tyr Tyr
        305                 310                 315                 320

Glu Lys Phe Trp Ser Arg Asn Leu Asp Gln Glu Tyr Cys Leu Glu Leu
                        325                 330                 335

Phe Lys Asn Asp Gly Thr
                        340

<210> SEQ ID NO 79
<211> LENGTH: 336
<212> TYPE: PRT
<213> ORGANISM: Sorghum bicolor

<400> SEQUENCE: 79

Met Ala Glu Gln Leu Leu Ser Thr Ala Val His Asp Thr Leu Pro Gly
        1               5                   10                  15

Ser Tyr Val Arg Pro Glu Ser Gln Arg Pro Arg Leu Ala Glu Val Val
                        20                  25                  30

Thr Gly Ala Arg Ile Pro Val Val Asp Leu Gly Ser Pro Asp Arg Ala
                        35                  40                  45

Ala Val Val Ala Ala Ile Gly Asp Ala Cys Arg Ser His Gly Phe Phe
                50                  55                  60

Gln Val Leu Asn His Gly Val His Ala Asp Leu Val Ala Ala Val Met
        65                  70                  75                  80

Ala Val Gly Arg Ala Phe Phe Arg Leu Ser Pro Glu Glu Lys Ala Lys
                        85                  90                  95

Leu Tyr Ser Asp Asp Pro Ala Arg Lys Ile Arg Leu Ser Thr Ser Phe
                        100                 105                 110

Asn Val Arg Lys Glu Thr Val His Asn Trp Arg Asp Tyr Leu Arg Leu
                        115                 120                 125

His Cys His Pro Leu Asp Glu Phe Val Pro Asp Trp Pro Ser Asn Pro
                        130                 135                 140

Pro Asp Phe Lys Asp Thr Met Ser Thr Tyr Cys Lys Glu Val Arg Glu
        145                 150                 155                 160

Leu Gly Phe Arg Leu Tyr Ala Ala Ile Ser Glu Ser Leu Gly Leu Glu
                        165                 170                 175
```

Ala Ser Tyr Met Lys Glu Thr Leu Gly Glu Gln Glu Gln His Met Ala
            180                 185                 190

Val Asn Phe Tyr Pro Pro Cys Pro Glu Pro Glu Leu Thr Tyr Gly Leu
        195                 200                 205

Pro Ala His Thr Asp Pro Asn Ala Leu Thr Ile Leu Leu Met Asp Gln
    210                 215                 220

Asp Val Ala Gly Leu Gln Val Leu His Gly Gly Lys Trp Val Ala Val
225                 230                 235                 240

Asn Pro Gln Pro Gly Ala Leu Ile Ile Asn Ile Gly Asp Gln Leu Gln
                245                 250                 255

Ala Leu Ser Asn Gly Gln Tyr Arg Ser Val Trp His Arg Ala Val Val
            260                 265                 270

Asn Ser Asp Arg Glu Arg Met Ser Val Ala Ser Phe Leu Cys Pro Cys
        275                 280                 285

Asn His Val Val Leu Gly Pro Ala Lys Lys Leu Val Thr Glu Asp Thr
    290                 295                 300

Pro Ala Val Tyr Arg Ser Tyr Thr Tyr Asp Glu Tyr Tyr Lys Lys Phe
305                 310                 315                 320

Trp Ser Arg Asn Leu Asp Gln Glu His Cys Leu Glu Leu Phe Arg Thr
                325                 330                 335

<210> SEQ ID NO 80
<211> LENGTH: 1020
<212> TYPE: DNA
<213> ORGANISM: Spinacia oleracea

<400> SEQUENCE: 80
atggcaaaca agatattatc caccggaatt ccttacaaaa ccctccccga agctacatc        60 cgacccgaaa atgagaggcc caacttatct caagtctccg attgcgagaa tgtccctgtt      120
attgacttgg gtgccaaaga ccgtactcaa acaatccacc aagtcttcaa tgcttgtaaa      180
aattacgggt ttttccaggt gattaatcat ggggtgtcaa aggaattagc ggagaagatg      240
caaaaggtag ctcgagagtt cttcgatatg tcggttgagg aaaaaatgaa attatatagt      300
gacgatccaa ctaaaacact aagattgtct acaagtttta cgttaacaa agaggaagtt       360 cataattgga gagattatct taggctccat tgttggcctc ttgagcaata tgtccccgaa      420
tggccttcta accccccttc cttcaaggaa atagtgagca agtacataaa agaagttagg      480
gaacttggtt tcagagtcca agaactaata tcagagagtt tagggttgga gaaagattac      540
ataaagaatg tcctaggaga tcaaggacaa cacatggctc ttaattatta ccctgagtgc      600
ccggagccag agatgacata cgggttgccg ggtcatactg accctaatgc ccttaccatc      660
cttctccaag acttgcaagt atctggcctt caaattttta aggatggtaa atggcttgct      720
gtcaaacctc aacctgatgc ttttgtcatt aacattggtg atcaattgca ggcattaagt      780
aacggtatat acaagagtgt atggcacaga gcagttgtga acacagataa gccaagatta      840
tcagtagctt cattcctctg ccccgccaat gatgcgttga taagcgcgcc aacacctctg      900
accgccaacg atcaccggc tgtatataga gactatacgt atcctgagta ctacaagact       960
ttctggagta ggaacttgga ccaagagcac tgcttggagc ttttaaaaa ccaaacctag      1020

<210> SEQ ID NO 81
<211> LENGTH: 339
<212> TYPE: PRT
<213> ORGANISM: Spinacia oleracea

<400> SEQUENCE: 81

Met Ala Asn Lys Ile Leu Ser Thr Gly Ile Pro Tyr Lys Thr Leu Pro
1               5                   10                  15

Glu Ser Tyr Ile Arg Pro Glu Asn Arg Pro Asn Leu Ser Gln Val
            20                  25                  30

Ser Asp Cys Glu Asn Val Pro Val Ile Asp Leu Gly Ala Lys Asp Arg
                35                  40                  45

Thr Gln Thr Ile His Gln Val Phe Asn Ala Cys Lys Asn Tyr Gly Phe
    50                  55                  60

Phe Gln Val Ile Asn His Gly Val Ser Lys Glu Leu Ala Glu Lys Met
65                  70                  75                  80

Gln Lys Val Ala Arg Glu Phe Phe Asp Met Ser Val Glu Glu Lys Met
                85                  90                  95

Lys Leu Tyr Ser Asp Asp Pro Thr Lys Thr Leu Arg Leu Ser Thr Ser
                100                 105                 110

Phe Asn Val Asn Lys Glu Glu Val His Asn Trp Arg Asp Tyr Leu Arg
            115                 120                 125

Leu His Cys Trp Pro Leu Glu Gln Tyr Val Pro Glu Trp Pro Ser Asn
    130                 135                 140

Pro Pro Ser Phe Lys Glu Ile Val Ser Lys Tyr Ile Lys Glu Val Arg
145                 150                 155                 160

Glu Leu Gly Phe Arg Val Gln Glu Leu Ile Ser Glu Ser Leu Gly Leu
                165                 170                 175

Glu Lys Asp Tyr Ile Lys Asn Val Leu Gly Asp Gln Gly Gln His Met
                180                 185                 190

Ala Leu Asn Tyr Tyr Pro Glu Cys Pro Glu Pro Glu Met Thr Tyr Gly
            195                 200                 205

Leu Pro Gly His Thr Asp Pro Asn Ala Leu Thr Ile Leu Leu Gln Asp
    210                 215                 220

Leu Gln Val Ser Gly Leu Gln Ile Phe Lys Asp Gly Lys Trp Leu Ala
225                 230                 235                 240

Val Lys Pro Gln Pro Asp Ala Phe Val Ile Asn Ile Gly Asp Gln Leu
                245                 250                 255

Gln Ala Leu Ser Asn Gly Ile Tyr Lys Ser Val Trp His Arg Ala Val
            260                 265                 270

Val Asn Thr Asp Lys Pro Arg Leu Ser Val Ala Ser Phe Leu Cys Pro
    275                 280                 285

Ala Asn Asp Ala Leu Ile Ser Ala Pro Thr Pro Leu Thr Ala Asn Gly
    290                 295                 300

Ser Pro Ala Val Tyr Arg Asp Tyr Thr Tyr Pro Glu Tyr Tyr Lys Thr
305                 310                 315                 320

Phe Trp Ser Arg Asn Leu Asp Gln Glu His Cys Leu Glu Leu Phe Lys
                325                 330                 335

Asn Gln Thr

<210> SEQ ID NO 82
<211> LENGTH: 338
<212> TYPE: PRT
<213> ORGANISM: Vitis sp.

<400> SEQUENCE: 82

Met Glu Ser Lys Val Leu Ser Thr Gly Ile Arg Tyr Leu Thr Leu Pro
1               5                   10                  15

Gln Ser Tyr Ile Arg Pro Glu Pro Glu Arg Pro Arg Leu Ser Gln Val
            20                  25                  30

Ser Glu Cys Lys His Val Pro Ile Ile Asp Leu Gly Lys Asp Val Asn
            35                  40                  45

Arg Ala Gln Leu Ile Gln His Ile Ala Asp Ala Cys Arg Leu Tyr Gly
        50                  55                  60

Phe Phe Gln Val Ile Asn His Gly Val Ala Ala Glu Met Met Glu Lys
65                  70                  75                  80

Met Leu Glu Val Ala Asp Glu Phe Tyr Arg Leu Pro Val Glu Glu Lys
                85                  90                  95

Met Lys Leu Tyr Ser Asp Asp Pro Thr Lys Thr Met Arg Leu Ser Thr
            100                 105                 110

Ser Phe Asn Val Asn Lys Glu Lys Val His Asn Trp Arg Asp Tyr Leu
        115                 120                 125

Arg Leu His Cys Tyr Pro Leu Asp Gln Tyr Thr Pro Glu Trp Pro Ser
    130                 135                 140

Asn Pro Pro Ser Phe Lys Glu Ile Val Ser Ser Tyr Cys Lys Glu Val
145                 150                 155                 160

Arg Glu Leu Gly Phe Arg Leu Gln Glu Met Ile Ser Glu Ser Leu Gly
                165                 170                 175

Leu Glu Lys Asp His Ile Lys Asn Val Phe Gly Glu Gln Gly Gln His
            180                 185                 190

Met Ala Val Asn Tyr Tyr Pro Pro Cys Pro Gln Pro Glu Leu Thr Tyr
        195                 200                 205

Gly Leu Pro Gly His Thr Asp Pro Asn Ala Leu Thr Ile Leu Leu Gln
    210                 215                 220

Asp Leu Arg Val Ala Gly Leu Gln Val Leu Lys Asp Gly Thr Trp Leu
225                 230                 235                 240

Ala Ile Lys Pro His Pro Gly Ala Phe Val Val Asn Ile Gly Asp Gln
                245                 250                 255

Leu Gln Ala Val Ser Asn Gly Lys Tyr Lys Ser Val Trp His Arg Ala
            260                 265                 270

Val Val Asn Ala Glu Ser Glu Arg Leu Ser Val Ala Ser Phe Leu Cys
        275                 280                 285

Pro Cys Asn Asp Ala Val Ile Gly Pro Ala Lys Pro Leu Thr Glu Asp
    290                 295                 300

Gly Ser Ala Pro Ile Tyr Lys Asn Phe Thr Tyr Ala Glu Tyr Tyr Lys
305                 310                 315                 320

Lys Phe Trp Gly Arg Asp Leu Asp Gln Glu His Cys Leu Glu Leu Phe
                325                 330                 335

Lys Asn

<210> SEQ ID NO 83
<211> LENGTH: 336
<212> TYPE: PRT
<213> ORGANISM: Zea mays

<400> SEQUENCE: 83

Met Ala Glu His Leu Leu Ser Thr Ala Val His Asp Thr Leu Pro Gly
1               5                   10                  15

Ser Tyr Val Arg Pro Glu Pro Glu Arg Pro Arg Leu Ala Glu Val Val
            20                  25                  30

Thr Gly Ala Arg Ile Pro Val Val Asp Leu Gly Ser Pro Asp Arg Gly
        35                  40                  45

Ala Val Val Ala Ala Val Gly Asp Ala Cys Arg Ser His Gly Phe Phe
    50                  55                  60

Gln Val Val Asn His Gly Ile His Ala Leu Val Ala Val Met
65                  70                  75                  80

Ala Ala Gly Arg Gly Phe Phe Arg Leu Pro Pro Glu Glu Lys Ala Lys
                85                  90                  95

Leu Tyr Ser Asp Asp Pro Ala Arg Lys Ile Arg Leu Ser Thr Ser Phe
            100                 105                 110

Asn Val Arg Lys Glu Thr Val His Asn Trp Arg Asp Tyr Leu Arg Leu
        115                 120                 125

His Cys His Pro Leu Asp Glu Phe Leu Pro Asp Trp Pro Ser Asn Pro
    130                 135                 140

Pro Asp Phe Lys Glu Thr Met Gly Thr Tyr Cys Lys Glu Val Arg Glu
145                 150                 155                 160

Leu Gly Phe Arg Leu Tyr Ala Ala Ile Ser Glu Ser Leu Gly Leu Glu
                165                 170                 175

Ala Ser Tyr Met Lys Glu Ala Leu Gly Glu Gln Glu Gln His Met Ala
            180                 185                 190

Val Asn Phe Tyr Pro Pro Cys Pro Glu Pro Glu Leu Thr Tyr Gly Leu
        195                 200                 205

Pro Ala His Thr Asp Pro Asn Ala Leu Thr Ile Leu Leu Met Asp Pro
    210                 215                 220

Asp Val Ala Gly Leu Gln Val Leu His Ala Gly Gln Trp Val Ala Val
225                 230                 235                 240

Asn Pro Gln Pro Gly Ala Leu Ile Ile Asn Ile Gly Asp Gln Leu Gln
                245                 250                 255

Ala Leu Ser Asn Gly Gln Tyr Arg Ser Val Trp His Arg Ala Val Val
            260                 265                 270

Asn Ser Asp Arg Glu Arg Met Ser Val Ala Ser Phe Leu Cys Pro Cys
        275                 280                 285

Asn His Val Val Leu Gly Pro Ala Arg Lys Leu Val Thr Glu Asp Thr
    290                 295                 300

Pro Ala Val Tyr Arg Asn Tyr Thr Tyr Asp Lys Tyr Tyr Ala Lys Phe
305                 310                 315                 320

Trp Ser Arg Asn Leu Asp Gln Glu His Cys Leu Glu Leu Phe Arg Thr
                325                 330                 335

<210> SEQ ID NO 84
<211> LENGTH: 346
<212> TYPE: PRT
<213> ORGANISM: Zingiber officinale

<400> SEQUENCE: 84

Met Ala Asp Met Leu Leu Ser Ile Gly Glu His Asp Thr Met Pro Arg
1               5                   10                  15

Asn Tyr Val Arg Pro Glu Asn Glu Arg Pro His Leu Asp Asn Val Ile
                20                  25                  30

Ala Asp Ala Asn Ile Pro Val Val Asp Phe Gly Ala Pro Asp Lys Ser
            35                  40                  45

Gln Ile Ile Ser Gln Ile Glu Lys Ala Cys Arg Leu Tyr Gly Phe Phe
        50                  55                  60

Gln Val Val Asn His Gly Ile Ala Ala Glu Leu Ile Lys Lys Val Leu
65                  70                  75                  80

Ala Ile Ala Leu Glu Phe Phe Arg Leu Pro Gln Glu Glu Lys Ala Lys
                85                  90                  95

Leu Tyr Ser Asp Asp Pro Ala Lys Lys Ile Arg Leu Ser Thr Ser Phe

|   |   |   | 100 |   |   |   | 105 |   |   |   | 110 |
|---|---|---|---|---|---|---|---|---|---|---|---|

Asn Val Arg Lys Glu Thr Val His Asn Trp Arg Asp Tyr Leu Arg Leu
        115                  120                  125

His Cys Tyr Pro Leu Glu Glu Phe Ile Pro Asp Trp Pro Ser Asn Pro
 130                 135                  140

Ser Ser Phe Lys Asp Val Phe Gly Ser Tyr Cys Gln Gln Val Arg Lys
145                 150                  155                  160

Leu Gly Phe Arg Ile Leu Gly Ile Ile Ser Leu Ser Leu Gly Leu Glu
                  165                  170                  175

Glu Glu Tyr Leu Val Arg Val Leu Gly Glu Gln Glu Gln His Met Ala
                  180                  185                  190

Val Asn Tyr Tyr Pro Lys Cys Pro Glu Pro Glu Leu Thr Tyr Gly Leu
                  195                  200                  205

Pro Ala His Thr Asp Pro Asn Ala Leu Thr Ile Leu Leu Gln Asp Pro
210                 215                  220

His Val Ser Gly Leu Gln Val His Lys Asp Gly Lys Trp Ile Ala Val
225                 230                  235                  240

Asp Pro Lys Pro Asn Ala Phe Val Ile Asn Ile Gly Asp Gln Leu Gln
                  245                  250                  255

Ala Leu Ser Asn Gly Arg Tyr Lys Ser Val Trp His Arg Ala Val Val
                  260                  265                  270

Asn Ser Asn Lys Glu Arg Met Ser Val Ala Ser Phe Leu Cys Pro Cys
                  275                  280                  285

Asn Ser Val Leu Ile Ser Pro Pro Glu Lys Leu Ile Ala Asp Gly Cys
                  290                  295                  300

Pro Ala Val Tyr Arg Ser Tyr Thr Tyr Asp Glu Tyr Tyr Lys Lys Phe
305                 310                  315                  320

Trp Ser Arg Asn Leu Asp Gln Glu His Cys Leu Glu Leu Phe Lys Lys
                  325                  330                  335

Glu Arg Glu Thr Cys Pro Asp Ala Pro Thr
                  340                  345

```
<210> SEQ ID NO 85
<211> LENGTH: 22
<212> TYPE: DNA
<213> ORGANISM: Artificial
<220> FEATURE:
<223> OTHER INFORMATION: forward primer AtDMR6_fw

<400> SEQUENCE: 85
caccatggcg gcaaagctga ta                                              22

<210> SEQ ID NO 86
<211> LENGTH: 21
<212> TYPE: DNA
<213> ORGANISM: Artificial
<220> FEATURE:
<223> OTHER INFORMATION: backward primer AtDMR6UTR_rv

<400> SEQUENCE: 86
gacaaacaca aaggccaaag a                                               21

<210> SEQ ID NO 87
<211> LENGTH: 24
<212> TYPE: DNA
<213> ORGANISM: Artificial
<220> FEATURE:
<223> OTHER INFORMATION: forward primer cuc_fw
```

-continued

<400> SEQUENCE: 87
caccatgagc agtgtgatgg agat                                                24

<210> SEQ ID NO 88
<211> LENGTH: 20
<212> TYPE: DNA
<213> ORGANISM: Artificial
<220> FEATURE:
<223> OTHER INFORMATION: backward primer cucUTR_rv

<400> SEQUENCE: 88
tgggccaaaa agtttatcca                                                     20

<210> SEQ ID NO 89
<211> LENGTH: 27
<212> TYPE: DNA
<213> ORGANISM: Artificial
<220> FEATURE:
<223> OTHER INFORMATION: forward primer spi_fw

<400> SEQUENCE: 89
caccatggca aacaagatat tatccac                                             27

<210> SEQ ID NO 90
<211> LENGTH: 22
<212> TYPE: DNA
<213> ORGANISM: Artificial
<220> FEATURE:
<223> OTHER INFORMATION: backward primer spiUTR_rv

<400> SEQUENCE: 90
ttgctgccta caaaagtaca aa                                                  22

<210> SEQ ID NO 91
<211> LENGTH: 24
<212> TYPE: DNA
<213> ORGANISM: Artificial
<220> FEATURE:
<223> OTHER INFORMATION: forward primer Lsat_fw

<400> SEQUENCE: 91
caccatggcc gcaaaagtca tctc                                                24

<210> SEQ ID NO 92
<211> LENGTH: 22
<212> TYPE: DNA
<213> ORGANISM: Artificial
<220> FEATURE:
<223> OTHER INFORMATION: backward primer LsatUTR_rv

<400> SEQUENCE: 92
catggaaaca catattcctt ca                                                  22

<210> SEQ ID NO 93
<211> LENGTH: 28
<212> TYPE: DNA
<213> ORGANISM: Artificial
<220> FEATURE:
<223> OTHER INFORMATION: forward primer Slycldmr6_fw

<400> SEQUENCE: 93
caccatggaa accaaagtta tttctagc                                            28

<210> SEQ ID NO 94
<211> LENGTH: 20

```
<212> TYPE: DNA
<213> ORGANISM: Artificial
<220> FEATURE:
<223> OTHER INFORMATION: backward primer SlycldmrGUTR_rv

<400> SEQUENCE: 94
gggacatccc tatgaaccaa                                              20

<210> SEQ ID NO 95
<211> LENGTH: 1013
<212> TYPE: DNA
<213> ORGANISM: Solanum lycopersicum

<400> SEQUENCE: 95
atggaaacca aagttatttc tagcggaatc aaccactcta ctcttcctca agttacatc    60
cgacccgaat ccgatagacc acgtctatcg gaagtggtcg attgtgaaaa tgttccaata  120
attgacttaa gttgcggaga tcaagctcaa ataattcgtc aaattggaga agcttgtcaa  180
acttatggtt tctttcaggt aattaatcat ggtgtaccaa aggaagttgt agagaaaatg  240
ctaggggtag ctggggaatt tttcaattta ccagtagaag agaaactaaa attatattca  300
gatgatcctt caaagaccat gagattatca acaagtttta atgttaaaaa ggagacagtt  360
cataattgga gagattatct cagacttcat tgttatcctc tagagaagta tgctcctgaa  420
tggccttcta atccatcatc tttcagggaa atcgtgagca gatattgcag ggaaattcgt  480
caactcggat ttagattaga agaagccata gcagaaagcc tggggttaga taaagagtgt  540
ataaaagatg tattgggtga acaaggacaa catatggcta tcaattatta tcctccttgt  600
ccacaaccag aacttactta tgggcttccg gcccatactg atccaaattc acttacaatt  660
cttcttcaag acttgcaagt tgcgggtctt caagttctta agatggcaa atggttagct  720
gtaaaacctc aacctgacgc ctttgtcatt aatcttgggg atcaattgca ggcagtaagt  780
aacggtaagt acagaagtgt atggcatcga gctattgtga attcagatca agctaggatg  840
tcagtggctt cgtttctatg tccgtgtgat agcgcgaaaa tcagtgcacc aaagctgctg  900
acagaagatg gatctccagt gatttatcaa gactttacgt atgctgagta ttacaacaag  960
ttctggagca ggaatttgga ccagcaacat tgtttggaac ttttcaagaa taa          1013

<210> SEQ ID NO 96
<211> LENGTH: 337
<212> TYPE: PRT
<213> ORGANISM: Solanum lycopersicum

<400> SEQUENCE: 96

Met Glu Thr Lys Val Ile Ser Ser Gly Ile Asn His Ser Thr Leu Pro
1               5                   10                  15

Gln Ser Tyr Ile Arg Pro Glu Ser Asp Arg Pro Arg Leu Ser Glu Val
            20                  25                  30

Val Asp Cys Glu Asn Val Pro Ile Ile Asp Leu Ser Cys Gly Asp Gln
        35                  40                  45

Ala Gln Ile Ile Arg Gln Ile Gly Glu Ala Cys Gln Thr Tyr Gly Phe
    50                  55                  60

Phe Gln Val Ile Asn His Gly Val Pro Lys Glu Val Val Glu Lys Met
65                  70                  75                  80

Leu Gly Val Ala Gly Glu Phe Phe Asn Leu Pro Val Glu Glu Lys Leu
                85                  90                  95

Lys Leu Tyr Ser Asp Asp Pro Ser Lys Thr Met Arg Leu Ser Thr Ser
            100                 105                 110
```

```
Phe Asn Val Lys Lys Glu Thr Val His Asn Trp Arg Asp Tyr Leu Arg
            115                 120                 125
Leu His Cys Tyr Pro Leu Glu Lys Tyr Ala Pro Glu Trp Pro Ser Asn
        130                 135                 140
Pro Ser Ser Phe Arg Glu Ile Val Ser Arg Tyr Cys Arg Glu Ile Arg
145                 150                 155                 160
Gln Leu Gly Phe Arg Leu Glu Glu Ala Ile Ala Glu Ser Leu Gly Leu
                165                 170                 175
Asp Lys Glu Cys Ile Lys Asp Val Leu Gly Gln Gly Gln His Met
            180                 185                 190
Ala Ile Asn Tyr Tyr Pro Pro Cys Pro Gln Pro Glu Leu Thr Tyr Gly
        195                 200                 205
Leu Pro Ala His Thr Asp Pro Asn Ser Leu Thr Ile Leu Leu Gln Asp
210                 215                 220
Leu Gln Val Ala Gly Leu Gln Val Leu Lys Asp Gly Lys Trp Leu Ala
225                 230                 235                 240
Val Lys Pro Gln Pro Asp Ala Phe Val Ile Asn Leu Gly Asp Gln Leu
                245                 250                 255
Gln Ala Val Ser Asn Gly Lys Tyr Arg Ser Val Trp His Arg Ala Ile
            260                 265                 270
Val Asn Ser Asp Gln Ala Arg Met Ser Val Ala Ser Phe Leu Cys Pro
        275                 280                 285
Cys Asp Ser Ala Lys Ile Ser Ala Pro Lys Leu Leu Thr Glu Asp Gly
290                 295                 300
Ser Pro Val Ile Tyr Gln Asp Phe Thr Tyr Ala Glu Tyr Tyr Asn Lys
305                 310                 315                 320
Phe Trp Ser Arg Asn Leu Asp Gln Gln His Cys Leu Glu Leu Phe Lys
                325                 330                 335
Asn
```

<210> SEQ ID NO 97
<211> LENGTH: 1014
<212> TYPE: DNA
<213> ORGANISM: Nicotiana benthamiana

<400> SEQUENCE: 97

```
atggaagcaa aagttctttc cagcggaatc cgccactcta ctatccctca aagttacatc      60
cgccctcaat ccgataggcc gcgccttcct gaagttgctg attgtgaaaa cgttccagta     120
gttgatatag gttgcggtga tagaaacctt attgttcatc aaattggtga agcctgtcgt     180
ctttatggtt ttttccaggt aattaatcat ggtgtaccaa gaatttaat agacgaaatg      240
ctagagatag ctggggaatt ttttaggctt ccagttgaag agaagttgaa attgtactca     300
gatgacccat cgaagacgat gagattgtcg actagttta atgtgaaaaa ggagaaggtt      360
cacaattgga gagattatct cagacttcat tgttatcctc ttgaaaatta cgctcctgaa     420
tggccttcca atccttcctc tttcagggaa atcgtgagca gatattgcat ggaagttcga     480
caactcgggt tcagattgca ggaagccata gcagagagcc taggcttaga gaaagagtgt     540
ataaaggatg tattgggcga acaaggtcaa cacatggcta tcaatttcta tcctccttgt     600
ccacaaccag aactcactta tgggctgcca gcacatactg atccaaatgc ccttacaatt     660
cttcttcaag acttagaagt agctggtctt caagttctta agatggcga atggttggcc      720
gtcaagcctc aaccagatgc ctttgtcatt aatcttggtg atcaactgca ggcagtgagt     780
```

```
aatgggagat acaaaagcgt atggcatcga gctattgtaa attcagacaa agccaggttg    840
tcagtggctt cgttcctttg tccgtgcgat agcgcgaaaa tcagtgctcc aaagctcctc    900
actgaagatg gatctcctgt catttatcag gactttacct atgctgagta ttacaaaaag    960
ttctggagca ggaatttgga ccaggaacat tgtttggaac ttttcaagaa ctaa         1014
```

<210> SEQ ID NO 98
<211> LENGTH: 337
<212> TYPE: PRT
<213> ORGANISM: Nicotiana benthamiana

<400> SEQUENCE: 98

```
Met Glu Ala Lys Val Leu Ser Ser Gly Ile Arg His Ser Thr Ile Pro
1               5                   10                  15

Gln Ser Tyr Ile Arg Pro Gln Ser Asp Arg Pro Arg Leu Ser Glu Val
            20                  25                  30

Ala Asp Cys Glu Asn Val Pro Val Asp Ile Gly Cys Gly Asp Arg
        35                  40                  45

Asn Leu Ile Val His Gln Ile Gly Glu Ala Cys Arg Leu Tyr Gly Phe
    50                  55                  60

Phe Gln Val Ile Asn His Gly Val Pro Lys Asn Leu Ile Asp Glu Met
65                  70                  75                  80

Leu Glu Ile Ala Gly Glu Phe Phe Arg Leu Pro Val Glu Glu Lys Leu
                85                  90                  95

Lys Leu Tyr Ser Asp Asp Pro Ser Lys Thr Met Arg Leu Ser Thr Ser
            100                 105                 110

Phe Asn Val Lys Lys Glu Lys Val His Asn Trp Arg Asp Tyr Leu Arg
        115                 120                 125

Leu His Cys Tyr Pro Leu Glu Asn Tyr Ala Pro Glu Trp Pro Ser Asn
    130                 135                 140

Pro Ser Ser Phe Arg Glu Ile Val Ser Arg Tyr Cys Met Glu Val Arg
145                 150                 155                 160

Gln Leu Gly Phe Arg Leu Gln Glu Ala Ile Ala Glu Ser Leu Gly Leu
                165                 170                 175

Glu Lys Glu Cys Ile Lys Asp Val Leu Gly Glu Gln Gly Gln His Met
            180                 185                 190

Ala Ile Asn Phe Tyr Pro Pro Cys Pro Gln Pro Glu Leu Thr Tyr Gly
        195                 200                 205

Leu Pro Ala His Thr Asp Pro Asn Ala Leu Thr Ile Leu Leu Gln Asp
    210                 215                 220

Leu Glu Val Ala Gly Leu Gln Val Leu Lys Asp Gly Glu Trp Leu Ala
225                 230                 235                 240

Val Lys Pro Gln Pro Asp Ala Phe Val Ile Asn Leu Gly Asp Gln Leu
                245                 250                 255

Gln Ala Val Ser Asn Gly Arg Tyr Lys Ser Val Trp His Arg Ala Ile
            260                 265                 270

Val Asn Ser Asp Lys Ala Arg Leu Ser Val Ala Ser Phe Leu Cys Pro
        275                 280                 285

Cys Asp Ser Ala Lys Ile Ser Ala Pro Lys Leu Leu Thr Glu Asp Gly
    290                 295                 300

Ser Pro Val Ile Tyr Gln Asp Phe Thr Tyr Ala Glu Tyr Tyr Lys Lys
305                 310                 315                 320

Phe Trp Ser Arg Asn Leu Asp Gln Glu His Cys Leu Glu Leu Phe Lys
                325                 330                 335
```

Asn

<210> SEQ ID NO 99
<211> LENGTH: 1026
<212> TYPE: DNA
<213> ORGANISM: Arabidopsis thaliana

<400> SEQUENCE: 99

```
atggcggcaa agctgatatc caccggtttc cgtcatacta ctttgccgga aaactatgtc      60
cggccaatct ccgaccgtcc acgtctctct gaagtctctc aactcgaaga tttccctctc     120
atcgatctct cttccactga tcgatctttt ctcatccaac aaatccacca agcttgtgcc     180
cgattcggat tttttcaggt cataaatcac ggagttaaca aacaaataat agatgagatg     240
gtgagtgttg cgcgtgagtt ctttagcatg tctatggaag aaaaaatgaa gctatattca     300
gacgatccaa cgaagacaac aagattatcg acgagcttca atgtgaagaa agaagaagtc     360
aacaattgga gagactatct aagactccat tgttatccta ccacaagta  tgtcaatgag     420
tggccgtcaa accctccttc tttcaaggaa atagtaagta atacagtag  agaagtaaga     480
gaagtgggat ttaaaataga ggaattaata tcagagagct taggtttaga aaaagattac     540
atgaagaaag tgcttggtga acaaggtcaa cacatggcag tcaactatta tcctccatgt     600
cctgaacctg agctcactta cggtttacct gctcataccg acccaaacgc cctaaccatt     660
cttcttcaag acactactgt ttgcggtctc cagatcttga tcgacggtca gtggttcgcc     720
gttaatccac atcctgatgc ttttgtcatc aacataggtg accagttaca ggcattaagt     780
aatggagtat acaaaagtgt ttggcatcgc gctgtaacaa acacagaaaa tccgagacta     840
tcggtcgcat cgtttctgtg cccagctgac tgtgctgtca tgagcccggc caagcccttg     900
tgggaagctg aggacgatga aacgaaacca gtctacaaag atttcactta tgcagagtat     960
tacaagaagt tttggagtag gaatctggac caagaacatt gcctcgagaa ttttctaaac    1020
aactaa                                                              1026
```

<210> SEQ ID NO 100
<211> LENGTH: 341
<212> TYPE: PRT
<213> ORGANISM: Arabidopsis thaliana

<400> SEQUENCE: 100

```
Met Ala Ala Lys Leu Ile Ser Thr Gly Phe Arg His Thr Thr Leu Pro
1               5                   10                  15

Glu Asn Tyr Val Arg Pro Ile Ser Asp Arg Pro Arg Leu Ser Glu Val
            20                  25                  30

Ser Gln Leu Glu Asp Phe Pro Leu Ile Asp Leu Ser Ser Thr Asp Arg
        35                  40                  45

Ser Phe Leu Ile Gln Gln Ile His Gln Ala Cys Ala Arg Phe Gly Phe
    50                  55                  60

Phe Gln Val Ile Asn His Gly Val Asn Lys Gln Ile Ile Asp Glu Met
65                  70                  75                  80

Val Ser Val Ala Arg Glu Phe Phe Ser Met Ser Met Glu Glu Lys Met
                85                  90                  95

Lys Leu Tyr Ser Asp Asp Pro Thr Lys Thr Thr Arg Leu Ser Thr Ser
            100                 105                 110

Phe Asn Val Lys Lys Glu Glu Val Asn Asn Trp Arg Asp Tyr Leu Arg
        115                 120                 125

Leu His Cys Tyr Pro Ile His Lys Tyr Val Asn Glu Trp Pro Ser Asn
```

```
                130                 135                 140
Pro Pro Ser Phe Lys Glu Ile Val Ser Lys Tyr Ser Arg Glu Val Arg
145                 150                 155                 160

Glu Val Gly Phe Lys Ile Glu Leu Ile Ser Glu Ser Leu Gly Leu
                165                 170                 175

Glu Lys Asp Tyr Met Lys Lys Val Leu Gly Glu Gly Gln His Met
                180                 185                 190

Ala Val Asn Tyr Tyr Pro Pro Cys Pro Glu Pro Glu Leu Thr Tyr Gly
                195                 200                 205

Leu Pro Ala His Thr Asp Pro Asn Ala Leu Thr Ile Leu Leu Gln Asp
            210                 215                 220

Thr Thr Val Cys Gly Leu Gln Ile Leu Ile Asp Gly Gln Trp Phe Ala
225                 230                 235                 240

Val Asn Pro His Pro Asp Ala Phe Val Ile Asn Ile Gly Asp Gln Leu
                245                 250                 255

Gln Ala Leu Ser Asn Gly Val Tyr Lys Ser Val Trp His Arg Ala Val
                260                 265                 270

Thr Asn Thr Glu Asn Pro Arg Leu Ser Val Ala Ser Phe Leu Cys Pro
                275                 280                 285

Ala Asp Cys Ala Val Met Ser Pro Ala Lys Pro Leu Trp Glu Ala Glu
            290                 295                 300

Asp Asp Glu Thr Lys Pro Val Tyr Lys Asp Phe Thr Tyr Ala Glu Tyr
305                 310                 315                 320

Tyr Lys Lys Phe Trp Ser Arg Asn Leu Asp Gln Glu His Cys Leu Glu
                325                 330                 335

Asn Phe Leu Asn Asn
            340

<210> SEQ ID NO 101
<211> LENGTH: 1014
<212> TYPE: DNA
<213> ORGANISM: Lactuca sativa

<400> SEQUENCE: 101
atggccgcaa aagtcatctc cagtggattc cggtatacta ctctaccgga gagctacgtc      60
cgtccggtta acgacagacc taacctatct caagtttccg attgcaacga cgttcctgtt     120
attgacatcg gttgtggtga tagacaactc ataagccaac aaattggcga tgcttgtaga     180
agatacggtt ttttccaggt gattaatcat ggtgtgcctg atgaaatagt ggagaaaatg     240
caacaagtag gtagggagtt tttcctgttg cctgtggaag agaagatgaa gctttactca     300
gaggatccat cgaagacgat gaggctatcc accagcttta acgtccaaaa agaacaaatt     360
cataactggc gagattatct ccgccttcac tgttatcctc tggatcaata cagtcctgaa     420
tggccttcaa atccttctta tttcaaggaa tatgttggta attattgtac agcagtgcga     480
aatttaggaa tgagaatatt agaatcaata tcagaaagtt tagggttaca aaagaagaa      540 ataaaaacta tattaggcga tcaaggtcaa cacatggcca tcaaccatta cccagtgtgc     600
cctgagcccg agctaaccta cgggctaccc gggcacacag accccaatgc tctcaccatc     660
cttctacagg acacactggt ctctggtctt caggttctca agatggcaa atggttagcc      720 gttaaaccac accctaatgc gtttgtaatt aacattggtg atcagttaga ggcggtgagt     780
aatggtgaat ataaaagtgt atggcatcga gctgtggtta actcagacaa cccgcgaatg     840
tctatagctt cgttttttgtg tccttgtaat gacaccgtta ttagggctcc taaagaaata     900
```

```
ataaaggaag gatcgaaacc tgttttcaaa gaatttactt atgcagaata ctacgcgaag    960
ttttggacaa gaaaccttga tcaagaacat tgcttagaat tcttcaagaa ctag         1014
```

<210> SEQ ID NO 102
<211> LENGTH: 337
<212> TYPE: PRT
<213> ORGANISM: Lactuca sativa

<400> SEQUENCE: 102

```
Met Ala Ala Lys Val Ile Ser Ser Gly Phe Arg Tyr Thr Thr Leu Pro
1               5                   10                  15

Glu Ser Tyr Val Arg Pro Val Asn Asp Arg Pro Asn Leu Ser Gln Val
            20                  25                  30

Ser Asp Cys Asn Asp Val Pro Val Ile Asp Ile Gly Cys Gly Asp Arg
        35                  40                  45

Gln Leu Ile Ser Gln Gln Ile Gly Asp Ala Cys Arg Arg Tyr Gly Phe
    50                  55                  60

Phe Gln Val Ile Asn His Gly Val Pro Asp Glu Ile Val Glu Lys Met
65                  70                  75                  80

Gln Gln Val Gly Arg Glu Phe Phe Leu Leu Pro Val Glu Glu Lys Met
                85                  90                  95

Lys Leu Tyr Ser Glu Asp Pro Ser Lys Thr Met Arg Leu Ser Thr Ser
            100                 105                 110

Phe Asn Val Gln Lys Glu Gln Ile His Asn Trp Arg Asp Tyr Leu Arg
        115                 120                 125

Leu His Cys Tyr Pro Leu Asp Gln Tyr Ser Pro Glu Trp Pro Ser Asn
    130                 135                 140

Pro Ser Tyr Phe Lys Glu Tyr Val Gly Asn Tyr Cys Thr Ala Val Arg
145                 150                 155                 160

Asn Leu Gly Met Arg Ile Leu Glu Ser Ile Ser Glu Ser Leu Gly Leu
                165                 170                 175

Gln Lys Glu Glu Ile Lys Thr Ile Leu Gly Asp Gln Gly Gln His Met
            180                 185                 190

Ala Ile Asn His Tyr Pro Val Cys Pro Glu Pro Glu Leu Thr Tyr Gly
        195                 200                 205

Leu Pro Gly His Thr Asp Pro Asn Ala Leu Thr Ile Leu Leu Gln Asp
    210                 215                 220

Thr Leu Val Ser Gly Leu Gln Val Leu Lys Asp Gly Lys Trp Leu Ala
225                 230                 235                 240

Val Lys Pro His Pro Asn Ala Phe Val Ile Asn Ile Gly Asp Gln Leu
                245                 250                 255

Glu Ala Val Ser Asn Gly Glu Tyr Lys Ser Val Trp His Arg Ala Val
            260                 265                 270

Val Asn Ser Asp Asn Pro Arg Met Ser Ile Ala Ser Phe Leu Cys Pro
        275                 280                 285

Cys Asn Asp Thr Val Ile Arg Ala Pro Lys Ile Ile Lys Glu Gly
    290                 295                 300

Ser Lys Pro Val Phe Lys Glu Phe Thr Tyr Ala Glu Tyr Tyr Ala Lys
305                 310                 315                 320

Phe Trp Thr Arg Asn Leu Asp Gln Glu His Cys Leu Glu Phe Phe Lys
                325                 330                 335

Asn
```

<210> SEQ ID NO 103

<211> LENGTH: 1020
<212> TYPE: DNA
<213> ORGANISM: Spinacia oleracea

<400> SEQUENCE: 103

```
atggcaaaca agatattatc caccggaatt ccttacaaaa ccctccccga aagctacatc      60
cgacccgaaa atgagaggcc caacttatct caagtctccg attgcgagaa tgtccctgtt     120
attgacttgg gtgccaaaga ccgtactcaa acaatccacc aagtcttcaa tgcttgtaaa     180
aattacgggt ttttccaggt gattaatcat ggggtgtcaa aggaattagc ggagaagatg     240
caaaaggtag ctcgagagtt cttcgatatg tcggttgagg aaaaaatgaa attatatagt     300
gacgatccaa ctaaaacact aagattgtct acaagtttta acgttaacaa agaggaagtt     360
cataattgga gagattatct taggctccat tgttggcctc ttgagcaata tgtccccgaa     420
tggccttcta acccccttc cttcaaggaa atagtgagca agtacataaa agaagttagg     480
gaacttggtt tcagagtcca agaactaata tcagagagtt tagggttgga gaaagattac     540
ataaagaatg tcctaggaga tcaaggacaa acatggctc ttaattatta ccctgagtgc      600
ccggagccag agatgacata cgggttgccg ggtcatactg accctaatgc ccttaccatc     660
cttctccaag acttgcaagt atctggcctt caaattttta aggatggtaa atggcttgct     720
gtcaaacctc aacctgatgc ttttgtcatt aacattggtg atcaattgca ggcattaagt     780
aacggtatat acaagagtgt atggcacaga gcagttgtga acacagataa gccaagatta     840
tcagtagctt cattcctctg ccccgccaat gatgcgttga taagcgcgcc aacacctctg     900
accgccaacg gatcaccggc tgtatataga gactatacgt atcctgagta ctacaagact     960
ttctggagta ggaacttgga ccaagagcac tgcttggagc ttttaaaaa ccaaacctag    1020
```

<210> SEQ ID NO 104
<211> LENGTH: 339
<212> TYPE: PRT
<213> ORGANISM: Spinacia oleracea

<400> SEQUENCE: 104

Met Ala Asn Lys Ile Leu Ser Thr Gly Ile Pro Tyr Lys Thr Leu Pro
1               5                   10                  15

Glu Ser Tyr Ile Arg Pro Glu Asn Glu Arg Pro Asn Leu Ser Gln Val
                20                  25                  30

Ser Asp Cys Glu Asn Val Pro Val Ile Asp Leu Gly Ala Lys Asp Arg
            35                  40                  45

Thr Gln Thr Ile His Gln Val Phe Asn Ala Cys Lys Asn Tyr Gly Phe
        50                  55                  60

Phe Gln Val Ile Asn His Gly Val Ser Lys Glu Leu Ala Glu Lys Met
65                  70                  75                  80

Gln Lys Val Ala Arg Glu Phe Phe Asp Met Ser Val Glu Glu Lys Met
                85                  90                  95

Lys Leu Tyr Ser Asp Asp Pro Thr Lys Thr Leu Arg Leu Ser Thr Ser
                100                 105                 110

Phe Asn Val Asn Lys Glu Glu Val His Asn Trp Arg Asp Tyr Leu Arg
            115                 120                 125

Leu His Cys Trp Pro Leu Glu Gln Tyr Val Pro Glu Trp Pro Ser Asn
        130                 135                 140

Pro Pro Ser Phe Lys Glu Ile Val Ser Lys Tyr Ile Lys Glu Val Arg
145                 150                 155                 160

Glu Leu Gly Phe Arg Val Gln Glu Leu Ile Ser Glu Ser Leu Gly Leu

|  |  |  |  | 165 |  |  |  |  | 170 |  |  |  |  | 175 |  |
|---|---|---|---|---|---|---|---|---|---|---|---|---|---|---|---|
| Glu | Lys | Asp | Tyr | Ile | Lys | Asn | Val | Leu | Gly | Asp | Gln | Gly | Gln | His | Met |
|  |  |  |  | 180 |  |  |  |  | 185 |  |  |  |  | 190 |  |
| Ala | Leu | Asn | Tyr | Tyr | Pro | Glu | Cys | Pro | Glu | Pro | Glu | Met | Thr | Tyr | Gly |
|  |  |  | 195 |  |  |  |  | 200 |  |  |  |  | 205 |  |  |
| Leu | Pro | Gly | His | Thr | Asp | Pro | Asn | Ala | Leu | Thr | Ile | Leu | Leu | Gln | Asp |
|  | 210 |  |  |  |  | 215 |  |  |  |  | 220 |  |  |  |  |
| Leu | Gln | Val | Ser | Gly | Leu | Gln | Ile | Phe | Lys | Asp | Gly | Lys | Trp | Leu | Ala |
| 225 |  |  |  |  | 230 |  |  |  |  | 235 |  |  |  |  | 240 |
| Val | Lys | Pro | Gln | Pro | Asp | Ala | Phe | Val | Ile | Asn | Ile | Gly | Asp | Gln | Leu |
|  |  |  | 245 |  |  |  |  | 250 |  |  |  |  | 255 |  |  |
| Gln | Ala | Leu | Ser | Asn | Gly | Ile | Tyr | Lys | Ser | Val | Trp | His | Arg | Ala | Val |
|  |  |  | 260 |  |  |  |  | 265 |  |  |  |  | 270 |  |  |
| Val | Asn | Thr | Asp | Lys | Pro | Arg | Leu | Ser | Val | Ala | Ser | Phe | Leu | Cys | Pro |
|  |  | 275 |  |  |  |  | 280 |  |  |  |  | 285 |  |  |  |
| Ala | Asn | Asp | Ala | Leu | Ile | Ser | Ala | Pro | Thr | Pro | Leu | Thr | Ala | Asn | Gly |
|  | 290 |  |  |  |  | 295 |  |  |  |  | 300 |  |  |  |  |
| Ser | Pro | Ala | Val | Tyr | Arg | Asp | Tyr | Thr | Tyr | Pro | Glu | Tyr | Tyr | Lys | Thr |
| 305 |  |  |  |  | 310 |  |  |  |  | 315 |  |  |  |  | 320 |
| Phe | Trp | Ser | Arg | Asn | Leu | Asp | Gln | Glu | His | Cys | Leu | Glu | Leu | Phe | Lys |
|  |  |  | 325 |  |  |  |  | 330 |  |  |  |  | 335 |  |  |
| Asn | Gln | Thr |  |  |  |  |  |  |  |  |  |  |  |  |  |

<210> SEQ ID NO 105
<211> LENGTH: 1029
<212> TYPE: DNA
<213> ORGANISM: Cucumis sativus

<400> SEQUENCE: 105

| atgagcagtg tgatggagat ccaactttg tgttcagggg acgtcacga gaagttgcca | 60 |
|---|---|
| gagaagtatg aacggcctga atcggatagg ccgcggctgt cggaggtgtg ttgttgggac | 120 |
| aaggttccaa taatcgactt gggatgcgag gagagagaga tgattgtgaa gcaagtggag | 180 |
| gaggcctgca agtcttacgg cttttttccag gttataaatc atggtgtgag gaaggaattg | 240 |
| gtggagaaag tgatagaagt tggcaagcag ttctttgagc tgccgatgga ggagaagttg | 300 |
| aaatttttatt cagacgaccc ttccaagacc gtcagactct ccacaagttt caatgtccgg | 360 |
| aaagagcaat ttcgcaactg gagggattat ctcagactcc attgctatcc tctctccaac | 420 |
| tacacccccc attggccctc taacccacca tccttcaggg aaatagtgag tagttattgc | 480 |
| aatgaagtac gaaaagttgg gtacagaata gaggagctaa tatcggagag cttgggctg | 540 |
| gagaaggaat acataaggaa gaagttgggt gaacaaggtc agcacatggc tataaattat | 600 |
| tatccgccat gtccccaacc agaactcacc tacgggctcc ctggccatac ggatcccaac | 660 |
| gcactcacca ttctccttca ggatctccat gtcgccggcc tccaagtcct caagatggga | 720 |
| aagtggctag cggtcaaccc ccaccccaat gcctttgtaa tcaatatagg cgaccaattg | 780 |
| caggcattga gcaatggggt gtacaagagc gtttggcacc gagcggtggt caatgttgat | 840 |
| aagcccaggc tgtcggtcgc ttcttttctc tgcccttgtg atgacgccct cattactcct | 900 |
| gcaccgctcc tctcccagcc ttcccccatt tacagacctt tcacctacgc ccagtactac | 960 |
| aatacttttt ggagcagaaa cttggatcaa caacattgct tggaactatt taaaaaccac | 1020 |
| cctccttaa | 1029 |

<210> SEQ ID NO 106
<211> LENGTH: 342
<212> TYPE: PRT
<213> ORGANISM: Cucumis sativus

<400> SEQUENCE: 106

Met Ser Ser Val Met Glu Ile Gln Leu Leu Cys Ser Gly Gly Arg His
1               5                   10                  15

Glu Lys Leu Pro Glu Lys Tyr Glu Arg Pro Glu Ser Asp Arg Pro Arg
            20                  25                  30

Leu Ser Glu Val Cys Cys Trp Asp Lys Val Pro Ile Ile Asp Leu Gly
        35                  40                  45

Cys Glu Glu Arg Glu Met Ile Val Lys Gln Val Glu Glu Ala Cys Lys
    50                  55                  60

Ser Tyr Gly Phe Phe Gln Val Ile Asn His Gly Val Arg Lys Glu Leu
65                  70                  75                  80

Val Glu Lys Val Ile Glu Val Gly Lys Gln Phe Phe Glu Leu Pro Met
                85                  90                  95

Glu Glu Lys Leu Lys Phe Tyr Ser Asp Asp Pro Ser Lys Thr Val Arg
            100                 105                 110

Leu Ser Thr Ser Phe Asn Val Arg Lys Glu Gln Phe Arg Asn Trp Arg
        115                 120                 125

Asp Tyr Leu Arg Leu His Cys Tyr Pro Leu Ser Asn Tyr Thr Pro His
    130                 135                 140

Trp Pro Ser Asn Pro Ser Phe Arg Glu Ile Val Ser Ser Tyr Cys
145                 150                 155                 160

Asn Glu Val Arg Lys Val Gly Tyr Arg Ile Glu Glu Leu Ile Ser Glu
                165                 170                 175

Ser Leu Gly Leu Glu Lys Glu Tyr Ile Arg Lys Lys Leu Gly Glu Gln
            180                 185                 190

Gly Gln His Met Ala Ile Asn Tyr Tyr Pro Pro Cys Pro Gln Pro Glu
        195                 200                 205

Leu Thr Tyr Gly Leu Pro Gly His Thr Asp Pro Asn Ala Leu Thr Ile
    210                 215                 220

Leu Leu Gln Asp Leu His Val Ala Gly Leu Gln Val Leu Lys Asp Gly
225                 230                 235                 240

Lys Trp Leu Ala Val Asn Pro His Pro Asn Ala Phe Val Ile Asn Ile
                245                 250                 255

Gly Asp Gln Leu Gln Ala Leu Ser Asn Gly Val Tyr Lys Ser Val Trp
            260                 265                 270

His Arg Ala Val Val Asn Val Asp Lys Pro Arg Leu Ser Val Ala Ser
        275                 280                 285

Phe Leu Cys Pro Cys Asp Asp Ala Leu Ile Thr Pro Ala Pro Leu Leu
    290                 295                 300

Ser Gln Pro Ser Pro Ile Tyr Arg Pro Phe Thr Tyr Ala Gln Tyr Tyr
305                 310                 315                 320

Asn Thr Phe Trp Ser Arg Asn Leu Asp Gln Gln His Cys Leu Glu Leu
                325                 330                 335

Phe Lys Asn His Pro Pro
            340

<210> SEQ ID NO 107
<211> LENGTH: 3003
<212> TYPE: DNA
<213> ORGANISM: Arabidopsis thaliana

<400> SEQUENCE: 107

```
cattttctta taaatccaaa ctaacatcta ctttctttaa atctataacc ctaaacactt      60
ttttaaactc aaaccgatat ataatttgt ttaattttaa atctaaactc tagtgactta     120
tttataaacc caaacctaaa aataatttcg tttattgta aatttaaact ctaatttata     180
tttataaatc taaactgact tataattttg tttaattgta aaatctaaat tttaaatata     240
attaatcttg tttaattaaa agtatacaga tttgttattt tagtttatta tataatatga     300
tataataact agtttaaatt aaaagtaaga gtttattctt agaggtaaat gcaagtattg     360
tccgaaaaaa caaatctaat tcaagtagtg tccgaaaaaa aattctaact agtttgatag     420
ttaaaatttt gatttaaaaa aggaaaaaaa tcaaacaaga tattaattag aagtgtgaga     480
cacggcacaa gagtcacatg agtgtacgta cttatcaaga ttgactctgt ctgagtctga     540
agtcccaaac catgatggca ccacttccac atacgatcgt gccccgtatt ttggatagaa     600
tacggacagt ggttttcgtt tggacacgtg tcctgcttta tctcttcgtc gccccaaaaa     660
ataccacaat gtcttatctc aaccacacgt gttctgctta tcccaacctc acaatttgta     720
ccaaaataca cactttgcat ggaagatttt ctaattatac aactcacatt attcgaattt     780
aaatttcgat ttttagttt caagaaaatc attctttgat gggtacttgt cttatttaac     840
aggttgtata cttgtattca ttgttctgcc aaatgaaaat aaaaatgaaa atgatgttca     900
ttgtttaata aagtactaa gataacaatc acgacaaatt tctgtctagt tcattaaata     960
tttaatcaaa ctctaaacga ttttcaaaca atttttataa ttcaaaaaat aagttacata    1020
tctttgttta acataatata ataaaaataa catgaataaa ttatttaac ataaaaaatt    1080
cagttttca aaaataagtt tagaagttta cgttctaaaa taaggtaaaa tatgaatgct    1140
gttttaagac gcaatctaga taatttttt taataaaaac cgagatacat ttaaatctat    1200
ctaaataact tataactacc taattgttac ataatctacc aatttaactc tatgtaaaat    1260
aaaactgatt ttagtaacat ttaagcagta cgagaatgct agcgcctaat taaacgatct    1320
tctaatccac tttcttgaat atttgtttta actaaatcta aacaaaaata tagttatata    1380
accacaaata ttaatgaaat ttaaacttat agtaactgaa ataccaaaa ctaaaaaaaa    1440
aaaccaaaat tataataatt ataaataaga agatattagt ttatgtttac aatcgaaata    1500
atcaaataaa tgattgtctt tatttaggac tacgatcaag aaccgaatgg gcttttccaa    1560
accaaaccga gatttgaatt ttatggtgcg gattcggtta actggagaat agctatcaac    1620
aacaatttaa aatagattta gctagatcgg tttggttcgg ttcgttttgt attctctgtc    1680
actcctcaca atcgcttata ttttatattg tatgtttaaa agtcaacatc gaaatattgt    1740
acgttagtat gtcacttatg ataatgttta ttcgtaaaca caatttgaaa aggtcaaaga    1800
aagaggaaag atagttaatc aagccctttgt tgtcaaaaat aattatttta tttactgtca    1860
tcgtaatgtt tatcaatgca gttattaatc tcattttttt ctcttccgaa gtcgacgaac    1920
aataaaaaaa accaatctca ttcgaagtac ttattactga tatgatgctg agctgacaca    1980
gtcgtaagcc ttggacaaca atcattcatg acgtcactgc tgtgacgcta gaatgatgac    2040
attatatcaa tgttttttg tctgaatttt gttatggtaa aaataatgaa atgtagagc     2100
ttgagtattt tgattttcgt tttattgtaa actagctgaa tctgaatctt gagcagttaa    2160
ttaatttcgt aatttattaa ttctattctg acttttttaaa atataatata tattaacttt    2220
ggtagatgct taaggtaatt cttttttaat aaataagatg gttagagtat cttaaagtta    2280
gcttataaga aaatcggaaa aattactttt ggtgggttaa ttgtttctgt ttgaagtaat    2340
```

-continued

```
gtgtgtagat ttttcttatg aatttagatt aaaaactatt tgttttttcag atgttttaag    2400 aaaaaaattg tcattcatag cttgtccatt cttacatacc ttaataagaa aaattataaa    2460
gttttgtgga ttcacggaag ctaatctagg ttatgtattt gcccaaaaaa taatctaggt    2520
tttgttatgg aattaagaag gaaaaaaaaa ttgagataaa tagtatataa aaacaattta    2580
aactaagtat tattagctta attgataaag attttaggtg aaacttaaaa atagttggtt    2640
aaagagatta caaacattaa ccaaattaac caagaacctc ctagtattta aaaaaaacac    2700
ttaaaaatat ccaaacattt aattttttaa tcataaatct tataaaaccc acagctgtcc    2760
tttcgaaaat ccactatatt cggtggatta agaattaaaa atcattcgaa taatatgcat    2820
acttatataa caaaaacaat tcacttgaaa acataatcaa ttgagagtag gaccgagtaa    2880
cactgcattg ttttatatat atcatcgatg cacatcgcat acataatata ctcaaagtcg    2940
agccttcctt cctttatctc ttatacccct tttgattctt cttcaatttt ctgacatcaa    3000
atg                                                                  3003
```

```
<210> SEQ ID NO 108
<211> LENGTH: 24
<212> TYPE: DNA
<213> ORGANISM: Artificial Sequence
<220> FEATURE:
<223> OTHER INFORMATION: LP primer

<400> SEQUENCE: 108
caggtttatg gcatatctca cgtc                                           24

<210> SEQ ID NO 109
<211> LENGTH: 24
<212> TYPE: DNA
<213> ORGANISM: Artificial Sequence
<220> FEATURE:
<223> OTHER INFORMATION: T-DNA right border primer

<400> SEQUENCE: 109
tgataccaga cgttgcccgc ataa                                           24

<210> SEQ ID NO 110
<211> LENGTH: 25
<212> TYPE: DNA
<213> ORGANISM: Artificial Sequence
<220> FEATURE:
<223> OTHER INFORMATION: RB4 primer

<400> SEQUENCE: 110 tcacggggttg gggtttctac aggac                                         25

<210> SEQ ID NO 111
<211> LENGTH: 24
<212> TYPE: DNA
<213> ORGANISM: Artificial Sequence
<220> FEATURE:
<223> OTHER INFORMATION: LP or RP primer

<400> SEQUENCE: 111
atgtccaagt ccaatagcca caag                                           24
```

DISEASE RESISTANT TOMATO PLANTS

This application is a continuation application of U.S. patent application Ser. No. 14/528,707, filed Oct. 30, 2014 and issued as U.S. Pat. No. 9,546,373, which is a divisional application of U.S. patent application Ser. No. 14/250,875, filed Apr. 11, 2014 and issued as U.S. Pat. No. 9,121,029, which is a divisional application of U.S. patent application Ser. No. 12/525,236, filed Dec. 22, 2009 and issued as U.S. Pat. No. 8,742,207, which is the U.S. national phase of PCT Application No. PCT/EP2008/000718, filed Jan. 30, 2008, which claims priority to PCT Application No. PCT/EP2007/050976, filed Feb. 1, 2007, each of which is incorporated herein by reference in their entirety.

The Sequence Listing associated with this application is filed in electronic format via EFS-Web and is hereby incorporated by reference into the specification in its entirety. The name of the text file containing the Sequence Listing is 1601594_ST25.txt. The size of the text file is 108,973 bytes, and the text file was created on Jun. 21, 2016.

BACKGROUND OF THE INVENTION

Field of the Invention

The present invention relates to disease resistant plants, in particular plants resistant to organisms of the kingdom Fungi and the phylum Oomycota, the oomycetes. The invention further relates to plant genes conferring disease resistance and methods of obtaining such disease resistant plants for providing protection to Oomycota pathogens.

Description of Related Art

Resistance of plants to fungal and oomycete pathogens has been extensively studied, for both pathogen specific and broad resistance. In many cases resistance is specified by dominant genes for resistance. Many of these race-specific or gene-for-gene resistance genes have been identified that mediate pathogen recognition by directly or indirectly interacting with avirulence gene products or other molecules from the pathogen. This recognition leads to the activation of a wide range of plant defense responses that arrest pathogen growth.

In plant breeding there is a constant struggle to identify new sources of mostly monogenic dominant resistance genes. In cultivars with newly introduced single resistance genes, protection from disease is often rapidly broken, because pathogens evolve and adapt at a high frequency and regain the ability to successfully infect the host plant. Therefore, the availability of new sources of disease resistance is highly needed.

Alternative resistance mechanisms act for example through the modulation of the defense response in plants, such as the resistance mediated by the recessive mlo gene in barley to the powdery mildew pathogen *Blumeria graminis* f. sp. *hordei*. Plants carrying mutated alleles of the wildtype MLO gene exhibit almost complete resistance coinciding with the abortion of attempted fungal penetration of the cell wall of single attacked epidermal cells. The wild type MLO gene thus acts as a negative regulator of the pathogen response. This is described in WO9804586.

Other examples are the recessive powdery mildew resistance genes, found in a screen for loss of susceptibility to *Erysiphe cichoracearum*. Three genes have been cloned so far, named PMR6, which encodes a pectatelyase-like protein, PMR4 which encodes a callose synthase, and PMR5 which encodes a protein of unknown function. Both mlo and pmr genes appear to specifically confer resistance to powdery mildew and not to oomycetes such as downy mildews.

Broad pathogen resistance, or systemic forms of resistance such as SAR, has been obtained by two main ways. The first is by mutation of negative regulators of plant defense and cell death, such as in the cpr, lsd and acd mutants of *Arabidopsis*. The second is by transgenic over-expression of inducers or regulators of plant defense, such as in NPR1 overexpressing plants.

The disadvantage of these known resistance mechanisms is that, besides pathogen resistance, these plants often show detectable additional and undesirable phenotypes, such as stunted growth or the spontaneous formation of cell death.

SUMMARY OF THE INVENTION

It is an object of the present invention to provide a form of resistance that is broad, durable and not associated with undesirable phenotypes.

In the research that led to the present invention, an *Arabidopsis thaliana* mutant screen was performed for reduced susceptibility to the downy mildew pathogen *Hyaloperonospora parasitica*. EMS-mutants were generated in the highly susceptible *Arabidopsis* line Ler eds1-2. Eight downy mildew resistant (dmr) mutants were analyzed in detail, corresponding to 6 different loci. Microscopic analysis showed that in all mutants *H. parasitica* growth was severely reduced. Resistance of dmr3, dmr4 and dmr5 was associated with constitutive activation of plant defense. Furthermore, the dmr3 and dmr4, but not dmr5 mutants, were also resistant to *Pseudomonas syringae* and *Golovinomyces orontii*.

In contrast, enhanced activation of plant defense was not observed in the dmr1, dmr2, and dmr6 mutants. The results of this research have been described in Van Damme et al. (2005) Molecular Plant-Microbe Interactions 18(6) 583-592. This article does not disclose the identification and characterization of the DMR genes.

The dmr6 mutant was identified in a loss-of-susceptibility screen in the *Arabidopsis* Ler eds1-2 background. The DMR6 gene now has been cloned and characterized. Thus, it was found that DMR6 is the gene At5g24530, encoding for an oxidoreductase (DNA and amino acid sequence are depicted in FIG. 2). Oxidoreductases are enzymes that catalyze the transfer of electrons from one molecule, the oxidant, to another, the reductant. According to the present invention, it has been found that lack of a functional DMR6 protein results in downy mildew resistance.

The present invention thus provides a plant, which is resistant to a pathogen of viral, bacterial, fungal or oomycete origin, characterized in that the plant has a reduced level, reduced activity or complete absence of the DMR6 protein as compared to a plant that is not resistant to the said pathogen.

This form of resistance is in particular effective against pathogens of the phylum Oomycota, such as *Albugo, Aphanomyces, Basidiophora, Bremia, Hyaloperonospora, Pachymetra, Paraperonospora, Perofascia, Peronophythora, Peronospora, Peronosclerospora, Phytium, Phytophthora, Plasmopara, Protobremia, Pseudoperonospora, Sclerospora, Viennotia* species, as well as to pathogens belonging to the Fungi.

The resistance according to the invention is based on an altered, in particular a reduced level, reduced activity or complete absence of the DMR6 protein in planta. The term "DMR6 protein" in this respect relates to the DMR6 gene product, such as the protein encoded by the At5g24530 gene in *Arabidopsis*. Such alterations can be achieved in various ways.

In one embodiment of the invention, the reduced level of DMR6 protein is the result of a reduced endogenous DMR6 gene expression. Reducing the expression of the DMR6 gene can be achieved, either directly, such as by gene silencing, or indirectly by modifying the regulatory sequences thereof, or by stimulating repression of the gene.

Modulating the DMR6 gene to lower its activity or expression can be achieved at various levels. First, the endogenous gene can be directly mutated. This can be achieved by means of a mutagenic treatment. Alternatively, a modified DMR6 gene can be brought into the plant by means of transgenic techniques or by introgression, or the expression of DMR6 can be reduced at the regulatory level, for example by modifying the regulatory sequences or by gene silencing.

In another embodiment of the invention, the reduced level of DMR6 protein is the result of a mutation in the DMR6 gene resulting in a reduced DMR6 expression as compared to the wild-type DMR6 gene wherein no such mutation is present, or resulting in a reduced mRNA or protein stability. In a particular embodiment this is achieved by mutations in the DMR6 coding sequence that result in a non-functional DMR6 protein, i.e., without or with reduced enzymatic activity.

In another embodiment of the invention, reduced expression can be achieved by down-regulation of DMR6 gene expression either at the transcriptional or the translational level, e.g., by gene silencing or by mutations that affect the expression of the DMR6 gene.

This invention is based on research performed on resistance to *Hyaloperonospora parasitica* in *Arabidopsis* but is a general concept that can be more generally applied in plants, in particular in crop plants that are susceptible to infections with pathogens, such as Oomycota and Fungi.

The invention is suitable for a large number of plant diseases caused by oomycetes such as, but not limited to, *Bremia lactucae* on lettuce, *Peronospora farinosa* on spinach, *Pseudoperonospora cubensis* on members of the Cucurbitaceae family, e.g., cucumber and melon, *Peronospora destructor* on onion, *Hyaloperonospora parasitica* on members of the Brasicaceae family, e.g., cabbage, *Plasmopara viticola* on grape, *Phytophthora infestans* on tomato, and *Phytophthora sojae* on soybean.

When the modification of DMR6 gene expression in a plant is to be achieved via genetic modification of the DMR6 gene or via the identification of mutations in the DMR6 gene, and the gene is not yet known it must first be identified. To generate pathogen-resistant plants, in particular crop plants, via genetic modification of the DMR6 gene or via the identification of mutations in the DMR6 gene, the orthologous DMR6 genes must be isolated from these plant species.

Various methods are available for the identification of orthologous sequences in other plants.

A method for the identification of DMR6 orthologous sequences in a plant species, may for example comprise identification of DMR6 ESTs of the plant species in a database; designing primers for amplification of the complete DMR6 transcript or cDNA; performing amplification experiments with the primers to obtain the corresponding complete transcript or cDNA; and determining the nucleotide sequence of the transcript or cDNA. Suitable methods for amplifying the complete transcript or cDNA in situations where only part of the coding sequence is known are the advanced PCR techniques 5'RACE, 3'RACE, TAIL-PCR, RLM-RACE and vectorette PCR.

Alternatively, if no nucleotide sequences are available for the plant species of interest, primers are designed on the DMR6 gene of a plant species closely related to the plant of interest, based on conserved domains as determined by multiple nucleotide sequence alignment, and used to PCR amplify the orthologous sequence. Such primers are suitably degenerate primers.

Another reliable method to assess a given sequence as being a DMR6 ortholog is by identification of the reciprocal best hit. A candidate orthologous DMR6 sequence of a given plant species is identified as the best hit from DNA databases when searching with the *Arabidopsis* DMR6 protein or DNA sequence, or that of another plant species, using a Blast program. The obtained candidate orthologous nucleotide sequence of the given plant species is used to search for homology to all *Arabidopsis* proteins present in the DNA databases (e.g., at NCBI or TAIR) using the BlastX search method. If the best hit and score is to the *Arabidopsis* DMR6 protein, the given DNA sequence can be described as being an ortholog, or orthologous sequence.

DMR6 is encoded by a single gene in *Arabidopsis* as deduced from the complete genome sequence that is publicly available. In the genome of rice 3 orthologs, and in poplar 2 orthologs have been identified. In most other plant species tested so far, DMR6 appears to be encoded by a single gene, as determined by the analysis of mRNA sequences and EST data from public DNA databases. The orthologous genes and proteins are identified in these plants by nucleotide and amino acid comparisons with the information that is present in public databases.

Alternatively, if no DNA sequences are available for the desired plant species, orthologous sequences are isolated by heterologous hybridization using DNA probes of the DMR6 gene of *Arabidopsis* or another plant or by PCR methods, making use of conserved domains in the DMR6 coding sequence to define the primers. For many crop species, partial DMR6 mRNA sequences are available that can be used to design primers to subsequently PCR amplify the complete mRNA or genomic sequences for DNA sequence analysis.

In a specific embodiment the ortholog is a gene of which the encoded protein shows at least 50% identity with the *Arabidopsis* DMR6 protein (At5g24530) or that of other plant DMR6 proteins. In a more specific embodiment the identity is at least 55%, more specifically 60%, even more specifically 65%, 70%, 75%, 80%, 85%, 90%, 95% or 99%.

BRIEF DESCRIPTION OF THE DRAWINGS

FIG. 1A-D shows the alignment of the amino acid sequences of the DMR6 protein of *Arabidopsis thaliana* (SEQ ID NO. 62) and orthologs from *Aquilegia* species (SEQ ID NO. 63), *Citrus sinensis* (SEQ ID NO. 64), *Coffea canephora* (SEQ ID NO. 65), *Cucumis sativus* (SEQ ID NO. 67), *Gossypium hirsitum* (SEQ ID NO. 68), *Lactuca sativa* (SEQ ID NO. 70), *Medicago truncatula* (SEQ ID NO. 71), *Oryza sativa* (SEQ ID NOs. 72-74), *Populus trichocarpa* (SEQ ID NOs. 75 and 76), *Solanum lycopersicum* (SEQ ID NOs. 77 and 78), *Sorghum bicolor* (SEQ ID NO. 79), *Spinacia oleracea* (SEQ ID NO. 81), *Vitis vinifera* (SEQ ID NO. 82), *Zea mays* (SEQ ID NO. 83), and *Zingiber officinale* (SEQ ID NO. 84), using the CLUSTAL W (1.83) multiple sequence alignment program (EBI). Below the sequences the conserved amino acids are indicated by the dots, and the identical amino acids are indicated by the asterisk.

FIG. 2 shows the nucleotide (SEQ ID NO. 61) and amino acid sequence (SEQ ID NO. 62) of the DMR6 gene (At5g24530, gi 42568064, Genbank NM_122361) and protein (gi 15238567, Genbank NP_197841) of *Arabidopsis thaliana*, respectively.

FIG. 3 shows the nucleotide (SEQ ID NO. 69) and derived amino acid sequence (SEQ ID NO. 70) of the DMR6 ortholog of *Lactuca sativa*, respectively.

FIG. 4 shows the nucleotide (SEQ ID NO. 80) and derived amino acid sequence (SEQ ID NO. 81) of the DMR6 ortholog of *Spinacia oleracea*, respectively.

FIG. 5 shows the nucleotide (SEQ ID NO. 66) and derived amino acid sequence (SEQ ID NO. 67) of the DMR6 ortholog of *Cucumis sativus* and *Cucumis melo*.

FIG. 11 shows the nucleotide sequence (SEQ ID NO. 107) of the 3 kb region upstream of the start codon of the DMR6 gene (at5g24530) of *Arabidopsis thaliana*, including the promoter and 5'-UTR (underlined).

FIG. 12 shows the nucleotide (SEQ ID NO. 95) and derived amino acid sequence (SEQ ID NO. 96) of the DMR6 ortholog of *Solanum lycopersicum*, respectively.

FIG. 13 shows the nucleotide (SEQ ID NO. 97) and derived amino acid sequence (SEQ ID NO. 98) of the DMR6 ortholog of *Nicotiana benthamiana*, respectively.

DETAILED DESCRIPTION OF THE INVENTION

Figure 6A:
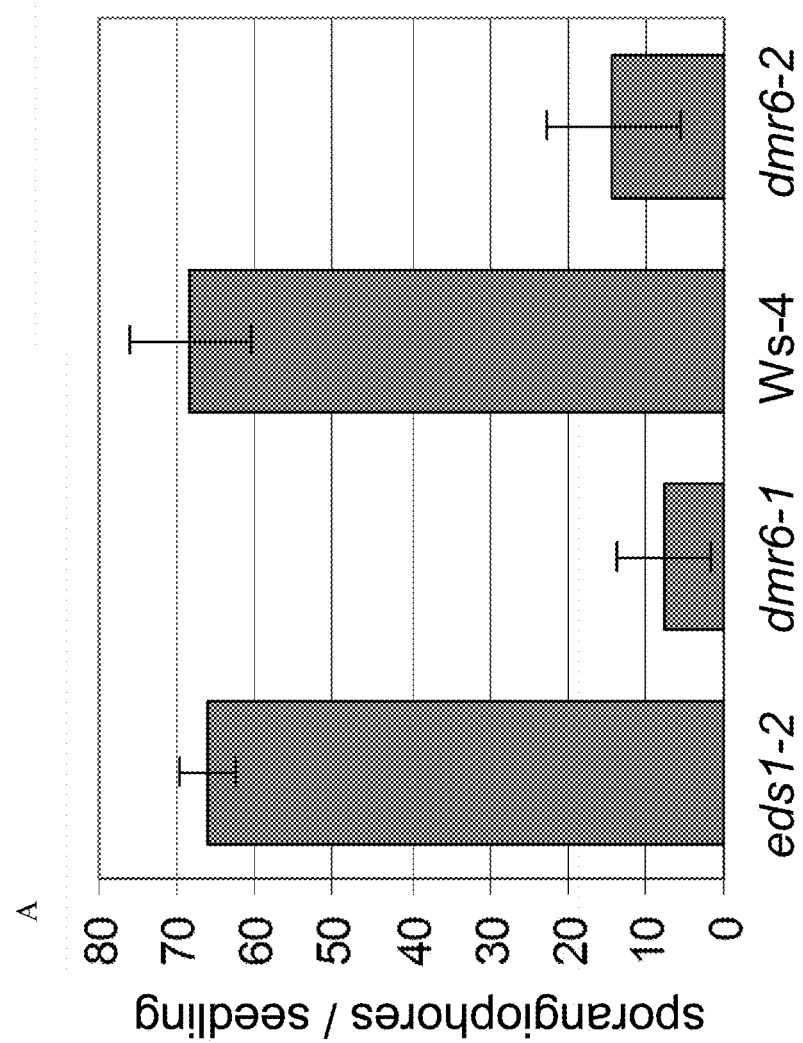
FIG. 6A-B shows the downy mildew resistance of the *Arabidopsis* dmr6 mutants. (a) Quantification of sporangiophores of *H. parasitica* isolate Waco9, 7 days post inoculation, on the dmr6-1 mutant ($BC_2$, line E37) compared to its parental line Ler eds1-2 and on the dmr6-2 mutant (FLAG_445D09 T-DNA line) compared to its parental line Ws-4. (b) Restoration of susceptibility by complementation with the At5g24530 gene in the dmr6-1 mutant. *H. parasitica* spores per mg seedling weight were quantified on Ler eds1-2, dmr6-1 and 5 complementation lines (#121, 122, 211, 231, and 241).

FIG. 1 shows orthologous DMR6 sequences (described in Table 1) that have been identified in publicly available databases and obtained by PCR amplification on cDNA and subsequent sequencing. After orthologous DMR6 sequences are identified, the complete nucleotide sequence of the regulatory and coding sequence of the gene is identified by standard molecular biological techniques. For this, genomic libraries of the plant species are screened by DNA hybridization or PCR with probes or primers derived from a known DMR6 gene to identify the genomic clones containing the DMR6 gene. Alternatively, advanced PCR methods, such as RNA ligase-mediated RACE (RLM-RACE), can be used to directly amplify gene and cDNA sequences from genomic DNA or reverse-transcribed mRNA. DNA sequencing subsequently results in the characterization of the complete gene or coding sequence.

Once the DNA sequence of the gene is known this information is used to prepare the means to modulate the expression of the DMR6 gene.

To achieve a reduced DMR6 protein level, the expression of the DMR6 gene can be down-regulated or the enzymatic activity of the DMR6 protein can be reduced by amino acid substitutions resulting from nucleotide changes in the DMR6 coding sequence.

In a particular embodiment of the invention, downregulation of DMR6 gene expression is achieved by gene-silencing using RNAi. For this, transgenic plants are generated expressing a DMR6 anti-sense construct, an optimized micro-RNA construct, an inverted repeat construct, or a combined sense-anti-sense construct, so as to generate dsRNA corresponding to DMR6 that leads to gene silencing.

In an alternative embodiment, one or more regulators of the DMR6 gene are downregulated (in case of transcriptional activators) by RNAi.

In another embodiment regulators are upregulated (in case of repressor proteins) by transgenic overexpression. Overexpression is achieved in a particular embodiment by expressing repressor proteins of the DMR6 gene from a strong promoter, e.g., the 35S promoter that is commonly used in plant biotechnology.

The downregulation of the DMR6 gene can also be achieved by mutagenesis of the regulatory elements in the promoter, terminator region, or potential introns. Mutations in the DMR6 coding sequence in many cases leads to amino acid substitutions or premature stop codons that negatively affect the expression or activity of the encoded DMR6 protein.

These mutations are induced in plants by using mutagenic chemicals such as ethyl methane sulfonate (EMS), by irradiation of plant material with gamma rays or fast neutrons, or by other means. The resulting nucleotide changes are random, but in a large collection of mutagenized plants the mutations in the DMR6 gene can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-

636). The principle of this method is based on the PCR amplification of the gene of interest from genomic DNA of a large collection of mutagenized plants in the M2 generation. By DNA sequencing or by looking for point mutations using a single-strand specific nuclease, such as the CEL-I nuclease (Till et al. (2004) Mismatch cleavage by single-strand specific nucleases. Nucleic Acids Res. 32, 2632-2641) the individual plants that have a mutation in the gene of interest are identified.

By screening many plants, a large collection of mutant alleles is obtained, each giving a different effect on gene expression or enzyme activity. The gene expression or protein levels can for example be tested by analysis of DMR6 transcript levels (e.g., by RT-PCR) or by quantification of DMR6 protein levels with antibodies.

Plants with the desired reduced DMR6 level or DMR6 expression are then back-crossed or crossed to other breeding lines to transfer only the desired new allele into the background of the crop wanted.

The invention further relates to mutated DMR6 genes. In a particular embodiment, the invention relates to dmr6 alleles with premature stop codons, such as the dmr6-1 allele.

In another embodiment, the invention relates to mutated versions of the DMR6 genes of *Lactuca sativa, Cucumis sativus*, and *Spinacia oleracea* as shown in FIGS. 3-5.

The present invention demonstrates that plants having no or a reduced level of functional DMR6 gene product show resistance to pathogens, in particular of oomycete and fungal origin. With such knowledge the skilled person can identify so far unknown natural variants of a given plant species that have variants of the DMR6 gene that lead to a reduced level or absence of a functional DMR6 protein, or mutated versions of the DMR6 protein, and to use these natural variants according to the invention.

The present invention further relates to the use of a DMR6 promotor for providing disease resistance into plants, i.e., for providing plants with a resistance to a pathogen of viral, bacterial, fungal or oomycete origin. According to the present invention, the transcriptional up-regulation of DMR6 in response to pathogen infection has been demonstrated. Both transcript analysis as well as promotor DMR6-reporter lines support this finding (see Example 1, below). The pathogen-inducible DMR6 promotor according to the invention thus is particularly useful to control the expression of inducible systems that lead to disease resistance in plants.

One example of such inducible system that leads to disease resistance in plants, and in which the DMR6 promotor according to the present invention may be effective, has e.g., been described in WO 99/45125, wherein an antisense nucleotide sequence for a gene involved in the regulation of the C-5 porphyrin metabolic pathway is operably linked to a pathogen-inducible promotor and used to transform plant cells. Expression of the antisense nucleotide sequence in response to the pathogen effectively disrupts porphyrin metabolism of the transformed plant cell, and development of a localized lesion wherein the spread of the pathogen is contained. WO 96/36697 also discloses inducible systems leading to disease resistance in plants, wherein an inducible promotor controls the expression of a protein capable of evoking the hypersensitivity response in a plant. EP 0474857 furthermore discloses a method for the induction of pathogen resistance in plants, comprising transforming plants with polynucleotide sequences encoding a pair of pathogen-derived-avirulence-gene/plant-derived-resistance gene, wherein the expression of one of or both the elicitor peptide and the resistance gene is regulated by a pathogen inducible promotor. Further examples of inducible systems leading to resistance to pathogens in plants have been described in e.g., WO 98/32325.

In a particular preferred embodiment, the present invention relates to a method of providing disease resistance in a plant, comprising transforming a plant cell with a DNA construct comprising at least one expressible nucleic acid which is operably linked to a pathogen-inducible promotor that is operable within a plant cell, and regenerating transformed plants from said plant cells, wherein the pathogen-inducible promotor is a DMR6 promotor, and wherein the expression of the expressible nucleic acid confers disease resistance to the transgenic plant.

The invention also relates to disease resistance plants, obtainable by said method, as well as to plant tissue, and seeds obtained from said plants.

The invention in particular relates to plants, which are resistant to a pathogen of viral, bacterial, fungal or oomycete origin, wherein the plant comprises in its genome a DNA construct, comprising at least one expressible nucleic acid which is operably linked to a pathogen-inducible promotor, wherein the pathogen-inducible promotor is a DMR6 promotor.

The present invention also relates to the DNA construct per se, comprising at least one expressible nucleic acid which is operably linked to a pathogen-inducible promotor, wherein the pathogen-inducible promotor is a DMR6 promotor. The construct of the invention can be used to transform plant cells which may be regenerated into transformed plants. Furthermore, transformed plant tissue and seed may be obtained. Suitable methods for introducing the construct of the invention into plant cells are known to the skilled person.

According to the invention, by "operably linked" is meant that a promotor and an expressible nucleic acid, e.g., a gene, are connected in such way as to permit initiation of transcription of the expressible nucleic acid (e.g., gene) by the promotor.

By "expressible nucleic acid" is meant a nucleic acid (e.g., a gene, or part of a gene) that can be expressed in the cell i.e., that can be transcribed into mRNA, and eventually may be translated into a protein. The expressible nucleic acid may be genomic DNA, cDNA, or chemically synthesized DNA or any combination thereof.

According to the present invention, a DNA construct comprises all necessary nucleic acid elements which permit expression (i.e., transcription) of a particular nucleic acid in a cell. Typically, the construct includes an expressible nucleic acid, i.e., a nucleic acid to be transcribed, and a promotor. The construct can suitably be incorporated into e.g., a plasmid or vector.

The expressible nucleic acid preferably is a gene involved in a plant defense response, e.g., a gene associated with the hypersensitivity response of a plant. In the hypersensitivity response (HR) of a plant, the site in the plant where the pathogen invades undergoes localized cell death by the induced expression of a suicide mechanism that triggers said localized cell death in response to pathogens. In this way, only a few plant cells are sacrificed and the spread of the pathogen is effectively arrested. Examples of said genes involved in a plant defense response are the regulatory protein NPR1/NIM1 (Friedrich et al., Mol. Plant Microbe Interact. 14(9): 1114-1124, 2001) and the transcription factor MYB30 (Vailleau et al., Proc. Natl. Acad. Sci. USA 99(15): 10179-10184, 2002).

In a particular embodiment, the expressible nucleic acid encodes an autologous or heterologous polypeptide capable of conferring disease-resistance to a plant. By "autologous polypeptide" is meant any polypeptide that is expressed in a transformed plant cell from a gene that naturally occurs in the transformed plant cell. By "heterologous polypeptide" is meant any polypeptide that is expressed in a transformed plant cell from a gene that is partly or entirely foreign (i.e., does not naturally occur in) to the transformed plant cell. Examples of such polypeptides are the mammalian Bax protein, which encodes a pro-apoptotic protein and results in cell death in plants (Lacomme and Santa Cruz, Proc. Natl. Acad. Sci. USA 96(14): 7956-61, 1999) and fungal chitinases (de las Mercedes Dana et al., Plant Physiol. 142(2): 722-730, 2006).

Preferably, the DMR6 promotor is the *Arabidopsis* DMR6 promotor. The DMR6 promotor comprises a region of 3000 bp that is upstream of the *Arabidopsis* DMR6 coding sequence (ATG start codon) and includes the 5'UTR. Preferably the DMR6 promotor comprises a nucleotide sequence as defined in FIG. 11, and/or any functional fragment thereof, i.e., any fragment (or part) of said sequence which still is capable of initiating transcription of the expressible nucleic acid(s) to which it is operably linked, and/or natural variants thereof, i.e., natural variants of this promotor which may contain small polymorphisms, but which are generally at least 90% identical.

In a further preferred embodiment, the DMR6 promotor is an orthologous DMR6 promotor, i.e., a promotor of an orthologous DMR6 gene. Methods for identifying DMR6 orthologs have been described in Example 2 below. Once the DMR6 orthologs have been identified, the skilled person will be able to isolate the respective promotor of said orthologs, using standard molecular biological techniques.

According to the present invention, the DMR6 promotor has been shown to be strongly pathogen-induced, and the DMR6 promotor is not highly expressed in other non-infected tissues. Thus, it is a very suitable promotor for use in inducible systems for providing resistance to pathogens of viral, bacterial, fungal or oomycete origin in plants. Examples of specific pathogens and plants for which the inducible system, using the DMR6 promotor of the present invention, suitably can be used, have been given above.

The present invention is illustrated in the following examples that are not intended to limit the invention in any way. In the examples reference is made to the figures described above and the following tables.

Table 1 shows the Genbank accession numbers and GenInfo identifiers of the *Arabidopsis* DMR6 mRNA and orthologous sequences from other plant species.

Table 2 shows the PCR primers for the markers used for the map-based cloning of DMR6.

Table 3 shows primer pairs for cloning dmr6 orthologs in a suitable plant expression vector.

Example 1

The *Arabidopsis* DMR6 (At5g24530) Gene is Required for Downy Mildew Susceptibility
Experimental Procedures
*Hyaloperonospora parasitica* Growth and Infection

*H. parasitica* isolate Waco9 was provided by Dr. M. Aarts (WUR, Wageningen, NL) and isolate Cala2 provided by Dr. E. Holub (Warwick HRI, Wellsbourne, UK) and maintained on *Arabidopsis* Ws-0 and Ler, respectively. Inocula (400,000 spores per ml) were weekly transferred to 10 day old healthy seedlings (Holub, E. B. et al., Mol. Plant Microbe Interact. 7: 223-239, 1994) by use of a spray gun. Seedlings were air-dried for approximately 45 minutes and incubated under a sealed lid at 100% relative humidity in a growth chamber at 16° C. with 9 hours of light per day (100 mE/m2/s). The sporulation levels were quantified 7 days post inoculation (dpi) by counting the number of sporangiophores per seedling, for at least 40 seedlings per tested line (FIG. 6a) or by isolating spores in water 5 dpi and determining the spore concentration to give the number per mg leaf tissue (FIG. 6b).

Generation of Backcrossed dmr6 Lines

The dmr6 mutants were back crossed twice ($BC_2$) to the parental line Ler eds1-2 as well as Ler. The $BC_2$ lines generated with Ler were selected for the presence of the wild type EDS1 gene by PCR analysis.

Cloning DMR6

Fine mapping of the dmr6 gene was done with PCR markers designed using the Cereon database to identify insertion and deletion (IND) differences between Col-0 and Ler. The markers: IND_MOP9 in gene At5G24210; IND_K16H17 in gene At5G24420; IND_T4C12 in gene At5G24820; IND_T11H3 in between genes At5G24950_60 and IND_F21J6 in gene At5G25270 were used for mapping (Table 2). An additional screen for new recombinants was initiated on 300 F2 plants resulting in eight F2 recombinant plants between the two IND based markers IND_MOP9 and IND_T4C12, which flanked a region of 61 genes. Seven additional markers (M450-M590; Table 2) reduced the region to eighteen candidate genes for the dmr6 locus, between At5g24420 and At5g24590. Sequence analysis of At5g24530 indicated a point mutation leading to a stop codon in exon 2 in the dmr6-1 mutant.

Identification of a dmr6 T-DNA Insertion Line

A second dmr6 allele was identified, 445D09 a FLAG T-DNA insertion line generated by INRA Versailles in the Ws-4 accession background. The T-DNA insertion was confirmed by PCR using a primer designed in the At5g24530 gene, LP primer (5'-caggittatggcatatctcacgtc-3') (SEQ ID NO: 108), in combination with the T-DNA right border primer, Tag3' (5'-tgataccagacgttgcccgcataa-3') (SEQ ID NO: 109) or RB4 (5'-tcacgggttggggtttctacaggac-3') (SEQ ID NO: 110). The exact T-DNA insertion in the second intron of At5g24530 was confirmed by sequencing of amplicons generated with the T-DNA primers from both the left and right border in combination with the gene specific primers LP or RP (5'-atgtccaagtccaatagccacaag-3') (SEQ ID NO: 111).

cDNA Synthesis

RNA was isolated (from approximately 100 mg leaf tissue from 10 day old seedlings) with the RNaesy kit (Qiagen, Venlo, The Netherlands) and treated with the RNase-free DNase set (Qiagen). Total RNA was quantified using an UVmini-1240 spectrophotometer (Shimadzu, Kyoto, Japan). cDNA was synthesized with Superscript III reverse transcriptase (Invitrogen, Carlsbad, Calif., USA) and oligo (dT)15 (Promega, Madison, Wis., USA), according manufactures instructions.

Complementation of the dmr6-1 Mutant

Complementation lines were generated by transforming dmr6 plants by the floral dip method with *Agrobacterium tumefaciens* (Clough and Bent, 1998) containing the At5g24530 gene from Col-0 behind the 35S promoter. The construct was generated by PCR amplification of the full length At5g24530 from Col-0 cDNA with primers which included restriction sites that were used for directional cloning. A forward primer (5'-ttct gggatccaATGGCGGCAAAGCTGATATC-3') (SEQ ID NO: 1) containing a BamHI restriction site near the start codon (ATG), amplified the 5'-end of DMR6 and at the 3'-end after the stop codon an EcoRI site was generated with a reverse primer (5'-gatatatgaattcttagttgtttagaaaattctcgaggc-3') (SEQ ID NO: 2). The 35S-DMR6-Tn was cloned into the pGreenIIO229 (Hellens, R. P., Edwards, E. A., Leyland, N. R., Bean, S., and Mullineaux, P. M. (2000)). pGreen: a versatile and flexible binary Ti vector for *Agrobacterium*-mediated plant transformation. Plant Mol. Biol. 42, 819-832). 300 μM DL-Phosphinothricin (BASTA) resistant seedlings were isolated and analyzed for *H. parasitica* susceptibility and for DMR6 expression levels by RT-PCR.

Knock Down Lines of DMR6 by RNAi

RNAi lines were generated in the Ler eds1-2 and Col-0 background. A 782 bp long cDNA amplicon of Col-0 At5g24530 gene was generated. The PCR was done with the Phusion DNA polymerase (2 U/μL) and two different primer combinations. The amplicon from the first DMR6 gene specific primer combination

```
(RNAiDMR6F:
                                          (SEQ ID NO: 3)
5'-aaaaagcaggctGACCGTCCACGTCTCTCTGAA-3'
and RNAiDMR6R:
                                          (SEQ ID NO: 4)
5'-AGAAAGCTGGGTGAAACGATGCGACCGATAGTC-3')
``` was used as a template for the second PCR amplification with general primers allowing recombination into the pDONR7 vector of the GateWay cloning system. For the second PCR 10 μl of the first PCR (denaturation for 30 sec. at 98° C. followed by 10 cycles of: 10 sec. at 98° C.; 30 sec. at 58° C.; 30 sec. at 72° C.) in a total volume of 20 μl was used as template. The second PCR (denaturation for 30 sec. at 98° C. followed by 5 cycles of: 10 sec. at 98° C.; 30 sec. at 45° C.; 30 sec. at 72° C. and 20 cycles of 10 sec. at 98° C.; 30 sec. at 55° C.; 30 sec. at 72° C. finished by a final extension of 10 min at 72° C.) with the attB1 (5'-GGGA-CAAGTTTGTACAAAAAAGCAGGCT-3') (SEQ ID NO: 5) and the attB2

```
                                          (SEQ ID NO: 6)
(5'-ggggaccactttgtacaagaaagctgggt-3')
``` were performed in a 50 μl reaction volume. PCR product was gel purified and 50 ŋg insert was recombined into 150 ŋg pDONR7 vector with the clonase BP enzyme. The vector was transformed into electrocompotent DH5α *E. coli* cells and plasmids containing the correct insert were isolated and 100 ŋg of the pDONR7 with the DMR6 amplicon were used in the LR reaction to recombine the insert in two opposite direction into 150 ŋg pHellsgate8 vector. After transformation into *E. coli*, Spectomycin resistant clones were selected and the isolated plasmids were verified by a NotI digest for the right insert size and by colony PCR with a single internal primer for At5G24530 (DfragmentF: 5'-gagaagtgggatttaaaatagaggaa-3') (SEQ ID NO: 7), if the inserts was inserted twice in opposite direction an amplicon of 1420 bp could be detected. Correct pHellsgate8 plasmids with the double insert in opposite directions were transformed into electrocompotent *Agrobacterium* strain, C58C1. Plasmids were isolated from the *Agrobacterium* and retransformed into the *E. coli* to confirm the right size of the plasmid and the insert by NotI digestion. The reconfirmed *Agrobacterium* strains were used for the floral dip transformation of the Col-0 and Ler eds1-2 plants. The developed seeds were screened for Kanamycin resistance on ½× GM plates, the T₁ seedlings were transferred and the next generation of seeds the T₂ was analyzed for DMR6 expression and *H. parasitica* susceptibility.

Gene Expression Profiling of the dmr6 Mutant

Total RNA was isolated as described above. mRNA was amplified with the MessageAmp aRNA kit (Ambion). CATMA array (Crowe et al., 2003) slides containing approximately 25,000 gene specific tags were hybridized according to standardized conditions described by de Jong et al. (de Jong M., van Breukelen B., Wittink, F. R., Menke, F. L., Weisbeek, P. J., and Van den Ackerveken G. (2006). Membrane-associated transcripts in *Arabidopsis*; their isolation and characterization by DNA microarray analysis and bioinformatics. Plant J. 46, 708-721). For quantitative PCR, cDNA templates were generated as described previously. Cycle thresholds were determined per transcript in triplicate using the ABI PRISM 7700 sequence detection system (Applied Biosystems, Foster City, Calif., USA) using SYBR Green I (Applied Biosystems, Foster City, Calif., USA) as reporter dye. Primer sets for the transcripts are DMR6 (QDMR6F:5'-TGTCATCAACATAGGTGACCAG-3' (SEQ ID NO: 8) and QDMR6R: 5'-CGATAGTCACG-GATTTTCTGTG-3') (SEQ ID NO: 9), At1g14880 (QAt1g14880F:5'-CTCAAGGAGAATGGTCCACA-3' (SEQ ID NO: 10) and QAt1g14880R: 5'-CGACTTGGC-CAAATGTGATA-3') (SEQ ID NO: 11), At4g14365 (QAt4g14365F: 5'-TGGTTTTCTGAGGCATGTAAA-3' (SEQ ID NO: 12) and QAt4g14365R:5'-AGTGCAG-GAACATTGGTTGT-3') (SEQ ID NO: 13), ACD6 (QACD6F:5'-TGGACAGTTCTGGAGCAGAT-3' (SEQ ID NO: 14) and QACD6R: 5'-CAACTCCTCCGCTGTGAG-3') (SEQ ID NO: 15), PR-5 (QPR-5F:5'-GGCAAATATCTC-CAGTATTCACA-3' (SEQ ID NO: 16) and QPR-5R: 5'-GG-TAGGGCAATTGTTCCTTAGA-3') (SEQ ID NO: 17), PR-2 (QPR-2 F:5'-AAGGAGCTTAGCCTCACCAC-3' (SEQ ID NO: 18) and QPR-2R: 5'-GAGGGAAGCAAGAATGGAAC-3') (SEQ ID NO: 19), PR-1 (QPR-1F:5'-GAACACGTGCAATGGAGTTT-3' (SEQ ID NO: 20) and QPR-1R: 5'-GGTTCCACCATTGT-TACACCT-3') (SEQ ID NO: 21) and ACT-2 (QACT2 F:5'-AATCACAGCACTTGCACCA-3' (SEQ ID NO: 22) and QACT2R: 5'-GAGGGAAGCAAGAATGGAAC-3') (SEQ ID NO: 23) generating 100 base pair fragments.

Results

Characterization of the Gene Responsible for Pathogen Resistance in the dmr6 Mutant Van Damme et al., 2005, supra disclose a dmr6 mutant that is resistant to *H. parasitica*. The level of resistance can be examined by counting the number of sporangiophores per seedling seven day post inoculation with the *H. parasitica* (isolate Waco9 or Cala2, obtainable from Dr. G. Van den Ackerveken, Plant-Microbe Interactions Group, University of Utrecht, Utrecht, NL). The parental line, Ler eds1-2 (Parker et al., 1996, Plant Cell 8:2033-2046), which is highly susceptible, is used as a positive control (and is set at 100%).

Figure 6B:
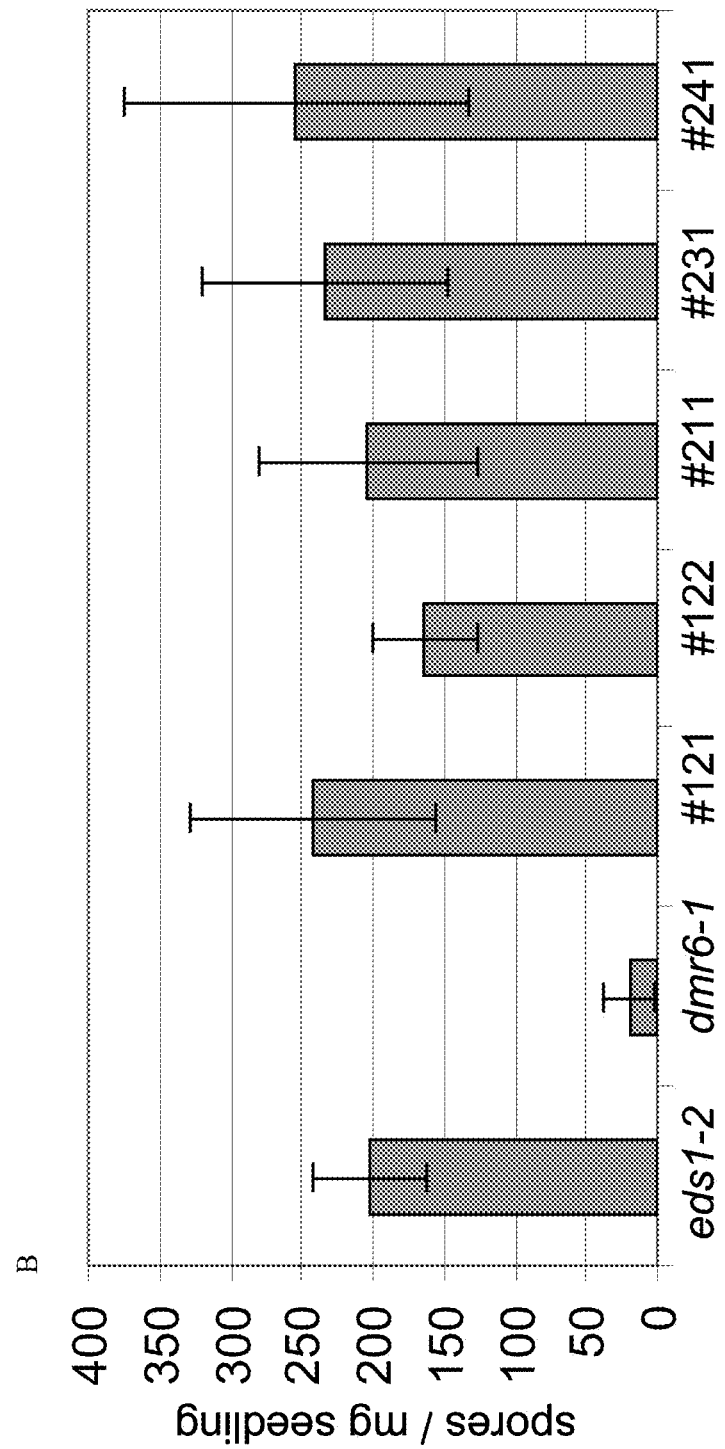

The reduction in sporangiophore formation on the infected dmr6 mutants compared to seedlings of the parental lines is shown in FIG. 6a, wherein the results of the quantification of *Hyaloperonospora parasitica*, Waco9 sporulation (sporangiophores/seedling) on the downy mildew resistant dmr6-1 mutant, back-crossed twice to the parental line Ler eds1-2, and on mutant dmr6-2 (FLAG_445D09 T-DNA line) compared to the control lines is shown.

Figure 7:
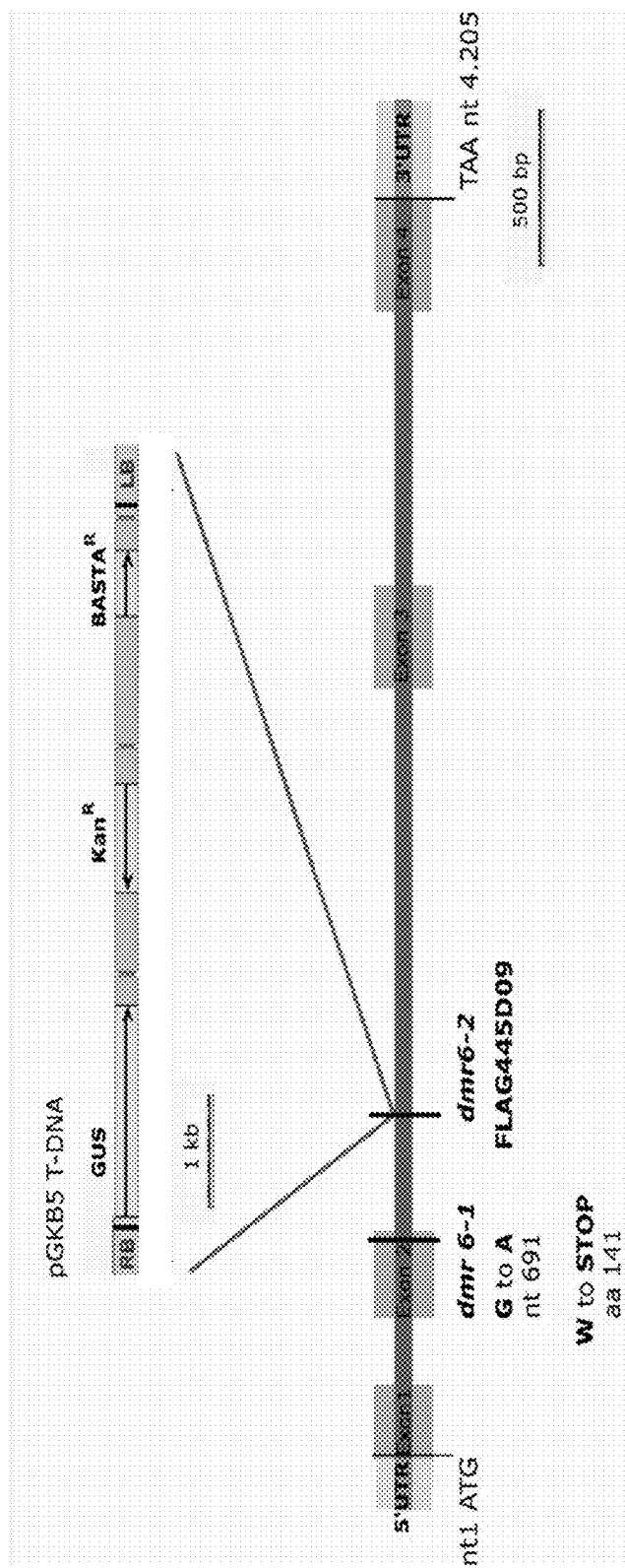
FIG. 7 shows the structure of the *Arabidopsis* DMR6 gene and dmr6-1 and dmr6-2 mutations. The DMR6 gene contains four exons and a coding sequence of 1026 bases. The two alleles are indicated; dmr6-1 with a base change in exon 2, and dmr6-2 with a T-DNA insertion into intron 2.

According to the invention, the gene responsible for resistance to *H. parasitica* in the dmr6 mutants of van Damme et al., 2005, supra, has been cloned by a combination of mapping and sequencing of candidate genes. Previously, the recessive dmr6 mutation was mapped near the nga139 marker on chromosome 5 to a region encompassing 74 genes. Fine mapping linked the dmr6 locus to a mapping interval containing the BACs T13K7 and K18P6 between the markers At5g24420 and At5g24590 located in the corresponding genes. This allowed the dmr6 interval to be confined to a region of 18 candidate genes. Comparative sequence analysis of the 18 genes in dmr6 and the parental line, Ler eds1-2 revealed a point mutation in the second exon of the At5g24530 gene. This single base change of G to A, typical for an EMS mutation, changes a TGG a (trp codon) to a TGA (premature stop codon) at nucleotide position 691 of the coding sequence (FIG. 7). The early stop codon truncates the predicted oxidoreductase enzyme of 342 aa at position 141 before the conserved catalytic domain suggesting that dmr6 is a null-allele. The At5g24530 coding sequence (FIG. 2) is predicted to encode a protein with a mass of 39.4 kDa. No biological role has so far been described for At5g24530.

At5g24530 is DMR6

A second allele, dmr6-2, was identified in a T-DNA insertion line (FLAG_445D09) from the mutant collection from INRA, Versailles. The presence and location of the T-DNA insert in the second intron of At5g24530 (FIG. 7) was confirmed by PCR and sequence analysis (data not shown). Progeny of the FLAG_445D09 line homozygous for the T-DNA insertion was resistant to *H. parasitica* isolate Waco9, whereas the parental line (Ws-4) was susceptible (FIG. 6a). The At5g24530 transcript could be amplified by RT-PCR using primers in exon 2 and 3 in Ws-4, but not in the homozygous dmr6-2 line (data not shown), indicating that dmr6-2 can be considered a second null-allele.

To corroborate the idea that At5g24530 is required for susceptibility to *H. parasitica* the dmr6-1 mutant was transformed with the cDNA from At5g24530 cloned under control of the 35S promoter. In five independent dmr6-1 T2 seedlings the strong overexpression of At5g24530 was confirmed by RT-PCR (data not shown). All T3 lines, homozygous for the transgene, showed restoration of susceptibility to *H. parasitica* isolate Cala2 (FIG. 6b), confirming that At5g24530 is DMR6. The complementation, together with the identification of two independent dmr6 mutants clearly indicates that a functional DMR6 gene is required for susceptibility to *H. parasitica*.

DMR6 is Transcriptionally Activated During *H. parasitica* Infection

Figure 8:
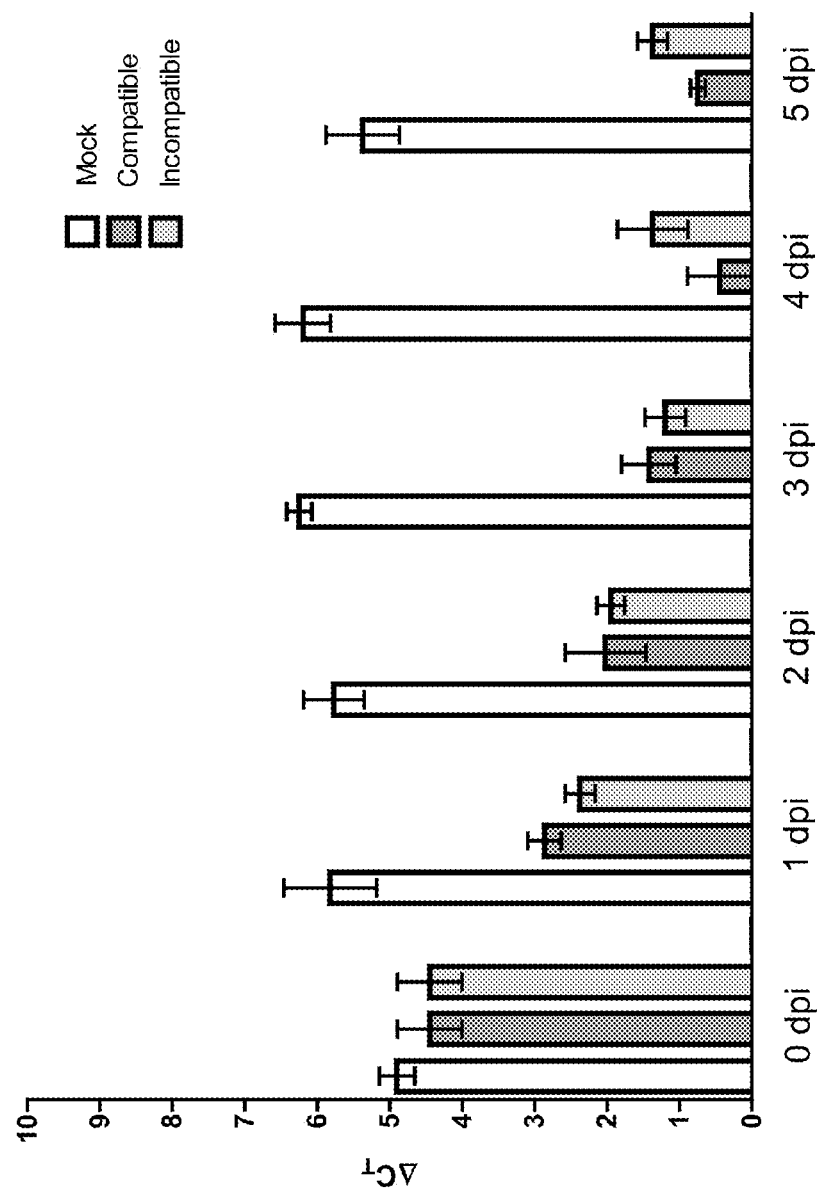
FIG. 8 shows the relative transcript levels of DMR6 in Ler plants either mock treated or inoculated with a compatible or incompatible *H. parasitica* isolate. Transcript levels were determined at different days post inoculation. The difference in cycle threshold ($\Delta CT$) values reflect the number of additional PCR amplification cycles required to reach an arbitrary threshold product concentration as compared to ACTIN2. A lower $\Delta CT$ value indicates a higher transcript level.

To study the expression of DMR6 during infection with *H. parasitica* relative transcript levels were measured by quantitative PCR at six different time points from 0 days (2 hours) post inoculation to 5 days post inoculation (dpi) (FIG. 8). RNA was isolated from ten day old Ler seedlings that were spray inoculated with water (mock), compatible, or incompatible *H. parasitica* isolate. At 2 hours post inoculation (0 dpi) the levels of DMR6 transcripts were equal in the different treatments. Starting from 1 dpi, the level of DMR6 transcript was significantly increased in both the compatible and incompatible interaction compared to mock-treated seedlings. The DMR6 transcript level was slightly but significantly higher at 1 dpi in the incompatible interaction (ACT of 3.5, approximately 11 fold induction) than in the compatible (ACT of 3.0, approximately 8 fold induction). The expression level increased further in time to reach a stable high level at 4-5 dpi. At these time points the DMR6 transcript level was higher in the compatible than in the incompatible interaction. The elevated DMR6 transcript levels during compatible and incompatible *H. parasitica* interactions suggest a role of DMR6 in plant defense. The defense-associated expression of DMR6 could be confirmed in our three enhanced-defense mutants, dmr3, dmr4, and dmr5 (Van den Ackerveken et al., unpublished). Furthermore, in silico analysis of DMR6 levels in the Genevestigator Mutant Surveyor (Zimmermann, P., Hennig, L., and Gruissem, W. (2005). Gene-expression analysis and network discovery using Genevestigator. Trends Plant Sci. 10, 407-409) showed that the gene is strongly induced in the pathogen resistant mutants mpk4 and cpr5. In the cpr5/npr1 double mutant the DMR6 transcript level remained high indicating that the induction of DMR6 expression is mostly NPR1 independent. Salicylic acid appears to be an important signal in the induction of DMR6 expression during senescence as nahG transgenic plants (expressing the bacterial salicylate hydroxylase gene) showed only low levels of DMR6 transcript.

Figure 9:
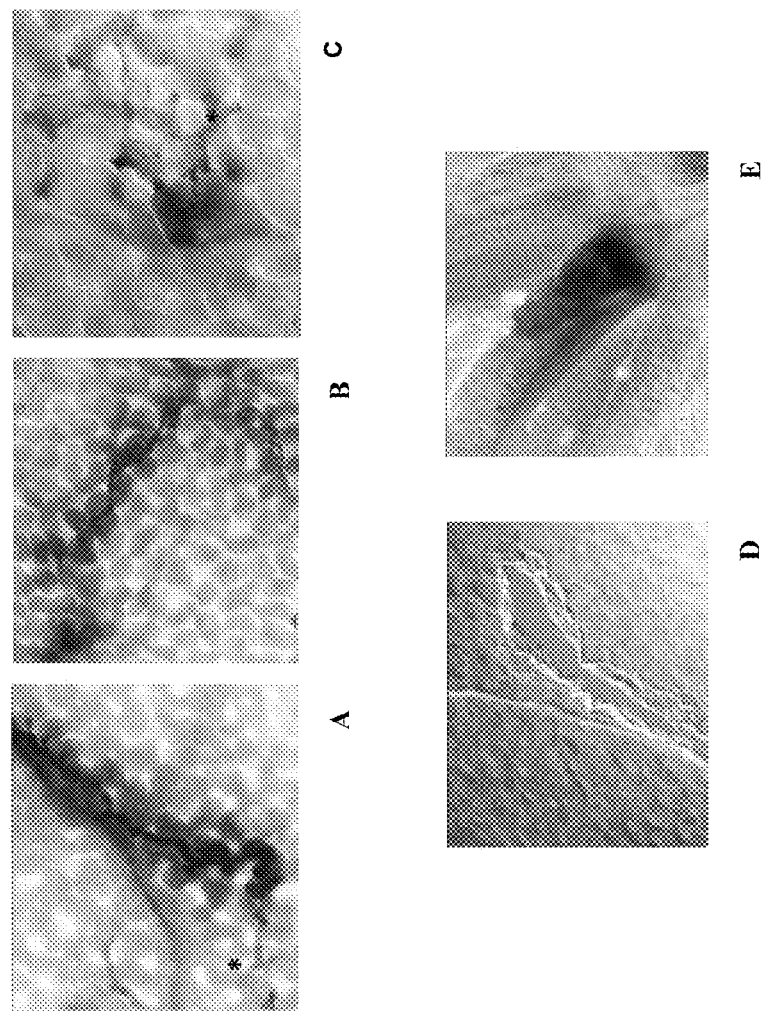
FIG. 9 shows the expression of the DMR6 promoter-reporter (pDMR6::GUS) construct in transgenic *Arabidopsis* lines, visualized with only X-gluc as substrate (Figure d and e) or Magenta-Xgluc (Figure a-c) and trypan blue staining of *H. parasitica* growth (a) Ler eds1-2 (pDMR6::GUS) 3 dpi with *H. parasitica*, Cala2 isolate. (b) Col-0 (pDMR6::GUS) 3 dpi with *H. parasitica*, Waco9 isolate. (c) Ler eds1-2 (pDMR6::GUS) 3 dpi with *H. parasitica*, Emoy2 isolate. (d) Col-0 (pDMR6::GUS) 3 dp wounding. (e) Col-0 (pDMR6::GUS) 3 dp BTH application.

To investigate in more detail how the expression of DMR6 is activated during biotic and abiotic stress, DMR6 reporter lines were generated. The localization of DMR6 expression was studied in transgenic Col-0 and Ler eds1-2 plants containing the DMR6 promoter linked to the uidA (β-glucuronidase, GUS) reporter gene (pDMR6::GUS). To visualize both *H. parasitica* hyphal growth, by staining with trypan blue, as well as GUS activity, magenta-Xgluc was used as a β-glucuronidase substrate yielding a magenta precipitate. In uninfected plants no GUS expression could be detected in the different plant organelles; roots, meristem, flower, pollen and seed. The expression of DMR6 was induced in the compatible interactions, Ler eds1-2 infected with Cala2 (FIG. 9a), and Col-0 infected with isolate Waco9 (FIG. 9b). GUS expression was also induced in the incompatible interaction Ler eds1-2 inoculated with isolate Emoy2 (FIG. 9c). As shown in FIGS. 9a and 9b DMR6 expression was confined to the cells in which *H. parasitica* had formed haustoria. Plant cells containing the most recently formed haustoria did not show detectable levels of GUS activity (FIG. 9a, indicated by asterisk). During the incompatible interaction (FIG. 9c) activity of the DMR6 promoter could only be detected in the cells that were in contact with the initial invading hyphae. In death cells, resulting from the hypersensitive response (HR, visualized by trypan blue staining indicated in FIG. 9c by asterisk) no GUS activity could be detected, possibly due to protein degradation in these cells. To test if the DMR6 expression in haustoria-containing cells is caused by a wound-like response, seedlings were wound by incision with scissors and stained for GUS activity 3 days later. No detectable promoter DMR6 GUS expression was seen, indicating that the expression of DMR6 is not induced by wounding (FIG. 9d). Furthermore the local induction of DMR6 expression was tested in response to treatment with benzothiadiazole (BTH), a functional analogue of salicylic acid (SA). At 3 days post BTH treatment GUS activity was mainly localized in the newly formed, but not in the mature leaves (FIG. 9e). Analysis of pDMR6::GUS lines confirm the expression data described above and highlights the strictly localized induction of DMR6 in response to *H. parasitica* infection.

The dmr6-1 Mutant Constitutively Expresses Defense Associated Transcripts

Figure 10A:
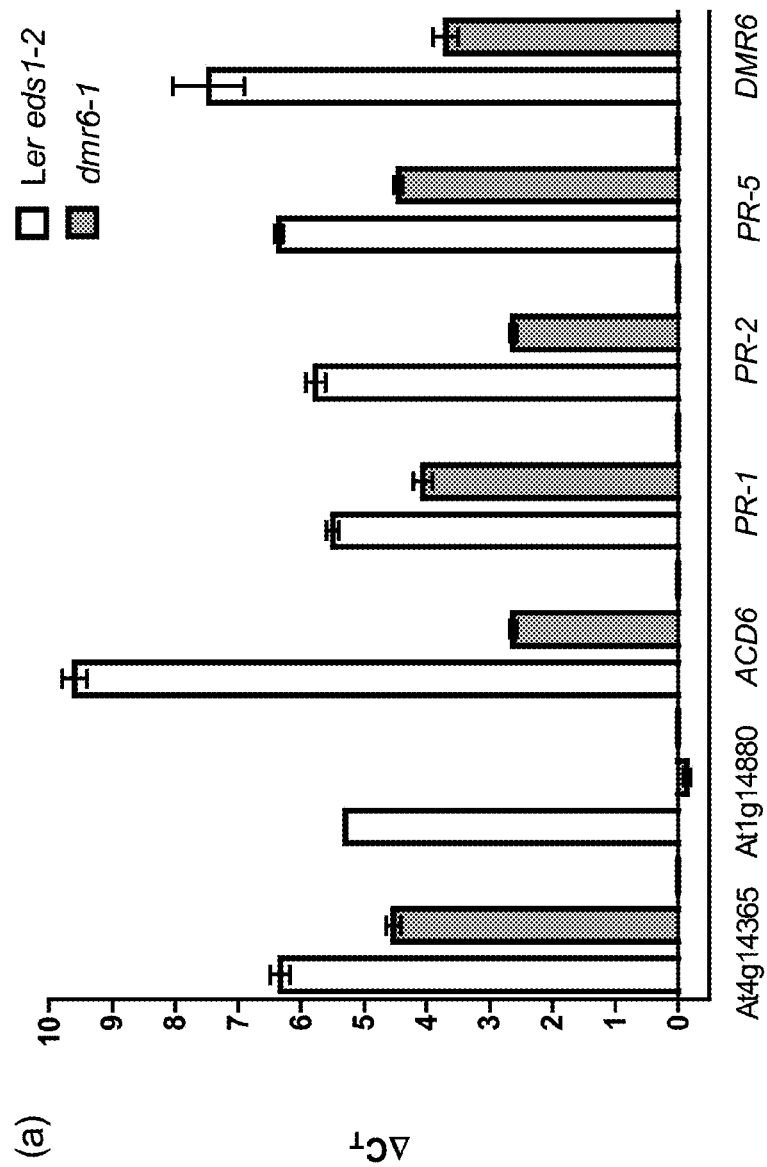
FIG. 10A-B shows the Q-PCR analysis of the transcript levels of the genes; At4g14365, At1g14880, ACD6, PR-1, PR-2 and PR-5, selected as up regulated in the dmr6-1 micro array analysis. (a) Transcription levels of the six genes in dmr6-1 compared to Ler eds1-2 and additionally the DMR6 transcript. (b) Elevated gene transcripts of six defense-associated genes in dmr6-2 versus Ws-4. $\Delta CT$ reflects the number of additional PCR amplification cycles required to reach the level of ACTIN2 transcripts. A lower $\Delta CT$ value indicates a higher transcript level.
Figure 10B:
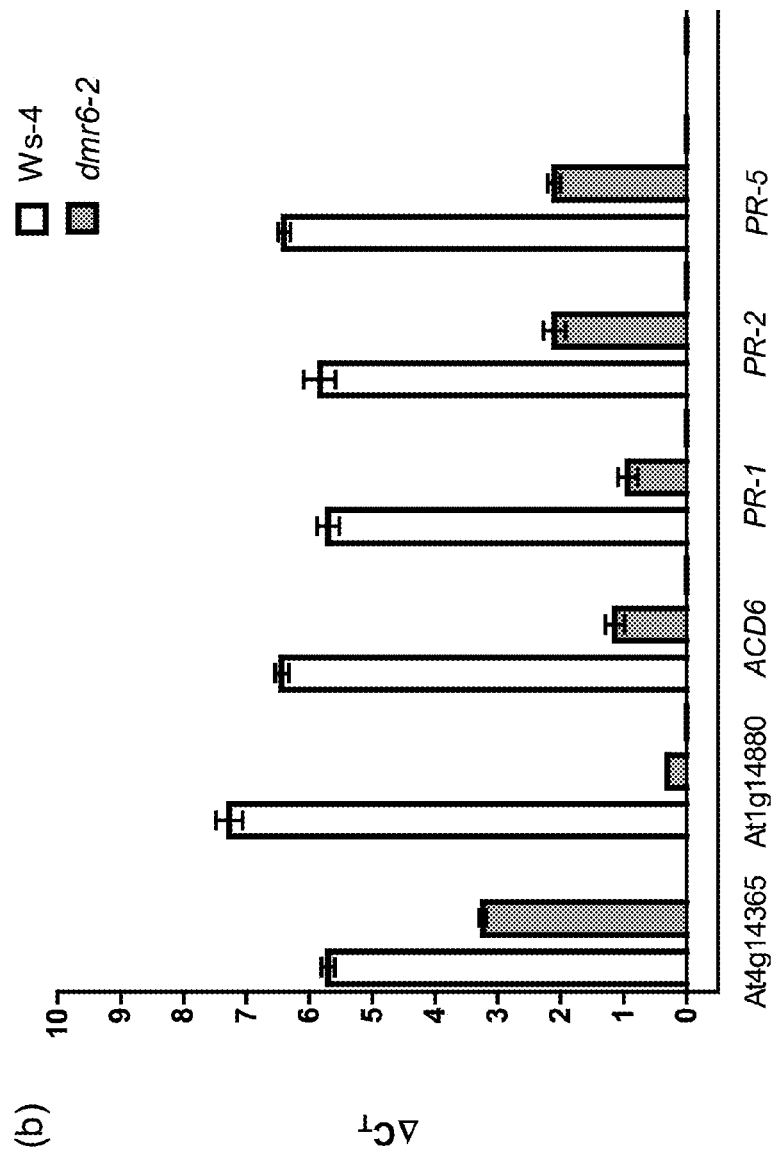

To elucidate how the lack of DMR6 results in *H. parasitica* resistance, the transcriptome of the dmr6-1 mutant compared to the Ler eds1-2 parental line was analyzed. Probes derived from mRNA of the above-ground parts of 14 day old dmr6-1 and Ler eds1-2 seedlings were hybridized on whole genome CATMA micro arrays. A total of 58 genes were found to be significantly differentially expressed in dmr6-1, of which 51 genes had elevated and 7 genes had reduced transcript levels. A pronounced set of the 51 induced transcripts have been identified as genes associated with activated plant defense responses, e.g., ACD6, PR-5, PR-4/HEL and PAD4. These data indicate that the loss of DMR6 results in the activation of a specific set of defense-associated transcripts. The finding that DMR6 is among the dmr6-1-induced genes corroborates the idea that DMR6 is defense-associated. To test if the induced expression of the defense-associated genes was due to the loss of DMR6 and not due to additional ethane methyl sulfonate (EMS) mutations remaining in the backcrossed dmr6-1 mutant the transcript level of a selection of genes (At4g14365, At1g14880, ACD6, PR-1, PR-2 and PR-5) was verified by quantitative PCR in both the dmr6-1 and dmr6-2 mutant (FIG. 10). We could only test DMR6 transcript levels in the dmr6-1 mutant (FIG. 10a) as the dmr6-2 mutant (FIG. 10b) has a T_DNA insertion disrupting the DMR6 transcript. The induction of DMR6 as observed in the micro array analysis was confirmed by Q-PCR in dmr6-1 compared to Ler eds1-2 (FIG. 10a). FIGS. 10a and b show that all six selected genes were elevated in both dmr6 mutants compared to the parental lines. The observed elevated expression of the selected defense-associated genes in the dmr6 mutants indicates that lack of DMR6 activates a plant defense response. The activation of this set of defense-associated transcripts could be the primary cause of resistance to *H. parasitica* in the dmr6 mutants.

Example 2

Identification of DMR6 Orthologs in Crops
1. Screening of Libraries on the Basis of Sequence Homology The nucleotide and amino acid sequences of the DMR6 coding sequence and protein of *Arabidopsis thaliana* are shown in FIG. 2. Public libraries of nucleotide and amino acid sequences were compared with the sequences of FIG. 2. This comparison resulted in identification of the complete DMR6 coding sequences and predicted amino acid sequences in *Aquilegia* species, *Citrus sinensis*, *Coffea canephora*, *Cucumis sativus*, *Gossypium hirsutum*, *Lactuca sativa*, *Medicago truncatula*, *Oryza sativa* (3), *Populus trichocarpa* (2), *Solanum lycopersicum* (2), *Sorghum bicolor*, *Spinacia oleracea*, *Vitis vinifera*, *Zea mays*, and *Zingiber officinale*. The sequence information of the orthologous proteins thus identified is given in Table 1 and visualized in a multiple alignment in FIG. 1. For many other plant species orthologous DNA fragments could be identified by BlastX as reciprocal best hits to the *Arabidopsis* or other plant DMR6 protein sequences.
2. Identification of Orthologs by Means of Heterologous Hybridisation The DMR6 DNA sequence of *Arabidopsis thaliana* as shown in FIG. 2 is used as a probe to search for homologous sequences by hybridization to DNA of any plant species using standard molecular biological methods. Using this method orthologous genes are detected by southern hybridization on restriction enzyme-digested DNA or by hybridization to genomic or cDNA libraries. These techniques are well known to the person skilled in the art. As an alternative probe the DMR6 DNA sequence of any other more closely related plant species can be used as a probe.
3. Identification of Orthologs by Means of PCR For many crop species, partial DMR6 mRNA or gene sequences are available that are used to design primers to subsequently PCR amplify the complete cDNA or genomic sequence. When 5' and 3' sequences are available the missing internal sequence is PCR amplified by a DMR6 specific 5' forward primer and 3' reverse primer. In cases where only 5', internal or 3' sequences are available, both forward and reverse primers are designed. In combination with available plasmid polylinker primers, inserts are amplified from genomic and cDNA libraries of the plant species of interest. In a similar way, missing 5' or 3' sequences are amplified by advanced PCR techniques; 5'RACE, 3' RACE, TAIL-PCR, RLM-RACE or vectorette PCR.

As an example the sequencing of the *Lactuca sativa* (lettuce) DMR6 cDNA is provided. From the Genbank EST database at NCBI several *Lactuca* DMR6 ESTs were identified using the tblastn tool starting with the *Arabidopsis* DMR6 amino acid sequence. Clustering and alignment of the ESTs resulted in a consensus sequence for a 5' DMR6 fragment. To obtain the complete lettuce DMR6 cDNA the RLM-RACE kit (Ambion) was used on mRNA from lettuce seedlings. The 3' mRNA sequence was obtained by using two primers that were designed in the 5' DMR6 consensus sequence derived from ESTs (Lsat_dmr6_fw1: CGATCAAGGTCAACACATGG (SEQ ID NO: 24), and Lsat_dmr6_fw2: TCAACCATTACCCAGTGTGC) (SEQ ID NO: 25) and the 3'RACE primers from the kit. Based on the assembled sequence new primers were designed to amplify the complete DMR6 coding sequence from cDNA to provide the nucleotide sequence and derived protein sequence as presented in FIG. 3.

The complete DMR6 coding sequences from more than 10 different plants species have been identified from genomic and EST databases. From the alignment of the DNA sequences, conserved regions in the coding sequence were selected for the design of degenerate oligonucleotide primers (for the degenerate nucleotides the abbreviations are according to the IUB nucleotide symbols that are standard codes used by all companies synthesizing oligonucleotides; G=Guanine, A=Adenine, T=Thymine, C=Cytosine, R=A or G, Y=C or T, M=A or C, K=G or T, S=C or G, W=A or T, B=C or G or T, D=G or A or T, H=A or C or T, V=A or C or G, N=A or C or G or T).

The procedure for obtaining internal DMR6 cDNA sequences of a given plant species is as follows:
1. mRNA is isolated using standard methods,
2. cDNA is synthesized using an oligo dT primer and standard methods,
3. using degenerate forward and reverse oligonucleotides a PCR reaction is carried out,
4. PCR fragments are separated by standard agarose gel electrophoresis and fragments of the expected size are isolated from the gel,
5. isolated PCR fragments are cloned in a plasmid vector using standard methods,
6. plasmids with correct insert sizes, as determined by PCR, are analysed by DNA sequencing,
7. Sequence analysis using blastX reveals which fragments contain the correct internal DMR6 sequences,
8. The internal DNA sequence can then be used to design gene- and species-specific primers for 5' and 3' RACE to obtain the complete DMR6 coding sequence by RLM-RACE (as described above).

As an example the sequencing of the *Cucumis sativus* (cucumber) DMR6 cDNA is provided. For cucumber several primer combinations between the following primers were successful in amplifying a stretch of internal coding sequence from cDNA; forward primers dmr6_deg_fw1B (TTCCAGGTDATTAAYCAYGG) (SEQ ID NO: 26), dmr6_deg_fw2B CATAAYTGGAGRGAYTAYCT) (SEQ ID NO: 27), dmr6_deg_fw3B (GARCAAGGRCAR-CAYATGGC) (SEQ ID NO: 28) and dmr6_deg_fw4 (AATCCTCCTTCHTTCAAGGA) (SEQ ID NO: 29) and reverse primers dmr6_deg_rv3B (AGTGCATTKGGGTCH-GTRTG) (SEQ ID NO: 30), dmr6_deg_rv4 (AATGTTRAT-GACAAARGCAT) (SEQ ID NO: 31) and dmr6_deg_rv5 (GCCATRTGYTGYCCTTGYTC) (SEQ ID NO: 32). After cloning and sequencing of the amplified fragments cucumber DMR6-specific primers were designed for 5' RACE (Cuc_dmr6_rv1: TCCGGACATTGAAACTTGTG (SEQ ID NO: 33) and Cuc_dmr6_rv2: TCAAAGAACTGCTTGC-CAAC) (SEQ ID NO: 34) and 3' RACE (Cuc_dmr6_fw1: CGCACTCACCATTCTCCTTC (SEQ ID NO: 35) and Cuc_dmr6_fw2: GGCCTCCAAGTCCTCAAAG) (SEQ ID NO: 36). Finally the complete cucumber DMR6 cDNA sequence was amplified and sequenced (FIG. 5). A similar approach was a used for spinach, *Spinacia oleracea* (FIG. 4), *Solanum lycopersicum* (FIG. 12) and *Nicotiana benthamiana* (FIG. 13).

Orthologs identified as described in this example can be modified using well-known techniques to induce mutations that reduce the DMR6 expression or activity, to obtain non-genetically modified plants resistant to Fungi or Oomycota. Alternatively, the genetic information of the orthologs can be used to design vehicles for gene silencing, and to transform the corresponding crop plants to obtain plants that are resistant to Oomycota.

Example 3

Mutation of Seeds

Seeds of the plant species of interest are treated with a mutagen in order to introduce random point mutations in the genome. Mutated plants are grown to produce seeds and the next generation is screened for the absence of reduction of DMR6 transcript levels or activity. This is achieved by monitoring the level of DMR6 gene expression, or by searching for nucleotide changes (mutations) by the TILLING method, by DNA sequencing, or by any other method to identify nucleotide changes. The selected plants are homozygous or are made homozygous by selfing or intercrossing. The selected homozygous plants with absent or reduced DMR6 transcript activity are tested for increased resistance to the pathogen of interest to confirm the increased disease resistance.

Example 4

Transfer of a Mutated Allele into the Background of a Desired Crop

Introgression of the desired mutant allele into a crop is achieved by crossing and genotypic screening of the mutant allele. This is a standard procedure in current-day marker assistant breeding of crops.

Example 5

Use of the DMR6 Promotor for Pathogen-Induced Gene Expression and the Generation of Disease Resistant Plants Precise control of transgene expression is pivotal to the engineering of plants with increased disease resistance. In the past, constitutive overexpression of transgenes frequently has resulted in poor quality plants. It has therefor been suggested to use pathogen-inducible promotors, by which the transgenes are expressed only when and where they are needed—at infection sites.

Local and inducible expression of engineered genes, e.g., master switch genes, elicitor or Avr genes, anti-microbial genes, or toxic genes, results in the activation of defense or cell death that will lead to pathogen resistance, such as described by Gurr and Rushton (Trends in Biotechnology 23: 275-282, 2005). A good example is provided by De with (Annu. Rev. Phytopathol. 30: 391-418, 1992) who proposes the use of the Avr9-Cf9 combination to achieve induced cell death leading to disease resistance. The tissue-specificity and inducibility of expression is of prime importance for such approaches, as described by Gurr and Rushton (Trends in Biotechnology 23: 283-290, 2005).

According to the present invention, the DMR6 promoter has been demonstrated to show a strong, inducible, localized expression based on promoter-GUS analysis. Thus, the DMR6 promotor is very suitable for engineering disease resistance in transgenic plants. The DMR6 promoter consists of a region of 2.5 kb that is upstream of the *Arabidopsis* DMR6 coding sequence (ATG start codon) and includes the 5'UTR (as depicted in FIG. 11). This pathogen-inducible promoter is then used to engineer suitable transgene constructs, using standard techniques known the person skilled in the art.

Using orthologous DNA sequences from a given plant species primers are designed for PCR. These are then used to screen genomic libraries of the plant species of interest to identify the genomic clones that contain the DMR6 ortholog with its promoter and regulatory sequences. Alternatively, the genomic clones are isolated by screening a library with a labelled PCR fragment corresponding to the DMR6 orthologous gene. Sequencing reveals the nucleotide sequence of the promoter. The region of 2-5 kb upstream the DMR6 orthologous coding sequence (ATG start codon), so including the 5'UTR, is then amplified by PCR to engineer transgene constructs for plant transformation.

Example 6

This example demonstrates the complementation of mutant dmr6-1 in *Arabidopsis thaliana* by DMR6 orthologs from 4 different crop species. For this, DMR6 orthologs of *Cucumis sativa* (Cs), *Spinacia oleracea* (So), *Lactuca sativa* (Ls) and *Solanum lycopersicum* (Sl) were cloned into a plant expression vector under the control of the 35S promoter and, subsequently, this vector was transformed into a *Arabidopsis thaliana* mutant dmr6-1.

Briefly, mRNA was isolated using standard methods and cDNA was synthesized using an oligo dT primer and standard methods. Subsequently, PCR fragments were generated using primer pairs for each crop as depicted in table 3 below. The generated PCR products were cloned into a pENTR/D-TOPO vector using the pENTR/D-TOPO cloning kit from Invitrogen and resulting plasmids with correct insert sizes, as determined by PCR, were analyzed by DNA sequencing. Recombination to the pB7WG2,0 vector was done using LR clonase II from Invitrogen and the resulting plasmids were analyzed by PCR and digestion with restriction enzymes. Suitable plasmids were transformed into *Agrobacterium tumefaciens* C58C1 PGV2260 and plasmids from *Agrobacterium* were analyzed by PCR and digestion with restriction enzymes.

*Arabidopsis thaliana* dmr6-1 plants were transformed with the above constructs by dipping into *Agrobacterium* solution and overexpression of crops DMR6 in *Arabidopsis* T1 plants is verified by RT-PCR using the crops DMR6 cloning primers (table 3). Finally, *Arabidopsis* T2 and T3 plants were infected with *Hyaloperonospora parasitica* Cala2 to confirm complementation. The results are shown in FIG. 14.

Figure 14:
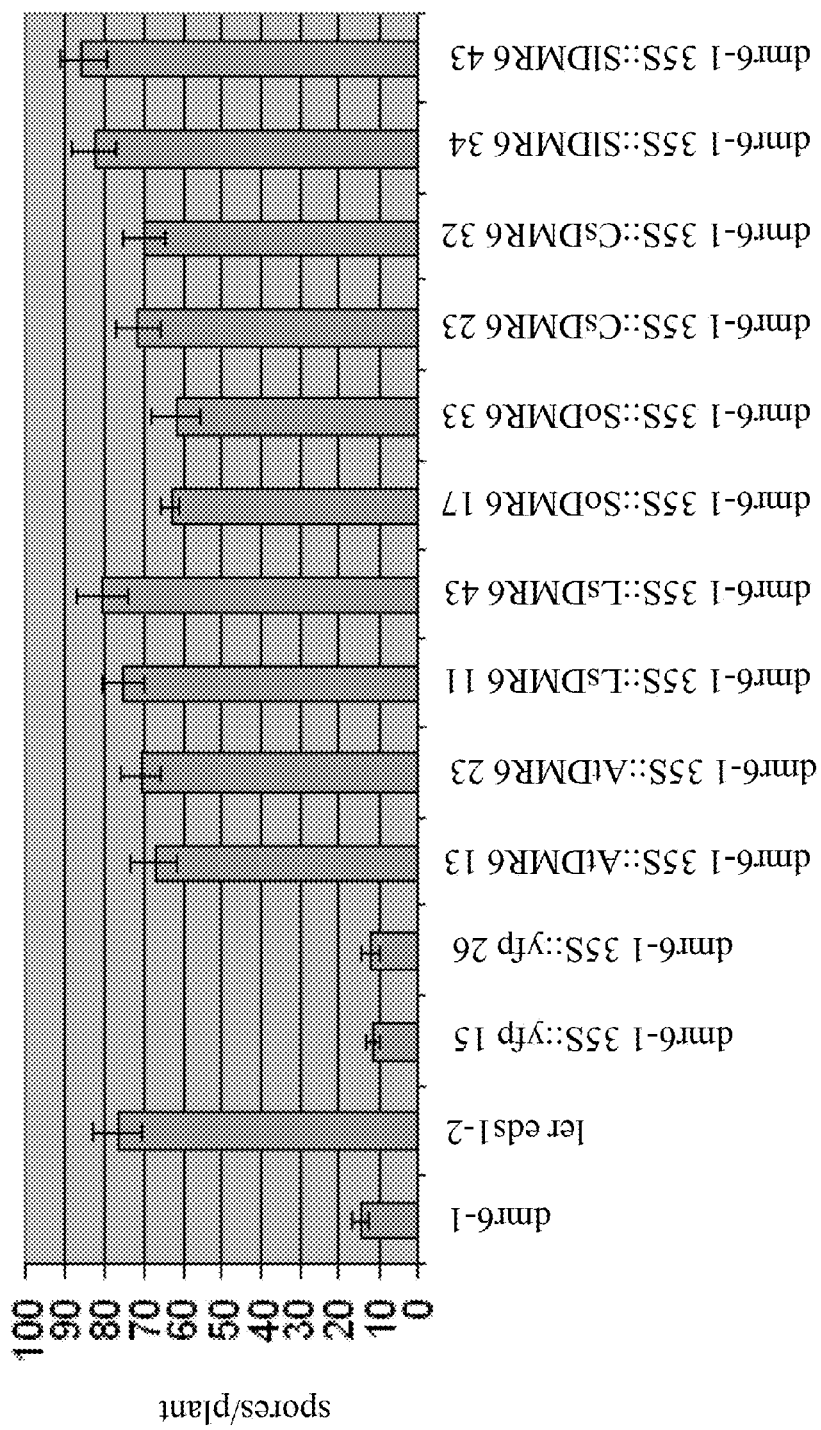
FIG. 14 shows complementation of *Arabidopsis thaliana* dmr6-1 with DMR6 derived from *Cucumis sativa* (Cs), *Spinacia oleracea* (Si), *Lactuca sativa* (Ls) and *Solanum lycopersicum* (So).

As shown in FIG. 14, all DMR6 orthologs tested were capable of complementing *Arabidopsis thaliana* mutant dmr6-1 indicating that the DMR6 orthologs identified encode DMR6 proteins with a similar functionality as *Arabidopsis thaliana* DMR6.

Tables

Table 1 lists the GI numbers (GenInfo identifier) and Genbank accession number for Expressed Sequence Tags (ESTs) and mRNA or protein sequences of the *Arabidopsis* DMR6 mRNA and orthologous sequences from other plant species. A GI number (genInfo identifier, sometimes written in lower case, "gi") is a unique integer which identifies a particular sequence. The GI number is a series of digits that are assigned consecutively to each sequence record processed by NCBI. The GI number will thus change every time the sequence changes. The NCBI assigns GI numbers to all sequences processed into Entrez, including nucleotide sequences from DDBJ/EMBL/GenBank, protein sequences from SWISS-PROT, PIR and many others. The GI number thus provides a unique sequence identifier which is independent of the database source that specifies an exact sequence. If a sequence in GenBank is modified, even by a single base pair, a new GI number is assigned to the updated sequence. The accession number stays the same. The GI number is always stable and retrievable. Thus, the reference to GI numbers in the table provides a clear and unambiguous identification of the corresponding sequence.

TABLE 1

| Species | Common name | Detail | GI number | Genbank |
|---|---|---|---|---|
| *Arabidopsis thaliana* | Thale cress | mRNA | 42568064 | NM_122361 |
| *Aquilegia_sp* | Aquilegia | ESTs | 75461114 | DT768847.1 |
| | | | 74538666 | DT745001.1 |
| | | | 74562677 | DT760187.1 |
| | | | 75461112 | DT768846.1 |
| | | | 74562675 | DT760186.1 |
| *Citrus sinensis* | Sweet Orange | ESTs | 5793134 | CX672037.1 |
| | | | 57933368 | CX673829.1 |
| | | | 63078039 | CX309185.1 |
| *Coffea canephora* | Coffea | ESTs | 82485203 | DV705375.1 |
| | | | 82458236 | DV684837.1 |
| | | | 82461999 | DV688600.1 |
| | | | 82487627 | DV707799.1 |
| *Gossypium hirsutum* | Cotton | ESTs | 109842586 | DW241146.1 |
| | | | 48751103 | CO081622.1 |
| *Sorghum bicolor* | Sorghum | ESTs | 45992638 | CN150358.1 |
| | | | 57813436 | CX614669.1 |
| | | | 45985339 | CN145819.1 |
| | | | 57821006 | CX622219.1 |
| | | | 45989371 | CN148311.1 |
| | | | 57821495 | CX622708.1 |
| | | | 45959033 | CN130459.1 |
| | | | 45985193 | CN145752.1 |
| | | | 18058986 | BM322209.1 |
| | | | 45958822 | CN130381.1 |
| | | | 30164583 | CB928312.1 |
| *Medicago truncatula* | Barrel medic | Genome draft protein | 92878635 | MtrDRAFT_AC119415g1v1 ABE85154 |
| *Oryza sativa* 1 | Rice | Genome protein | 18057095 | OSJNBb0060I05.4 AAL58118.1 |
| *Oryza sativa* 2 | | mRNA protein | 115450396 115450397 | NM_001055334 NP_001048799 |
| *Oryza sativa* 3 | | mRNA protein | 115460101 115460102 | NM_001060186 NP_001053651 |
| *Populus trichocarpa* 1 | Poplar | | | Genome: LG_XII: 3095392-3103694 protein: Poptr1_1: 569679, eugene3.00120332 |
| *Populus trichocarpa* 2 | Poplar | | | Genome: LG_XV: 201426-209590 protein: Poptr1_1: 732726, estExt_Genewise1_v1.C_LG_XV0083 |
| *Solanum lycopersicum* 1 | Tomato | ESTs | 62932307 | BW689896.1 |
| | | | 58229384 | BP885913.1 |
| | | | 117682646 | DB678879.1 |
| | | | 5894550 | AW035794.1 |
| | | | 117708809 | DB703617.1 |
| | | | 62934028 | BW691617.1 |
| | | | 15197716 | BI422913.1 |
| | | | 4381742 | AI486371.1 |
| | | | 5601946 | AI896044.1 |
| | | | 4387964 | AI484040.1 |
| | | | 4383017 | AI487646. |
| | | | 5278230 | AI780189.1 |
| | | | 12633558 | BG133370.1 |
| | | | 76572794 | DV105461.1 |
| | | | 117692514 | DB718569.1 |
| | | | 4385331 | AI489960.1 |
| | | | 4383253 | AI487882.1 |
| | | | 4384827 | AI489456.1 |

TABLE 1-continued

| Species | Common name | Detail | GI number | Genbank |
|---|---|---|---|---|
| Solanum lycopersicum 2 | Tomato | ESTs | 47104686 | BT013271.1 |
| | | | 14685038 | BI207314.1 |
| | | | 14684816 | BI207092.1 |
| Zea mays | Maize | ESTs | 110215403 | EC897301.1 |
| | | | 76291496 | DV031064.1 |
| | | | 91050479 | EB160897.1 |
| | | | 91874282 | EB404239.1 |
| | | | 110540753 | EE044673.1 |
| | | | 78111856 | DV530253.1 |
| | | | 94477588 | EB706546.1 |
| | | | 71441483 | DR822533.1 |
| | | | 78111699 | DV530096.1 |
| | | | 78107139 | DV525557.1 |
| | | | 76017449 | DT944619.1 |
| | | | 91048249 | EB158667.1 |
| | | | 78104908 | DV523326.1 |
| | | | 78088214 | DV516607.1 |
| | | | 76291495 | DV031063.1 |
| | | | 71441482 | DR822532.1 |
| | | | 78088213 | DV516606.1 |
| Vitis vinifera | Grape | ESTs | 33396402 | CF202029.1 |
| | | | 33399765 | CF205392.1 |
| | | | 45770972 | CN006824.1 |
| | | | 45770784 | CN006636.1 |
| | | | 45770528 | CN006380.1 |
| | | | 45770631 | CN006483.1 |
| | | | 33400623 | CF206250.1 |
| | | | 33396335 | CF201962.1 |
| | | | 30134763 | CB920101.1 |
| | | | 30305300 | CB982094.1 |
| | | | 71857419 | DT006474.1 |
| | | | 30305235 | CB982029.1 |
| Zingiber officinale | Ginger | ESTs | 87108948 | DY375732.1 |
| | | | 87095447 | DY362231.1 |
| | | | 87095448 | DY362232.1 |
| | | | 87094804 | DY361588.1 |
| | | | 87095449 | DY362233.1 |
| | | | 87094803 | DY361587.1 |
| Lactuca sativa | Lettuce | | Sequence described in this patent application | |
| Spinacia oleracea | Spinach | | Sequence described in this patent application | |
| Cucumis sativus | Cucumber | | Sequence described in this patent application | |
| Nicotiana benthamiana | Tabac | | Sequence described in this patent application | |

TABLE 2

Primer sequences of insertion/deletion markers (size difference in brackets) used in the mapping and cloning of the DMR6 gene.

| Name primer | Gene | INDEL/ enzyme | Forward primer | Reverse primer |
|---|---|---|---|---|
| IND_MOP9 | At5G24210 | | tttgggaacagaaaa agttggaggt (SEQ ID NO: 37) | catattcaaaaggga aaatcccaga (SEQ ID NO: 38) |
| IND_K16H17 | At5g24420 | | tggggttgtggttta ttctgttgac (SEQ ID NO: 39) | tggccaatagtagtt gatacgcaaga (SEQ ID NO: 40) |
| IND_T4C12 | At5g24820 | | tctcgggtaagacac aagtcgagat (SEQ ID NO: 41) | tattccaacttgcga cgtagagcat (SEQ ID NO: 42) |
| IND_T11H3 | At5g24950-60 | | ccaattgggttattt acttcgatt (SEQ ID NO: 43) | cggcttttaacaaca tattttcca (SEQ ID NO: 44) |
| IND_F21J6 | At5g25270 | | aacacatcaccaaga tgaatccaga (SEQ ID NO: 45) | cctctgccccaagaa atattgagat (SEQ ID NO: 46) |
| M450 | At5G24450 | 18 | agctttgtatggtag tgccaatga (SEQ ID NO: 47) | gcggtatacggggt taaaatcta (SEQ ID NO: 48) |

TABLE 2-continued

Primer sequences of insertion/deletion markers (size difference in brackets) used in the mapping and cloning of the DMR6 gene.

| Name primer | Gene | INDEL/ enzyme | Forward primer | Reverse primer |
|---|---|---|---|---|
| M490 | At5g24490 | TaqI | atggccaaccactct ttgttac (SEQ ID NO: 49) | acaagcaagaagaac agcgaag (SEQ ID NO: 50) |
| M525 | At5g24520-30 | TaqI | gaaatttggttgttg gcatttatc (SEQ ID NO: 51) | tcaagatcttcatat tctcattcca (SEQ ID NO: 52) |
| M545 | At5G24540/50 | 41 | cagctgaagtatgtt tcatcccttt (SEQ ID NO: 53) | cttgcaattgttggg actaggtaa (SEQ ID NO: 54) |
| M555 | At5G24550/60 | 14 | tcactaaccagtgaa aaaggttgc (SEQ ID NO: 55) | tatacagcgaatagc aaagccaag (SEQ ID NO: 56) |
| M470 | At5g24470 | HphI | ccgcgagtgtaatat atctctcct (SEQ ID NO: 57) | cagtttaacgcatga agtgctagt (SEQ ID NO: 58) |
| M590 | At5g24590 | PdmI | gcatcatttgtaccg tactgagtc (SEQ ID NO: 59) | tagtggatactctgt ccctgaggt (SEQ ID NO: 60) |

TABLE 3

Primer pairs for cloning dmr6 orthologs in a suitable plant expression vector

| | | | | | |
|---|---|---|---|---|---|
| Arabidopsis thaliana | AtDMR6_fw | CACCATGGCGGCAAA GCTGATA (SEQ ID NO: 85) | | spiUTR_rv | TTGCTGCCTACAAAA GTACAAA (SEQ ID NO: 90) |
| | AtDMR6UTR_rv | GACAAACACAAAGGC CAAAGA (SEQ ID NO: 86) | Lactuca sativa | Lsat_fw | CACCATGGCCGCAAA AGTCATCTC (SEQ ID NO: 91) |
| Cucumis sativa | cuc_fw | CACCATGGAGCAGTGT GATGGAGAT (SEQ ID NO: 87) | | LsatUTR_rv | CATGGAAACACATAT TCCTTCA (SEQ ID NO: 92) |
| | cucUTR_rv | TGGGCCAAAAAGTTT ATCCA (SEQ ID NO: 88) | Solanum lycopersicum | Slyc1dmr6_fw | CACCATGGAAACCAA AGTTATTTCTAGC (SEQ ID NO: 93) |
| Spinacia oleracea | spi_fw | CACCATGGCAAACAA GATATTATCCAC (SEQ ID NO: 89) | | Slyc1dmr6UTR_rv | GGGACATCCCTATGA ACCAA (SEQ ID NO: 94) |

The invention claimed is:

1. An isolated tomato plant which is resistant to *Phytophthora infestans*, wherein the tomato plant has a reduced level or reduced activity of the DMR6 protein of SEQ ID NO: 96 as compared to a tomato plant that is not resistant to *Phytophthora infestans*, and wherein said isolated tomato plant has a non-natural mutation introduced into the dmr6 gene of SEQ ID NO: 95.

2. The tomato plant as claimed in claim 1, wherein the mutation in the dmr6 gene leads to an amino acid substitution in the DMR6 protein.

3. A seed, tissue, or plant part of the tomato plant according to claim 1, wherein the seed, tissue, or plant part comprises the mutation in the dmr6 gene of SEQ ID NO: 95 and has a reduced level or reduced activity of the DMR6 protein of SEQ ID NO: 96.

4. A method for obtaining a tomato plant which is resistant to *Phytophthora infestans*, comprising reducing an endogenous level of the DMR6 protein of SEQ ID NO: 96 in a tomato plant by introducing a mutation into the dmr6 gene of SEQ ID NO: 95.

5. The method according to claim 4, wherein reducing the endogenous level of the DMR6 protein in the tomato plant is achieved by reducing expression of the dmr6 gene of SEQ ID NO: 95.

6. The method according to claim 5, wherein reducing expression of the dmr6 gene of SEQ ID NO: 95 is achieved by gene silencing or RNAi.

7. The method according to claim 4, wherein the mutation results in one or more amino acid changes that leads to a reduced enzymatic activity of the DMR6 protein of SEQ ID NO: 96.

8. The method according to claim 4, wherein the mutation is effected by a mutagenic treatment of the tomato plant.

9. The method according to claim 8, wherein the mutagenic treatment is effected with a mutagen or with radiation.

10. A tomato plant produced from the method according to claim 4, wherein the plant comprises the mutation in the dmr6 gene of SEQ ID NO: 95 and has a reduced level or reduced activity of the DMR6 protein of SEQ ID NO: 96.

11. A seed, tissue, or plant part of the tomato plant according to claim 10, wherein the seed, tissue, or plant part comprises the mutation in the dmr6 gene of SEQ ID NO: 95 and has a reduced level or reduced activity of the DMR6 protein of SEQ ID NO: 96.

* * * * *